United States Patent
Sharma et al.

(10) Patent No.: US 9,814,451 B2
(45) Date of Patent: Nov. 14, 2017

(54) HANDLE MECHANISM PROVIDING UNLIMITED ROLL

(71) Applicant: FlexDex, Inc., Brighton, MI (US)

(72) Inventors: Deepak Sharma, Ann Arbor, MI (US); Gregory Brian Bowles, Fenton, MI (US); James Michael Licht, Howell, MI (US); Zachary Zimmerman, Waterford, MI (US); Shorya Awtar, Ann Arbor, MI (US); James Duncan Geiger, Toledo, OH (US)

(73) Assignee: FlexDex, Inc., Brighton, MI (US)

( * ) Notice: Subject to any disclaimer, the term of this patent is extended or adjusted under 35 U.S.C. 154(b) by 0 days.

(21) Appl. No.: 15/284,345

(22) Filed: Oct. 3, 2016

(65) Prior Publication Data
US 2017/0095236 A1   Apr. 6, 2017

Related U.S. Application Data

(60) Provisional application No. 62/236,835, filed on Oct. 2, 2015.

(51) Int. Cl.
*A61B 17/00* (2006.01)
*A61B 17/29* (2006.01)

(52) U.S. Cl.
CPC ...... *A61B 17/00* (2013.01); *A61B 2017/0042* (2013.01); *A61B 2017/00424* (2013.01); *A61B 2017/00442* (2013.01)

(58) Field of Classification Search
CPC ............ A61B 17/00; A61B 2017/0042; A61B 2017/00424; A61B 2017/00442
See application file for complete search history.

(56) References Cited

U.S. PATENT DOCUMENTS

| 3,497,083 A | 2/1970 | Anderson et al. |
| 4,328,839 A | 5/1982 | Lyons et al. |

(Continued)

FOREIGN PATENT DOCUMENTS

| GB | 0937587 A | 10/1964 |
| JP | 3-292879 A | 12/1991 |

(Continued)

OTHER PUBLICATIONS

Awtar et al.; A minimally invasive surgical tool with enhanced dexterity and intuitive actuation; J. Med. Devices; 4(3); 8 pages; (Author's Draft; 12 pages); Sep. 10, 2010.

(Continued)

*Primary Examiner* — Gary Jackson
*Assistant Examiner* — Boniface N Nganga
(74) *Attorney, Agent, or Firm* — Shay Glenn LLP

(57) ABSTRACT

Devices having a handle that provides unlimited roll to an end-effector at the distal end of the device. For example, described herein are medical devices that have an elongate tool frame, an end-effector, and a handle that includes: a first portion, a second portion that rolls relative to the first portion, a push rod within the first portion connected to a control input, and a shuttle body within the second portion that rotates with the second portion but is axially driven by the push rod when the user actuates the control input. The device may include a proximal wrist/forearm attachment allowing one or more degrees of freedom in pitch, yaw or roll about the user's arm. The handle may articulate relative to the tool frame, and this articulation may be transmitted to the end-effector. The end-effector may be a jaw assembly.

17 Claims, 35 Drawing Sheets

(56) References Cited

U.S. PATENT DOCUMENTS

| | | |
|---|---|---|
| 4,466,649 A | 8/1984 | Ozawa |
| 4,568,311 A | 2/1986 | Miyake |
| 4,712,545 A | 12/1987 | Honkanen |
| 4,750,475 A | 6/1988 | Yoshihashi |
| 4,754,909 A | 7/1988 | Barker et al. |
| 4,950,273 A | 8/1990 | Briggs |
| 5,021,969 A | 6/1991 | Okamura et al. |
| 5,069,596 A | 12/1991 | Mueller et al. |
| 5,147,357 A | 9/1992 | Rose et al. |
| 5,209,747 A | 5/1993 | Knoepfler |
| 5,297,443 A | 3/1994 | Wentz |
| 5,317,952 A | 6/1994 | Immega |
| 5,323,570 A | 6/1994 | Kuhlman et al. |
| 5,330,502 A | 7/1994 | Hassler et al. |
| 5,350,391 A | 9/1994 | Iacovelli |
| 5,368,600 A | 11/1994 | Failla et al. |
| 5,374,277 A | 12/1994 | Hassler |
| 5,454,827 A | 10/1995 | Aust et al. |
| 5,456,695 A | 10/1995 | Dallemagne |
| 5,549,637 A | 8/1996 | Crainich |
| 5,599,151 A | 2/1997 | Daum et al. |
| 5,620,415 A | 4/1997 | Lucey et al. |
| 5,626,608 A | 5/1997 | Cuny et al. |
| 5,683,412 A | 11/1997 | Scarfone |
| 5,713,505 A | 2/1998 | Huitema |
| 5,716,352 A | 2/1998 | Viola et al. |
| 5,735,874 A | 4/1998 | Measamer et al. |
| 5,782,748 A | 7/1998 | Palmer et al. |
| 5,807,376 A | 9/1998 | Viola et al. |
| 5,817,084 A | 10/1998 | Jensen |
| 5,820,009 A | 10/1998 | Melling et al. |
| 5,853,412 A | 12/1998 | Mayenberger |
| 5,860,995 A | 1/1999 | Berkelaar |
| 5,908,436 A | 6/1999 | Cuschieri et al. |
| 6,270,453 B1 | 8/2001 | Sakai |
| 6,309,403 B1 | 10/2001 | Minor et al. |
| 6,312,435 B1 | 11/2001 | Wallace et al. |
| 6,330,837 B1 | 12/2001 | Charles et al. |
| 6,714,839 B2 | 3/2004 | Salisbury et al. |
| 6,853,879 B2 | 2/2005 | Sunaoshi |
| 6,889,116 B2 | 5/2005 | Jinno |
| 6,994,716 B2 | 2/2006 | Jinno et al. |
| 7,101,363 B2 | 9/2006 | Nishizawa et al. |
| 7,147,650 B2 | 12/2006 | Lee |
| 7,553,275 B2 | 6/2009 | Padget et al. |
| 7,608,083 B2 | 10/2009 | Lee et al. |
| 7,708,756 B2 | 5/2010 | Nobis et al. |
| 7,736,254 B2 | 6/2010 | Schena |
| 8,029,531 B2 | 10/2011 | Lee et al. |
| 8,425,408 B2 | 4/2013 | Boulais et al. |
| 8,465,475 B2 | 6/2013 | Isbell |
| 8,528,440 B2 | 9/2013 | Morley et al. |
| 8,540,748 B2 | 9/2013 | Murphy et al. |
| 8,551,076 B2 | 10/2013 | Duval et al. |
| 8,603,135 B2 | 12/2013 | Mueller |
| 8,668,702 B2 | 3/2014 | Awtar et al. |
| 8,672,206 B2 | 3/2014 | Aranyi et al. |
| 8,764,448 B2 | 7/2014 | Yang et al. |
| 8,992,422 B2 | 3/2015 | Spivey et al. |
| 9,161,771 B2 | 10/2015 | Steger |
| 9,220,398 B2 | 12/2015 | Woodley et al. |
| 9,696,700 B2 | 7/2017 | Beira et al. |
| 2001/0031983 A1 | 10/2001 | Brock et al. |
| 2003/0036748 A1 | 2/2003 | Cooper et al. |
| 2003/0135203 A1 | 7/2003 | Wang et al. |
| 2003/0176880 A1 | 9/2003 | Long et al. |
| 2003/0176948 A1 | 9/2003 | Green |
| 2004/0023616 A1 | 2/2004 | Straub et al. |
| 2004/0138700 A1 | 7/2004 | Cooper et al. |
| 2004/0253079 A1 | 12/2004 | Sanchez |
| 2005/0004431 A1 | 1/2005 | Kogasaka et al. |
| 2005/0038469 A1 | 2/2005 | Lang |
| 2005/0107667 A1 | 5/2005 | Danitz et al. |
| 2006/0111210 A1 | 5/2006 | Hinman |
| 2006/0111616 A1 | 5/2006 | Danitz |
| 2006/0259073 A1 | 11/2006 | Miyamoto et al. |
| 2006/0282063 A1 | 12/2006 | Gotani |
| 2007/0021738 A1 | 1/2007 | Hasser et al. |
| 2007/0078565 A1 | 4/2007 | Ghodoussi et al. |
| 2008/0039256 A1 | 2/2008 | Jinno et al. |
| 2008/0065098 A1 | 3/2008 | Larkin |
| 2008/0177285 A1 | 7/2008 | Brock et al. |
| 2010/0004606 A1 | 1/2010 | Hansen et al. |
| 2010/0016853 A1 | 1/2010 | Burbank |
| 2010/0030018 A1 | 2/2010 | Fortier et al. |
| 2010/0056863 A1 | 3/2010 | Dejima et al. |
| 2010/0234831 A1 | 9/2010 | Hinman et al. |
| 2011/0118707 A1 | 5/2011 | Burbank |
| 2011/0152881 A1 | 6/2011 | Conner et al. |
| 2011/0152922 A1 | 6/2011 | Jeong |
| 2012/0095298 A1 | 4/2012 | Stefanchik et al. |
| 2012/0186383 A1 | 7/2012 | Schvalb et al. |
| 2012/0277762 A1 | 11/2012 | Lathrop et al. |
| 2013/0012958 A1 | 1/2013 | Marczyk et al. |
| 2013/0023868 A1 | 1/2013 | Worrell et al. |
| 2013/0023974 A1 | 1/2013 | Amrani |
| 2013/0066334 A1 | 3/2013 | Schoepp |
| 2013/0172860 A1 | 7/2013 | Szewczyk et al. |
| 2013/0239734 A1 | 9/2013 | Hinman |
| 2014/0135805 A1 | 5/2014 | Windgassen et al. |
| 2014/0142595 A1 | 5/2014 | Awtar et al. |
| 2014/0371532 A1 | 12/2014 | Trovato |
| 2015/0164601 A1 | 6/2015 | Sholev |
| 2015/0230697 A1 | 8/2015 | Phee et al. |
| 2016/0135830 A1 | 5/2016 | Volkmer et al. |
| 2016/0256232 A1 | 9/2016 | Awtar et al. |
| 2016/0291383 A1 | 10/2016 | Han et al. |
| 2016/0303734 A1 | 10/2016 | Bowles et al. |
| 2017/0245954 A1 | 8/2017 | Beira |

FOREIGN PATENT DOCUMENTS

| | | |
|---|---|---|
| JP | 8-84702 A | 4/1996 |
| JP | 2002102248 A | 4/2002 |
| JP | 2003061969 A | 3/2003 |
| JP | 2007130485 A | 5/2007 |
| WO | WO2006/036067 A2 | 4/2006 |
| WO | WO2007/146894 A2 | 12/2007 |
| WO | WO2008/020964 A2 | 2/2008 |
| WO | WO2014/033717 A1 | 3/2014 |
| WO | WO2015/125140 A1 | 8/2015 |
| WO | WO2016/063213 A1 | 4/2016 |
| WO | WO2016/161449 A1 | 10/2016 |

OTHER PUBLICATIONS

Do et al.; Adaptive control of position compensation for cable-conduit mechanisms used in flexible surgical robots; Proceedings of the 11th International Conference on Informatics in Control, Automation and Robotics (ICINCO-2014); IEEE; pp. 110-117; Sep. 1, 2014.

Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.

Simaan et al.; A dexterous system for laryngeal surgery; Proceedings of the 2004 IEEE International Conference on Robotics and Automation; New Orleans, LA.; pp. 351-357; Apr. 2004.

Licht et al.; U.S. Appl. No. 15/286,489 entitled "Medical devices having smoothly articulating multi-cluster joints," filed Oct. 5, 2016.

Zimmerman et al.; U.S. Appl. No. 15/286,547 entitled "End-effector jaw closure transmission system for remote access tools," filed Oct. 5, 2016.

Clement et al.; Design of a Snake-Like Manipulator; Robotics and Autonomous Systems; 6(3); pp. 265-282; Jul. 1990.

Ikuta et al.; Shape Memory Alloy Servo Actuator System With Electric Resistance Feedback and Application for Active Endoscope (conf. paper); 1988 IEEE Int'l Conf. on Robotics and Automation; pp. 427-430; Apr. 24-29, 1988.

(56) References Cited

OTHER PUBLICATIONS

Jug et al.; The JPL Serpentine Robot: a 12 DOF System for Inspection (Conference Paper); Proceedings—IEEE International Conference on Robotics and Automation 3: 5 pgs.; Jun. 1995.
Walker et al.; Novel 'Elephant''s Trunk' Robot; IEEE/ASME International Conference on Advanced Intelligent Mechatronics, AIM; Piscataway, NJ, United States; pp. 410-415; Sep. 19-23, 1999.
Wikipedia; Constant Velocity Joint; 6 pgs.; retrieved from the Internet (https://en.wikipedia.org/wiki/Constant-velocity_joint) on Dec. 22, 2016.

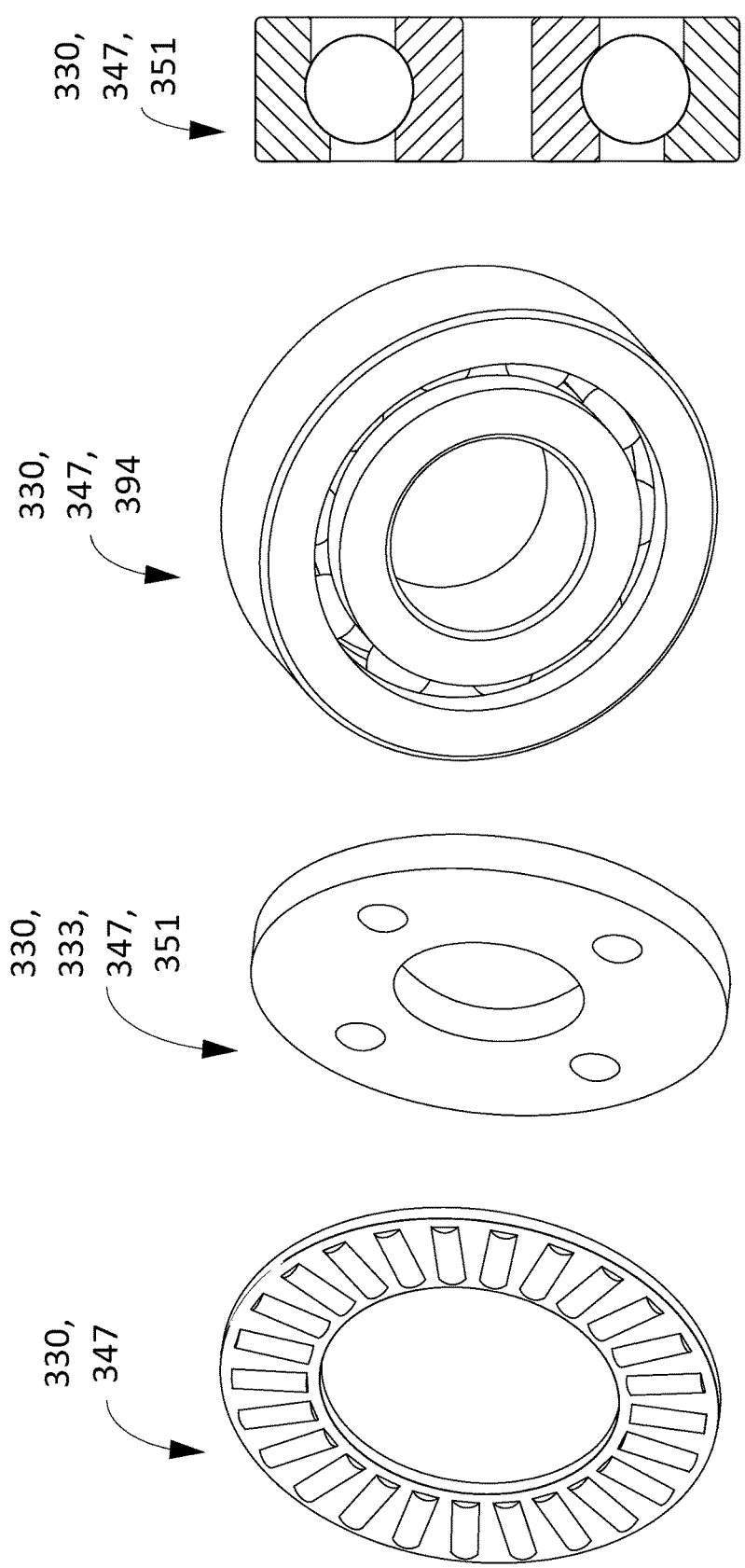

HANDLE MECHANISM PROVIDING UNLIMITED ROLL

CROSS REFERENCE TO RELATED APPLICATIONS

This application claims priority to U.S. Provisional Patent Application No. 62/236,835, titled "HANDLE ROTATION MECHANISM" filed on Oct. 2, 2015, and is herein incorporated by reference in its entirety.

This application may also be related to U.S. patent application Ser. No. 15/130,915, titled "ATTACHMENT APPARATUS FOR REMOTE ACCESS TOOLS" filed on Apr. 15, 2016, which claimed priority to U.S. Provisional Patent Application No. 62/147,998, titled "FOREARM ATTACHMENT APPARATUS FOR REMOTE ACCESS TOOLS" filed on Apr. 15, 2015, and U.S. Provisional Patent Application No. 62/236,805, titled "FOREARM ATTACHMENT APPARATUS FOR REMOTE ACCESS TOOLS" filed on Oct. 2, 2015. This application may also be related to U.S. patent application Ser. No. 15/054,068, titled "PARALLEL KINEMATIC MECHANISMS WITH DECOUPLED ROTATIONAL MOTIONS" filed on Feb. 25, 2016, which claims priority as a continuation-in-part to U.S. patent application Ser. No. 14/166,503, titled "MINIMAL ACCESS TOOL" filed on Jan. 28, 2014, Publication No. US-2014-0142595-A1, which is a continuation of U.S. patent application Ser. No. 12/937,523, titled "MINIMUM ACCESS TOOL" filed on Apr. 13, 2009, now U.S. Pat. No. 8,668,702, which claimed priority to U.S. Provisional Patent Application No. 61/044,168, titled "MINIMALLY INVASIVE SURGICAL TOOL" filed on Apr. 11, 2008. Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are rotation mechanisms for inputs or handles, and apparatuses and applications using them. For example, described herein are handles with an unlimited rotation mechanism ("unlimited roll handles") and apparatuses for minimally invasive surgical tools and remote access tools using them.

BACKGROUND

A number of remote access tools and minimally invasive surgical tools which incorporate handles with unlimited ("infinite") rotation mechanisms are known, for example, WO 2007/146894 A2. This application describes, for example, laparoscopy tools primarily consisting of a proximal handle, a tool frame/tool shaft and distal end-effector (EE). In some of these laparoscopic devices, to rotate the end-effector about the tool shaft axis (i.e., to provide a roll rotation of the end-effector), the user may have to rotate the handle about its own center axis. While the handle may fit or conform in the user's hand, palm, and/or fingers in the nominal condition (i.e., prior to any roll rotation), it may no longer continue to fit/conform with the user's hand during and after the roll rotation. In fact, the handle may start to collide with areas of the hand holding the device during rotation, typically limiting the amount of roll rotation and/or requiring repositioning of the handle within the surgeon's hand to achieve maximum roll rotation at the end-effector. Thus, many of these devices may require more than one hand to operate, or may require repositioning of the device during operation within a user's hand in order to continue to roll in a single direction beyond a limited amount of roll. The process of repositioning usually results in a loss of access to the input joint/mechanism between the tool shaft/frame and handle and loss of ergonomics at the handle to hand interface. Attempts have been made to address the challenge of limited rotation and reduced ergonomics by providing a rotational joint in the handle between the stationary portion of the handle that is held by user's hand, palm, finger(s) and/or thumb in the nominal condition and the roll portion that is rotated with respect to the stationary portion about its center axis by the user's finger(s) and/or thumb; these attempts have met with only limited success, in part because rolling the device in this manner may result in winding of internal cabling, including actuating cables and the like when rolling the stationary portion relative to the roll portion (e.g., dial, handle dial, rotation dial or the like). The stationary portion of the handle is defined stationary as far as roll rotation motion is concerned. This stationary portion may move along with the user's hand to provide other degree of freedoms (e.g., pitch and yaw rotations in articulating laparoscopic devices).

These devices that incorporate the stationary portion and roll portion in the handle assembly, may be articulating or non-articulating. In some non-articulating devices, the handle and tool shaft can be rigidly connected and rotation of the entire handle may drive rotation of the tool shaft and end-effector. In other non-articulating devices, the handle and tool shaft can be rigidly connected and the handle may be equipped with a dial, where the dial is connected to the end effector and drives the rotation of the end-effector via a roll transmission member routed through the tool shaft. Furthermore, laparoscopic devices are becoming more complex and catering to challenging laparoscopic procedures. Laparoscopic tools may now include articulating end-effectors that can be driven by an input joint between the tool shaft and the handle. Articulating end-effectors enable the surgeon to alter the axis of roll rotation at the end-effector by articulating the handle about an input joint with respect to the tool shaft. The handle in such device is not rigidly connected to the tool shaft but instead connected via an input joint that generally allows two articulation degrees of freedoms, e.g., yaw rotation and pitch rotation, and constrains (and therefore transmits) roll rotation. In some articulating devices, rotation of the end effector may be transmitted via rotation of the dial portion of the handle, which further transmits roll to the end effector via rotation of tool shaft. Here, tool shaft is connected to the handle via an input articulation joint providing yaw and pitch degree of freedoms but transmits roll rotation from the handle to the tool shaft. Similarly, the roll rotation of the tool shaft is transmitted to the end-effector via the output articulating joint. An example of such device configuration is an articulation device sold by Novare™ (International Patent Application Publication WO2007/146894 A2). In other articulating devices, articulation transmission and roll transmission are decoupled such that roll is directly transmitted from the rotation of the dial portion of handle to the end-effector via a separate roll transmission member and not via the kinematics of the input articulation joint, tool shaft, and output articulation joint. This roll transmission member may be torsionally stiff to transmit roll rotation. This roll transmission member may or may not be routed through the input articulation joint and/or the tool frame/tool shaft. An example of such device configuration is an articulation device sold by Covedien™ (U.S. Pat. No. 8,603,135). Some articulating devices in aforementioned configuration provide unlimited roll capability of the articulated end effector, caused by rotation of the handle dial about its own center axis.

Typically, the enhanced dexterity that these articulating tools may offer comes with the tradeoff of increased resistance to roll rotation of the handle and therefore the end-effector when the end-effector and therefore the handle are articulated. This resistance may get further exemplified when the handle input lever to operate the end effector actuation (e.g., opening and closing of a moving portion of the end effector relative to a reference portion of the end effector, that does not move relative to the moving portion) is engaged while performing articulation as well as roll rotation of the end effector. Engagement of a handle input lever to actuate opening/closing of an end-effector having a jaw at the end of the tool shaft, typically results in high loads generated between the stationary portion of the handle held by the user and rotation portion of the handle (dial), that interface with each other to allow rotation. The result of the high load between these independent bodies is typically an increase in frictional resistance to roll rotation which limits the surgeon's ability to use finesse rotation input at the handle to control the end-effector roll rotation. The high jaw open/close actuation loads are typically transmitted from the handle input by a transmission member such as a steel cable, steel wire, etc. or a monofilament steel or Nitinol rod, etc. These types of transmission members function well to transfer loads to a remote aspect of an instrument, but, due to the complexity in providing articulation, roll and actuation functionality to the end effector in such devices, as well as working within a tight volume to incorporate features to meet these functionalities, it is challenging to incorporate joints and bodies that meet the structural requirements to be able to provide aforementioned functionalities. One of the challenges may be the transmission of roll from handle to the end effector and at the same time, transmit end effector actuation from handle to the end effector.

Described herein are apparatuses (e.g., mechanisms, devices, tools, machines, systems, etc.) including handles with an unlimited roll mechanism which may address these problems.

SUMMARY OF THE DISCLOSURE

Described herein are apparatuses (including mechanisms, instruments, devices, tools, systems, etc.) that may include handles (also referred to as handle assemblies) that provide unlimited (e.g., "infinite") roll of a portion of the handle relative to another portion of the handle, and may transmit this roll to an end-effector in an advantageous manner. The unlimited roll mechanisms described herein may be part of an apparatus that includes the handle, a tool frame (which may be a tool shaft or may include a tool shaft) and an end-effector assembly. In some variations, the apparatus may include an end-effector assembly (or simply, end-effector) that can be articulated with respect to the tool frame via an end-effector articulating joint at the distal end of the device; articulation of the end-effector may be controlled by an input articulation joint (input joint) at the proximal end of the device, including between the handle and the tool frame.

In any of these apparatuses, the tool frame may be interfaced with the arm (e.g., wrist, forearm, etc.) of a user via an arm attachment (e.g., forearm attachment), while the user's hand (palm, fingers, thumb, etc.) is interfaced with the handle. The arm attachment may be connected to the tool frame by a joint (e.g., a bearing) that allows one or more degrees of freedom (e.g., pitch, yaw, roll) between the user's arm and the tool frame. In any of these apparatuses, the end-effector may have at least one moving portion (e.g., a moving jaw) that can be actuated (e.g., opened/closed) by an input control on the handle that causes an output actuation of the end effector via an end-effector jaw actuation member. In some of these apparatuses, the jaw actuation transmission member may be a tension/compression member which may be pulled by the input control in the handle to cause end-effector actuation (say, jaw closure actuation). The same or a different jaw actuation transmission member, either tension/compression member may be used to cause the end-effector actuation (say, jaw opening actuation), undoing the previous actuation. This may lead to a pull (first actuation)-pull (second actuation) operation as part of end-effector actuation or a pull (first actuation)-push (second actuation) operation or a push (first actuation)-pull (second actuation) operation.

In general, the unlimited roll handles described herein may also be referred to as unlimited rotation handles, or as unlimited rotation handle apparatuses, or as unlimited roll handle apparatuses, or the like. In general, stationary portion of the handle may also be referred to as handle shell, or as ergonomic handle shell or as handle body or as first portion of the handle or the like. In general, the rotational portion of the handle may also be referred to as rotation portion, or as rotation dial, or as rotating portion, or as dial or as second portion of the handle or the like. In general, the input control in the handle assembly may also be referred to as control, or as input lever, or as end effector control, or as input lever control or the like.

These unlimited roll handles may allow actuation of a distal end-effector (e.g., open and close of end-effector jaws) by an input control on a first portion of the handle (e.g., a handle body) using an end-effector actuation transmission member comprising a cable (steel, tungsten, etc.), steel wire, etc. or a monofilament steel or Nitinol rod, etc. to transmit actuation from the handle without binding up or disruption of the end-effector actuation. This actuation may happen independent or in parallel or regardless of the other motions, namely end effector articulation and end effector roll rotation.

For example, when the end-effector is a jaw assembly, it may include one or two moving jaws (second and third end-effector portions) that are movable with respect to a base end-effector portion (a first end-effector portion). In some variations, one of the jaws of the jaw assembly may be part of (or rigidly attached to) the base end-effector portion. The one or more movable jaws may be moved by a jaw actuation transmission member that is connected to the shuttle portion of the handle. This open/close action of the jaws in the end-effector assembly may be controlled by an end-effector control that may be a moving body (such as a lever, button, slider, etc.) in the handle. Thus, disclosed herein are unlimited roll rotation mechanisms that may be part of an apparatus that includes a corresponding rotation to an end-effector assembly, while being able to transmit the actuation of the end-effector (e.g., open/close motion) from an end-effector control input in the handle.

The apparatuses described herein may be configured for use in any application, including, but not limited to, medical devices (e.g., surgical devices including minimally invasive devices such as laparoscopes, endoscopes, etc.) and the like. For example, an articulated unlimited roll handle mechanism as described may be used as part of a remote access tool that require finesse rotation about a tool-shaft axis and manipulation or articulation of a tool shaft and/or end-effector. In general, the apparatuses described herein may be useful for a variety of purposes.

As will be described in greater detail herein, any of these apparatuses may include a handle having multiple portions or bodies that are coupled together to provide specific rotational and/or translational degrees of freedom relative to each other to provide a ground portion that may be held within a user's hand (referred to herein as a palm grip, hand grip, grip portion, or the like) and a rotating portion that may be operated by the fingers (including the thumb) of the same hand holding the palm grip (referred to herein as a knob, dial, finger dial, rotation dial etc.). In some variations, the handle may be referred to as a handle assembly, handle mechanism, unlimited roll handle, infinite roll handle, or the like. In some variations the handle includes four interconnected components (or bodies) and an end-effector control input, such as a lever, button, dial or other control, to actuate the end-effector. The four interconnected bodies forming the handle may include a first handle portion (e.g., palm grip), a second handle portion (e.g., finger dial), a push rod (typically, internal to the first handle portion) and a shuttle body (typically, internal to the second handle portion). The push rod is typically a rigid member and may alternatively be referred to as a pull rod. The shuttle body typically connects to (or includes) a portion of an end effector actuation transmission member, such as a transmission cable, for transmitting actuation of the end-effector control input to the end-effector.

For example, a handle configured as an unlimited roll handle mechanism may include a first handle portion that is an outer proximal body configured as a palm grip. Generically, this body may be referred to as handle body A ("H.Body A"). The handle may also include a second handle portion configured as an outer distal body, which may be generically referred to as handle body B ("H.Body B"). These two bodies may be considered independent bodies with an established joint where additional features may exist. Within the joint between these two bodies, there may exist specific geometric features such as ribs, surfaces, edges, washers, bushings, bearings, lubricants, etc. which may function to offer some degrees of freedom while constraining others. The joint of the outer bodies may also be internally traversed by a secondary pair of bodies. These secondary bodies may have portion of them, proximal or distal to the joint between H.Body A and H.Body B. One of the secondary body may be generically referred to herein as handle body C or "H.Body C", and may be, e.g., a proximal push rod having a portion of it connecting to H.Body A; the other secondary body may be generically referred to herein as handle body D or "H.Body D" and may be, e.g., a distal shuttle having a portion of it connecting to H.Body B. Likewise, the joints between either of the inner secondary bodies with respect to each other and with respect to the outer two bodies may also comprise specific geometric features such as ribs, surfaces, edges, washers, bushings, bearings, lubricants, etc. which may function to offer some degrees of freedom while constraining others. A generic description of this four-body structure showing the degrees of constraint and degrees of freedom is illustrated in FIG. 1. A four-body unlimited roll handle such as the one shown generically in FIG. 1 may be incorporated as part of an articulating laparoscopic instrument, for example. A user (such as a physician, doctor, surgeon, etc.) may hold the handle and apply articulation input (causing pitch/yaw motion) through a joint distal or proximal to the handle rotation mechanism. This articulation input (pitch/yaw) joint may connect handle to the tool frame/tool shaft. This articulation input may be transmitted to an articulation output joint (pitch/yaw) at the distal end of the instrument via an articulation transmission member(s). This articulation output joint may connect tool shaft/tool frame to the end effector or end effector assembly. This transmission member(s) connects to the articulation input joint and an output articulating joint (proximal to the end-effector assembly). The surgeon may then rotate the end effector about its center/roll axis (axis 2) by rotation of the second portion or dial body (H.Body B) relative to first portion of the handle, the proximal outer body (H.Body A), about axis 1. While holding (grounding) the proximal outer body (H.Body A, e.g., a palm grip) in his/her palm, the user may rotate the distal outer body (e.g., H.Body B, e.g., a rotation dial) to drive rotation with a finesse twirling motion between the thumb and forefinger. A rotation joint between H.Body A (first portion) and H.Body B (second portion) presented in FIG. 1 may function to reduce friction and relieve the user of strenuous resistances which can otherwise be generated when the user also chooses to activate the jaw closure, for example, by transferring translation about a first axis (e.g., axis 1 in FIG. 1) from H.Body C to H.Body D and generating force in the tension/compression (jaw close/open) transmission member of the handle. As will be described and illustrated in greater detail below, when the user activates the end effector input control at the handle, this motion is transmitted to the translation of H.Body C along a first axis with respect to H.Body A via a transmission mechanism in the handle. The translation of H.Body C is further transmitted to the translation of H.Body D, which is transmitted to an end-effector via an end-effector actuation transmission member. While the transmission happens, the surgeon can also infinitely rotate the handle rotation mechanism clockwise or counterclockwise without twisting the end-effector actuation transmission member due to keying or constrained joints between H.Body B and H.Body D.

In variations in which the handle is used with an articulating joint, such as articulating input joint between the handle and the tool shaft, the articulation input joint may be parallel kinematic (P-K) joint (e.g., U.S. Patent Application Publication 2013/0012958 and U.S. Pat. No. 8,668,702) and/or a virtual center (VC) joint (e.g., U.S. Pat. No. 5,908,436) or a parallel kinematic virtual center joint (U.S. Pat. No. 8,668,702) or a serial kinematic (S-K) joint (e.g., U.S. Pat. No. 8,465,475; U.S. Pat. No. 5,713,505) or a combination of serial kinematic and a parallel kinematic joint. The unlimited roll handles described herein may be particularly useful with apparatuses that are articulating, e.g., having an articulating input joint between the handle and the tool frame (e.g., tool shaft). Here, transmission cables (that is compliant in compression, torsion and bending, such as a rope, braided cable, etc.) may be the effective end effector actuation transmission member and/or end effector articulation member. These highly-compliant transmission members, may be able to bend through tight bend radii and provide effective transmission. Wire that is torsionally stiff but compliant in bending may also be used for either of the two aforementioned transmissions and/or for end effector rotation transmission. Articulation transmission member(s), roll transmission member, and end-effector actuation transmission member may be distinct bodies or they may be combined into one body in a pair or triplet to perform intended transmission. The transmission members may route through different paths to link their respective joints. For example, an articulation transmission member may be routed through the body of the tool frame (e.g., tool shaft), or it may be routed externally to the body of the tool shaft.

As mentioned above, any of the apparatuses described herein may include an unlimited roll handle and an arm (e.g., forearm) attachment so that a proximal end region of the apparatus may be connected to the user's arm/forearm. These apparatuses may permit improved control of the apparatus when the apparatus is rigidly coupled to the user's arm (e.g., having no degrees of freedom between the apparatus and the user's arm), but may be particularly helpful where the arm attachment permits one or more degrees of freedom between the tool frame and the user's arm, such as one or more of roll, pitch and/or yaw degrees of freedom.

For example, described herein are apparatuses, including medical devices, comprising: an elongate tool frame having a forearm attachment portion at a proximal end, the elongate frame having a tool axis; an end-effector at a distal end of the elongate tool frame; a handle that provides unlimited roll to the end-effector, wherein the handle includes: a first handle portion, a second handle portion coupled to the first handle portion so that the second handle portion has one rotational degree of freedom in a first axis relative to the first handle portion but is translationally constrained relative to the first handle portion along the first axis, a push rod completely or partially within the first handle portion and coupled to the first handle portion so that it has one translational degree of freedom along the first axis relative to the first handle portion but is rotationally constrained about the first axis relative to the first handle portion, a shuttle body completely or partially within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion, and an end-effector control input on the first handle portion coupled to the push rod via a mechanism or other transmission system and configured to translate the push rod along the first axis, wherein the rotation of the second handle portion about the first axis is transmitted to the end-effector so that the end-effector rotates about its center axis in consequence of the rotation of second handle portion; and a cuff having a passage therethrough that is configured to hold a wrist or forearm of a user, wherein the cuff is configured to couple to the forearm attachment portion of the tool frame. In some instances, the shuttle body may be completely outside the second handle portion.

The forearm attachment portion and/or the cuff may be configured to permit one or more degrees of freedom between the cuff (which is typically rigidly attached to the user's arm) and the forearm attachment portion. For example, the device may include a joint between the forearm attachment portion of the tool frame and the cuff, wherein the joint is configured to provide one or more rotational degrees of freedom between the cuff and the forearm attachment portion of the tool frame. The joint may be a bearing (e.g., a machine element that constrains the relative motion to one or more desired motions such as pitch, roll and yaw, and may reduce friction between the moving parts). For example, the device may include one or more joints between the forearm attachment portion of the tool frame and the cuff, wherein the one or more joints are configured to provide one or more of a roll degree of freedom with respect to the tool axis, a pitch degree of freedom and a yaw degree of freedom between the cuff and the forearm attachment portion of the tool frame.

In general, the cuff may include a strap and/or securement so that it may be attached securely to the users arm (e.g., forearm); it may be removable from the forearm attachment portion so that it can be attached to the user's forearm, then snapped or otherwise attached to the forearm attachment portion of the tool frame.

In general, the unlimited roll between the second handle portion and the first handle portion may be transmitted to the end-effector. As mentioned, the roll between the second handle portion and the first handle portion may be transmitted by a transmission member that is separate from the tool frame, and may be routed around or through the tool frame. For example, the rotation of the second handle portion may be transmitted to the end-effector through a rotation transmission extending between the second handle portion and the end-effector. Alternatively, in some variation the tool shaft transmits the roll between the second handle portion and the first handle portion; for example, either the second handle portion or the first handle portion may be rigidly connected to the tool shaft so that roll between the second handle portion and the first handle portion is transmitted by the tool frame to the end-effector at the distal end of the apparatus. In general, because the unlimited roll between the second handle portion and the first handle portion is relative between the two, the transmission member for this roll may be connected to either the second handle portion or the first handle portion, although it is illustrated herein primarily as coupled to the second handle portion (e.g., the knob or dial at a distal region of the handle). For example, the rotation of the second handle portion (e.g., the knob or dial) may be transmitted to the end-effector because the elongate tool frame is coupled to the second handle portion so that the elongate tool frame is rotationally constrained relative to the second handle portion and the end-effector is coupled to the elongate tool frame so that the end-effector is rotationally constrained relative to the elongate tool frame.

As mentioned, any of the apparatuses described herein may include an input joint between the handle and the tool frame. For example, any of these apparatuses may include an input joint wherein the input joint provides a pitch degree of freedom between the handle and the tool about a pitch axis of rotation and a yaw degree of freedom between the handle and the tool about a yaw axis of rotation. This input joint may be a parallel kinematic input joint or a serial kinematic input joint or a combination of parallel and serial kinematic input joint. For example, any of these devices may include an input joint between the handle and the tool frame and an output joint between the tool frame and the end-effector, wherein the input joint comprises a pitch motion path and a yaw motion path, further wherein the pitch motion path and the yaw motion path are independent and coupled in parallel (forming a parallel kinematic input joint) between the handle and the tool frame, wherein the pitch motion path encodes pitch motion of the handle relative to the tool frame for transmission to the output joint but does not encode yaw motion of the handle relative to the tool frame for transmission to the output joint, and wherein the yaw motion path encodes yaw motion of the handle relative to the tool frame for transmission to the output joint but does not encode pitch motion of the handle relative to the tool frame for transmission to the output joint. Alternatively, the pitch motion path and the yaw motion path may be arranged in series (as a serial kinematic input joint). However, as will be described herein, any of the devices including an input joint having more than one degree of freedom axis of rotation (e.g., pitch and yaw, pitch and roll, yaw and roll, pitch, yaw and roll, etc.) may be configured so that the two or more axes of rotation intersect at a center or rotation (e.g., a virtual center of rotation) that is positioned behind (proximal to) the handle, including at a virtual center of rotation that would be within the user's wrist when the device is operated by the user. For example, the pitch axis of rotation and the yaw axis of rotation may intersect in a center of rotation that is proximal to the handle.

In any of the variations including an input joint having multiple (e.g., pitch and yaw) degrees of freedom, one or more transmission members may be included to transmit the motion (e.g., pitch motion, yaw motion) to the output joint and therefore the end-effector. For example, a device may include a pitch transmission member and a yaw transmission member extending from the input joint to the output joint, wherein the pitch transmission member transmits pitch rotations and the yaw transmission member transmits yaw rotations of the input joint to corresponding rotations of the output joint.

As mentioned, any appropriate end-effector may be used. The end effector may or may not have grasping jaws (or simply jaws) that may or may not move. For example, the end effector may have a soft end to spread delicate tissues (e.g., dissector) or a camera or a laser pointer. Therefore, end effector assembly or end effector bodies may be referred as end effector jaws, or as jaws or as end effector or the like. The end effector may also have one or more moving jaws, one or more stationary jaws (stationary with respect to moving jaws) and other bodies required for end effector actuation. In some examples, an end-effector may be configured as a jaw assembly that include jaws that open and close. The end-effector control input on the handle may be actuated, e.g., by a user's finger or fingers, including the user's thumb, of the same hand holding the handle. For example, any of these devices may include an end-effector that is configured as a jaw assembly so that the actuation of the end-effector control input opens or closes the jaw assembly. The end-effector control input may be operated to hold the jaws open or closed (e.g., continuing to actuate the end-effector control input). For example, when the end-effector control input is a trigger or lever on the handle, holding the trigger or lever down may hold the jaws closed, whereas releasing the trigger or lever may release/open the jaws.

The end-effector may generally be configured as an assembly having multiple portions that are coupled together to allow relative motion between the parts. For example, the end-effector may include a second end-effector portion that is movably coupled to a first end-effector portion; and the apparatus (e.g., device) may further include a transmission cable connecting the shuttle body to the second end-effector portion so that actuation of the end-effector control input on the handle moves the second end-effector portion relative to the first end-effector portion when the second handle portion is in any rotational position about the first axis relative to the first handle portion. As mentioned, the transmission cable may be a rope or braided material that is compliant in compression, torsion and bending.

The end-effector control input may be any appropriate control, including but not limited to a trigger, lever or button, which is typically positioned on the first handle portion and configured for actuation by one or more of a user's fingers and thumb. This end effector control input may be connected to push rod (H.Body C) via. an input transmission mechanism which takes input of the end effector control input and outputs a translation of the push rod (H.Body C) along a first axis.

For example, a medical device having an unlimited roll handle may include: an elongate tool frame having a forearm attachment portion at a proximal end, the elongate frame having a tool axis; an end-effector at a distal end of the elongate tool frame; a handle that provides unlimited roll to the end-effector, wherein the handle includes: a first handle portion, a second handle portion coupled to the first handle portion so that the second handle portion has one rotational degree of freedom in a first axis relative to the first handle portion but is translationally constrained relative to the first handle portion along the first axis, a push rod within the first handle portion and coupled to the first handle portion so that it has one translational degree of freedom along the first axis relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion, and an end-effector control input on the first handle portion coupled to the push rod and configured to translate the push rod along the first axis, wherein rotation of the second handle portion is transmitted to the end-effector so that the end-effector rotates with the second handle portion; and a cuff having a passage therethrough that is configured to hold a wrist or forearm of a user; and a joint between the forearm attachment portion of the tool frame and the cuff, wherein the joint provide one or more of a roll degree of freedom, a pitch degree of freedom and a yaw degree of freedom between the cuff and the forearm attachment portion of the tool frame, and wherein actuation of the end-effector control input on the handle actuates the end-effector when the second handle portion is in any rotational position about the first axis relative to the first handle portion.

In general, any of these apparatuses may include an unlimited roll handle in which the shuttle body portion of the handle assembly is keyed to the knob/dial portion of the handle (e.g., second handle portion). Thus, the shuttle body may be coupled to the second handle portion so that it has one translational degree of freedom along the first axis relative to the second handle portion but is rotationally constrained about the first axis relative to the second handle portion. As mentioned above, the shuttle includes the structure(s) that couple to the transmission member transmitting the end-effector control input (such as an end-effector actuation transmission) to the end-effector.

Also described herein are apparatuses including an unlimited roll handle in which the apparatus is configured to articulate, e.g., between the handle and the tool shaft, with or without an arm attachment. For example, described herein are medical devices comprising: an end-effector at a distal end of an elongate tool frame; a handle that provides unlimited roll to an end-effector, wherein the handle includes: a first handle portion, a second handle portion coupled to the first handle portion so that the second handle body has one rotational degree of freedom in a first axis relative to the first handle portion but is translationally constrained relative to the first handle portion along the first axis, a push rod within the first handle portion and coupled to the first handle portion so that it has one translational degree of freedom along the first axis relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion but is rotationally constrained about the first axis relative to the second handle portion, and an end-effector control input on the first handle portion coupled to the push rod and configured to translate the push rod along the first axis, wherein rotation of the second handle portion is transmitted to the end-effector so that the end-effector rotates with the second handle portion; and an input joint between the handle and the tool frame configured to encode motion of the handle about a pitch axis of rotation relative to the tool frame for transmission to an output joint, and further configured to encode motion of the handle about a yaw axis of rotation relative to the tool frame for transmission to an output joint, wherein the pitch axis of rotation and the yaw axis of rotation intersect in a center of rotation; wherein the end-effector is coupled to the tool frame by the output joint. Typically, actuation of the end-effector control input on the handle may actuate the end-effector when the second handle portion is in any rotational position relative to the first handle portion.

As mentioned above, the center of rotation may be posterior to the handle, and may be, for example, a virtual center of rotation that would be within a user's arm or wrist when the apparatus is held by a user. Any of these apparatus may also include an arm (e.g., forearm) attachment. For example, any of these apparatuses may include a forearm attachment portion at a proximal end of the tool frame and a cuff having a passage therethrough that is configured to hold a wrist or forearm of a user, wherein the cuff is configured to couple to the forearm attachment portion of the tool frame. The forearm attachment may include a joint between the forearm attachment portion of the tool frame and the cuff, wherein the joint is configured to provide one or more rotational degrees of freedom between the cuff and the forearm attachment portion of the tool frame.

The input joint between the handle and the tool shaft may be referred to herein as a pitch and yaw input joint, and may comprise a pitch motion path and a yaw motion path, as described above. For example, the pitch motion path and the yaw motion path may be independent and coupled in parallel between the handle and the tool frame, wherein the pitch motion path encodes pitch motion of the handle relative to the tool frame for transmission to the output joint but does not encode yaw motion of the handle relative to the tool frame for transmission to the output joint, and wherein the yaw motion path encodes yaw motion of the handle relative to the tool frame for transmission to the output joint but does not encode pitch motion of the handle relative to the tool frame for transmission to the output joint.

For example, a medical device may include: an end-effector at a distal end of an elongate tool frame; a handle that provides unlimited roll to an end-effector, wherein the handle includes: a first handle portion, a second handle portion coupled to the first handle portion so that the second handle body has one rotational degree of freedom in a first axis relative to the first handle portion but is translationally constrained relative to the first handle portion along the first axis, a push rod within the first handle portion and coupled to the first handle portion so that it has one translational degree of freedom along the first axis relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion but is rotationally constrained about the first axis relative to the second handle portion, and an end-effector control input on the first handle portion coupled to the push rod and configured to translate the push rod along the first axis, wherein rotation of the second handle portion is transmitted to the end-effector so that the end-effector rotates with the second handle portion; and an input joint between the handle and the tool frame, the input joint comprising a pitch motion path and a yaw motion path, further wherein the pitch motion path and the yaw motion path are independent and coupled in parallel between the handle and the tool frame, wherein the pitch motion path encodes pitch motion of the handle relative to the tool frame about a pitch axis of rotation for transmission to the output joint but does not encode yaw motion of the handle relative to the tool frame for transmission to the output joint, and wherein the yaw motion path encodes yaw motion of the handle relative to the tool frame about a yaw axis of rotation for transmission to the output joint but does not encode pitch motion of the handle relative to the tool frame for transmission to the output joint, wherein the pitch axis of rotation and the yaw axis of rotation intersect in a center of rotation that is proximal to the handle; wherein the end-effector is coupled to the tool frame by the output joint.

Any of these apparatuses may include an unlimited roll handle and an end-effector configured as a jaw assembly either with or without an arm (e.g., forearm) attachment and/or be configured as an articulating device (e.g., including an input joint such as a pitch and yaw input joint). For example, described herein are medical devices including: an end-effector at a distal end of an elongate tool frame; a handle that provides unlimited roll to an end-effector, wherein the handle includes: a first handle portion, a second handle portion coupled to the first handle portion so that the second handle body has one rotational degree of freedom in a first axis relative to the first handle portion but is translationally constrained relative to the first handle portion along the first axis, a push rod within the first handle portion and coupled to the first handle portion so that it has one translational degree of freedom along the first axis relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion but is rotationally constrained about the first axis relative to the second handle portion, and an end-effector control input on the first handle portion coupled to the push rod and configured to translate the push rod along the first axis, wherein rotation of the second handle portion is transmitted to the end-effector so that the end-effector rotates with the second handle portion; wherein the end-effector includes a first end-effector portion that is movably coupled to a second end-effector portion; and a transmission cable connecting the shuttle body to the second end-effector portion so that actuation of the end-effector control input moves the second end-effector portion relative to the first end-effector portion when the second handle portion is in any rotational position with respect to the first axis relative to the first handle portion. As mentioned, the end-effector may be a jaw assembly configured so that actuation of the end-effector control input opens or closes the jaw assembly. For example, the second end-effector portion may comprise a jaw member that is pivotally hinged to the first end-effector portion. The jaw assembly may include a third end-effector that is pivotally hinged to the first end-effector portion and coupled to the transmission cable so that actuation of the end-effector control input on the handle moves the second and third end-effector portions relative to the first end-effector portion.

As described above, any of these apparatuses may include a forearm attachment portion at a proximal end of the tool frame and a cuff having a passage therethrough that is configured to hold a wrist or forearm of a user, wherein the cuff is configured to couple to the forearm attachment portion of the tool frame; the apparatus may also include a joint between the forearm attachment portion of the tool frame and the cuff, wherein the joint is configured to provide one or more rotational degrees of freedom between the cuff and the forearm attachment portion of the tool frame.

For example, a medical device may include: an end-effector at a distal end of an elongate tool frame; a handle that provides unlimited roll to an end-effector, wherein the handle includes: a first handle portion, a second handle portion coupled to the first handle portion so that the second handle body has one rotational degree of freedom in a first axis relative to the first handle portion but is translationally constrained relative to the first handle portion along the first axis, a push rod within the first handle portion and coupled to the first handle portion so that it has one translational degree of freedom along the first axis relative to the first handle portion but is rotationally constrained about the first axis relative to the first handle portion, a shuttle body within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion but is rotationally constrained about the first axis relative to the second handle portion, and an end-effector control input on the first handle portion coupled to the push rod and configured to translate the push rod along the first axis, wherein rotation of the second handle portion is transmitted to the end-effector so that the end-effector rotates with the second handle portion; wherein the end-effector comprises a jaw assembly including a first end-effector portion that is movably coupled to a second end-effector portion, wherein the second end-effector portion comprises a jaw member; and a transmission cable connecting the shuttle body to the second end-effector portion so that actuation of the end-effector control input moves the second end-effector portion relative to the first end-effector portion when the second handle portion is in any rotational position with respect to the first axis relative to the first handle portion to open or close the jaw assembly of the end-effector.

Described herein are apparatuses (e.g., mechanisms, devices, tools, machines, systems, etc.) including handles with an unlimited roll mechanism which may incorporate certain degrees of freedoms and degrees of constraints between bodies in the handle assembly and/or in the end effector assembly, such that there is an efficient transmission of articulation (pitch/yaw), roll as well as end effector actuation. This apparatuses may also incorporate certain degrees of freedoms and degrees of constraints between bodies in the handle assembly and/or in the end effector assembly by utilizing independent transmission members. These transmission members may be end effector articulation transmission member(s), end effector roll transmission member(s) and/or end effector actuation transmission member. These transmission members may be independent or two or more independent transmission members may be combined to act like a single transmission member if it helps with efficient transmission of various functionalities.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 3I shows (from left to right) a thrust needle bearing, a thrust roller bearing, a roller bearing and an angular contact roller bearing, each of which may be used as part of an unlimited roll handle assembly.

DETAILED DESCRIPTION

Described herein are apparatuses including an unlimited roll handle assembly. Although the unlimited roll handle assemblies described herein may be incorporated into any apparatus (e.g., device, tool, system, machine, etc.), described herein in particular are apparatuses including unlimited roll handles assemblies at a proximal region of an elongate tool frame (e.g., a tool shaft or including a tool shaft) having an end-effector at the distal end of the tool frame. The apparatus may include a forearm attachment at the proximal end; the forearm attachment may allow one or more degrees of freedom between the user's forearm and the tool frame while the user's hand grips the unlimited roll handle assembly. The apparatus may be articulating; for example, the tool frame may include an input joint between the unlimited roll handle assembly and the tool frame that may encode movement (e.g., pitch and yaw movements) between the handle and the tool frame for transmission to an output joint between the tool frame and an end-effector, so that the end-effector may be moved as the handle is moved. Although any appropriate end-effector may be used, in some variations the end-effector is a jaw assembly that includes at least a pair of jaws (end-effector portions), which move to open and close the jaws when actuated by an end-effector control input on the handle of the device.

In general, the unlimited roll handle assemblies described herein may be configured to have four (through in some cases only three) or more parts interact together to provide unlimited rotation of a knob or dial portion of the handle assembly about a central axis relative to palm grip portion of the handle, while still permitting actuating of an end-effector control input to actuate the end-effector from any rotational position of the dial relative to the palm grip. Rotation of the knob or dial portion of the apparatus causes rotation of the end-effector, and in some cases rotation of the tool frame.

Figure 1:
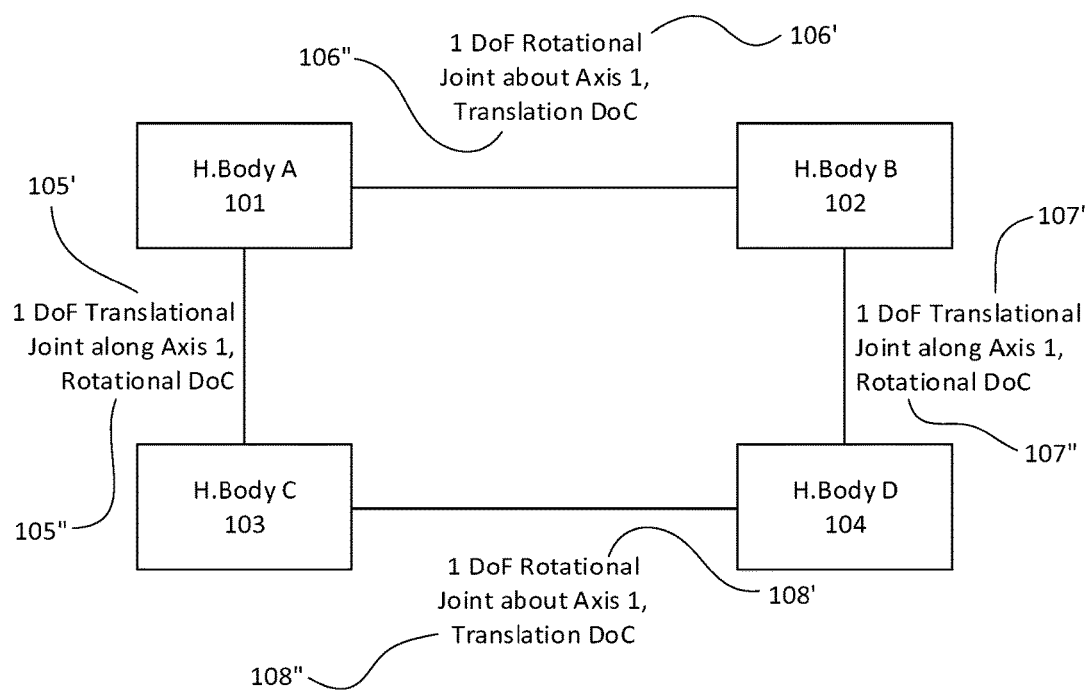
FIG. 1 is a constraint map of an unlimited roll handle (handle assembly) having four parts, illustrating the degrees of freedom and degrees of constraint between the coupled components.

A constraint map of an unlimited roll handle assembly is shown in FIG. 1, illustrating a conceptual model of the relative degrees of freedom (DoF) and degrees of constraint (DoC) between component portions of an unlimited roll handle rotation mechanism. The rotation mechanism typically comprises rigid bodies that are generically referred to as: H.Body A 101, H.Body B 102, H.Body C 103, and H.Body D 104. H.Body A may be referred to as the reference ground, in that the motion of all other bodies may be described with respect to H.Body A. For example, H.Body A may be a palm grip. In general, any other of these bodies may be used as the ground reference for describing the motion of the remaining bodies.

Using H.Body A as the ground reference, H.Body C has a single translational degree of freedom (DoF) with respect to H.Body A along a first axis (e.g., axis 1) and has rotational constraint with respect to H.Body A about axis 1 105. This implies that relative translation along Axis 1 is allowed between H.Body C and H.Body A. However, relative rotation about Axis 1 is not allowed between the two, and therefore transmitted from one to the other and vice versa. H.Body B has a rotational DoF with respect to H.Body A about axis 1 and has translational constraint with respect to body A along axis 1 106. H.Body D has single translational DoF with respect to H.Body B along axis 1 and rotational DoF constraint with respect to H.Body B about axis 1 107. H.Body D has rotational DoF with respect to H.Body C about axis 1 and translational constraint with respect to H.Body C along axis 1 108.

Figure 2:
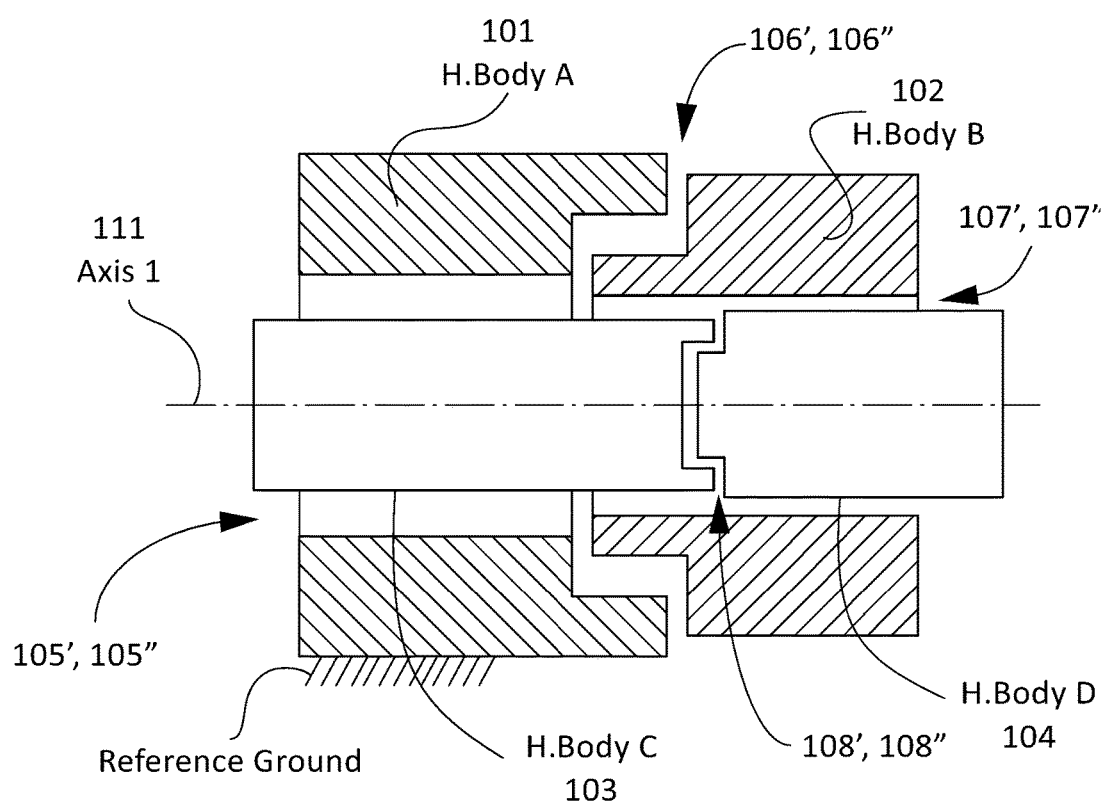
FIG. 2 is a schematic of a conceptual model of an unlimited roll handle illustrating the attributes of each interface of four bodies forming the handle assembly.

FIG. 2 illustrates one example of an unlimited roll handle assembly fitting the constraint map shown in FIG. 1. Even though FIG. 2 shows H.Body A and H.Body B to be cylindrical in shape, the schematic diagram of FIG. 2 does not depict the actual geometric features of each bodies, and these bodies can be of any general shapes as long as they satisfy the joint conditions/constraints between the various bodies as mentioned above.

The constraint map of FIG. 1 results in the following functionality of the rotation mechanism shown: using H.Body A as a reference (i.e., assuming it to be stationary), this mechanism allows for the independent rotation of H.Body B with respect to H.Body A about Axis 1 111. While this happens, H.Body D rotates along with H.Body B, also about Axis 1 and since rotation of H.Body C is coupled to rotation of H.Body A, H.Body C does not rotate. At the same time, any axial translation of the non-rotating H.Body C with respect to the stationary H.Body A along Axis 1 is transmitted to H.Body D, even as H.Body B and H.Body D rotate about Axis 1.

The joints within the rotation mechanism between the bodies that are constraining typically comprise interfacing geometries which prevent rotation or translation with respect to one another. For those joints which enable rotation of one body with respect to another, this joint may be comprised of one or more cylindrical surfaces, and these surfaces can be enabled by a bearing, bushing, or lubricious surface treatment which minimizes frictional resistances. For translating joints, these surfaces may also comprise a lubricious surface treatment. As an overall mechanism, reduced frictional resistances to both translation and rotation mean that simultaneous motion of H.Body D can occur in both rotation and translation as H.Body C only translates and H.Body B only rotates. Thus, another way of describing the functionality of this constraint map is that H.Body D inherits the translation of H.Body C and the rotation of H.Body B. Considering this in reverse: H.Body D has two DoF with respect to H.Body A, translation about Axis 1 and rotation about Axis 1. Any arbitrary combination of these two rotations gets separated into translation only at H.Body C and rotation only at H.Body B.

Any of the joints described herein may be encoded for transmission to an output (e.g., output joint). The encoding may be done mechanically, electrically, or otherwise. For example, sensors may be positioned at these two bodies, e.g., a linear displacement sensor on H.Body C and a rotary sensor on H.Body B may give discrete/individual values for arbitrary combination of rotation and translation applied at H.Body D. These electrical signals could then be transmitted via wired or wireless means to a mechatronic, robotic, electronic, or computer-controlled system. Alternatively, instead of sensors, one could place actuators at these locations, e.g., a linear translational actuator between H.Body A and H.Body C and a rotary actuator between H.Body A and H.Body B. Any arbitrary discrete/individual motion inputs at these two bodies get added into a combined motion at H.Body D with respect to H.Body A. In general, the encoding of movements at any of the joints described herein may be mechanically encoded, such as described below for an input joint encoding pitch and yaw by operating a pair of transmission strips coupled to pulleys to separately and mechanically encode pitch and yaw motions. However, other encoding techniques (electrical, optical, etc.) may alternatively or additionally be used.

In general, the degrees of freedom (DoF) imply that particular motion is allowed. Degrees of constraint (DoC) imply that particular motion is constrained, and therefore transmitted. All motions in FIG. 1 defined with respect to Axis 1, which is the axis of rotation of the handle dial with respect to the handle. Any motion direction not explicitly mentioned could be a DoF or DoC.

Figure 3A:
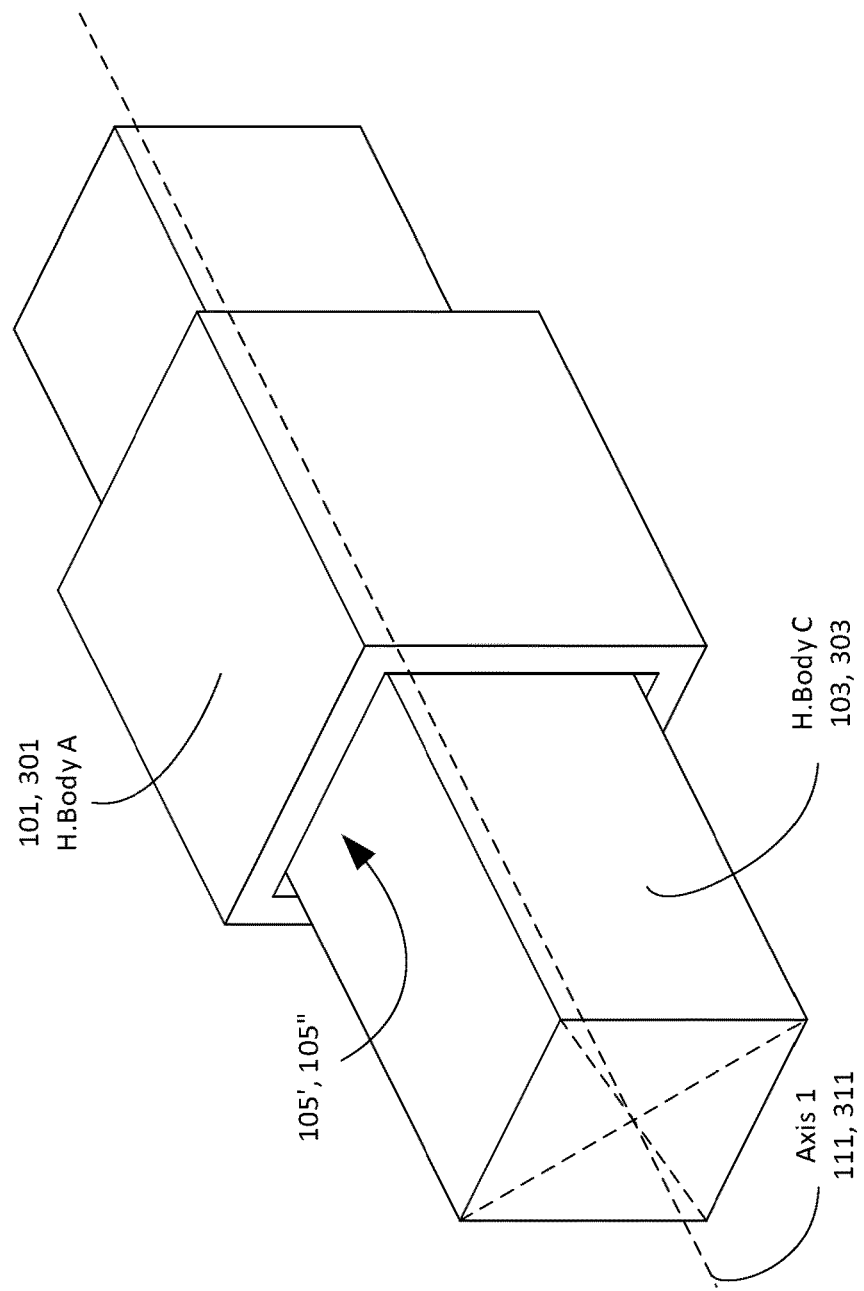
FIG. 3A shows an example of an interface between two bodies of an exemplary unlimited roll handle assembly (e.g., H.Body A and H.Body C) shown as a square slot and square key feature.

In FIG. 1, H.Body C is shown having a single translational DoF along axis 1 with respect to H.Body A and vice versa. H.Body C also has a rotational constraint along axis 1 with respect to H.Body A and vice versa. This type of joint, between bodies A and C, can be accomplished through a variety of embodiments. In one embodiment, the interfacing bodies have a keying feature between them which restricts (e.g., biases) rotation about axis 1 and simultaneously allows for translation along axis 1. FIG. 3A schematically describes a joint which might occur between H.Body A and H.Body C. Referring to FIG. 3A, an outer body with a square longitudinal slot may refer to H.Body A 301 while the inner square key may refer to H.Body C 303. Considering that H.Body A is fixed to reference ground, H.Body C will be allowed to translate about axis 1 311 while unable to rotate about axis 1 due to the interferences posed by square cross-sectional joint. One might consider that this joint can also have a rectangular cross-section which can provide the same single axis (axis 1) rotational constraint and single axis (axis 1) translational DoF.

A functional aspect of this joint is a low friction relative sliding motion along axis 1 between H.Body A and H.Body C. To achieve this, the surface contact between both bodies (H.Body A and H.Body C) need to be minimal so as to avoid large frictional contact between surfaces of H.Body A and H.Body C. Therefore, one way of achieving the same joint between H.Body A and H.Body C with less friction contact is to minimize the contact surface area between two bodies.

Figure 3B:
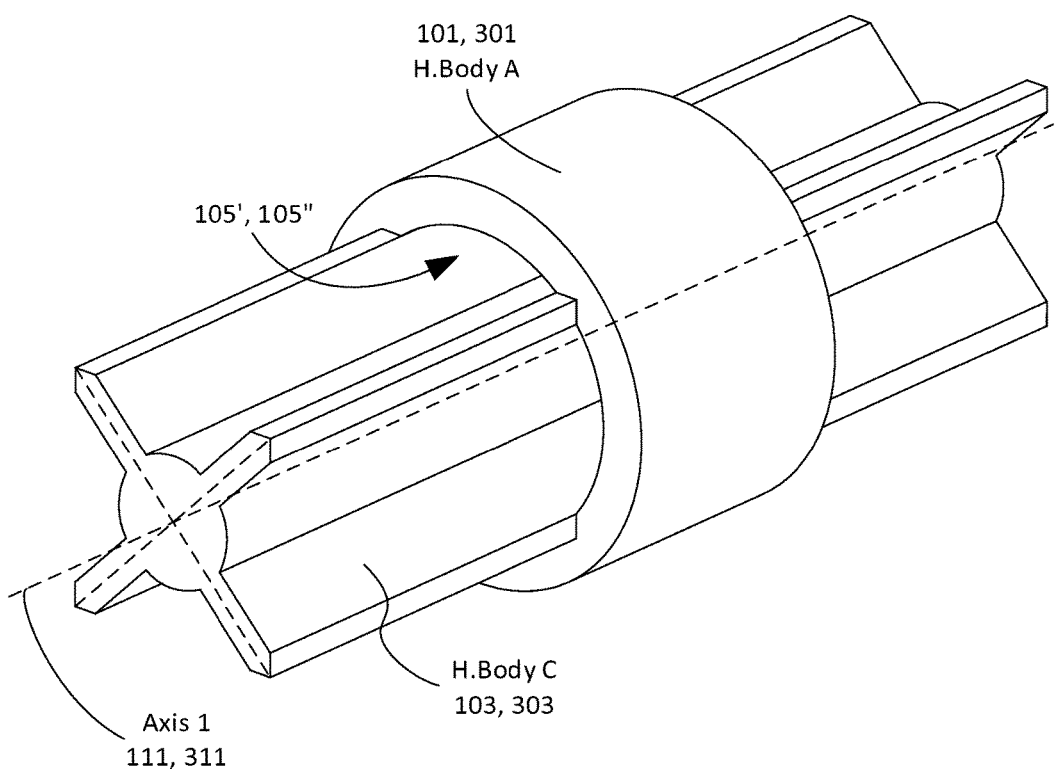
FIG. 3B shows an example of an interface between two bodies of an exemplary unlimited roll handle assembly (e.g., H.Body A and H. Body C) with minimal keying surface between bodies causing a rotational constraint.

FIG. 3B shows one way to reduce the surface contact between H.Body A 301 and H.Body C 303 by interfacing the spokes shown in FIG. 3B of H.Body C with slot cut out in H.Body A.

Figure 3C:
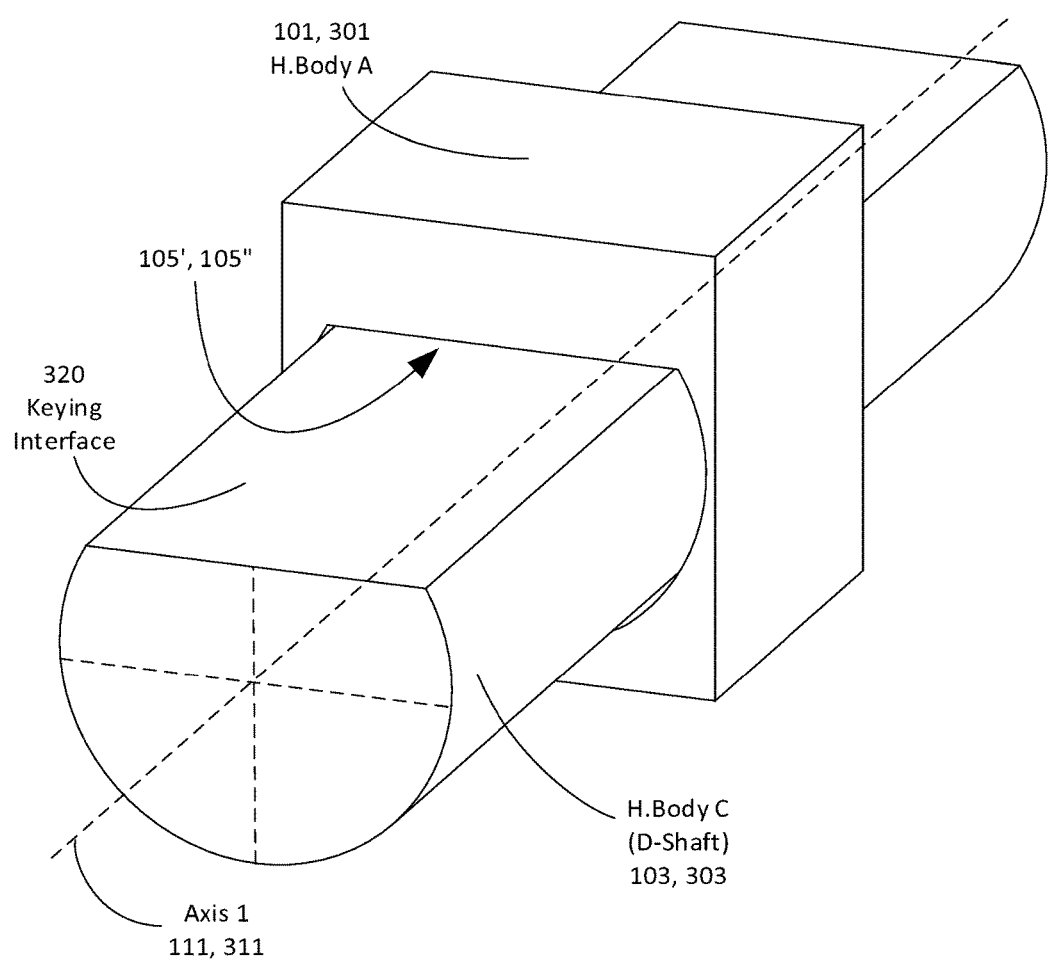
FIG. 3C is an example of an interface between two bodies of an exemplary unlimited roll handle assembly (e.g., H.Body A and H. Body C) shown as a D-Shaft and corresponding slot feature.

FIGS. 3A and 3B show examples of achieving the constraint and DoF between H.Body A 301 and H.Body C 303 but, they can have different geometric shapes such that the constraints and DoFs are met. For example, FIG. 3C shows one way this joint can be achieved by essentially providing the keying surface 320 via the flat end of the D-Shaft 303 (H.Body C) and the slot present in H.Body A 301.

H.Body B 302 and H.Body D 304 have a rotational constraint about axis 1 311 and single translational DoF along axis 1 311. This is the same constraint and DoF that is present between H.Body A 301 and H.Body C 303. Therefore, each one of the ways to attain the joint between H.Body A and H.Body C are also applicable to the joint between H.Body B and H.Body D; given the constraint and DoF requirements are fulfilled.

Any of the Joints between H.Body A and H.Body C as well as between H.Body B and H.Body D may include or require a low friction surface contact between the bodies. This, along with rotational constraint about axis 1 and single translational DoF along axis 1, may completely define the joint between these bodies. Similarly, a constraint, a DoF and functional requirements define the joint between H.Body A and H.Body B as well as between H.Body C and H.Body D. H.Body A and H.Body B may have a single rotational DoF about axis 1 relative to each other and translational constraint along axis 1. H.Body A and H.Body B may also have a functional requirement of providing low friction joint between them while they rotate relative to each other about axis 1. This functional requirement comes from the fact that either of the duo, H.Body A and H.Body B or H.Body C and H.Body D can be under compressive or tensile loading while fulfill the rotational DoF about axis 1 and translational constraint along axis 1.

Figure 3D:
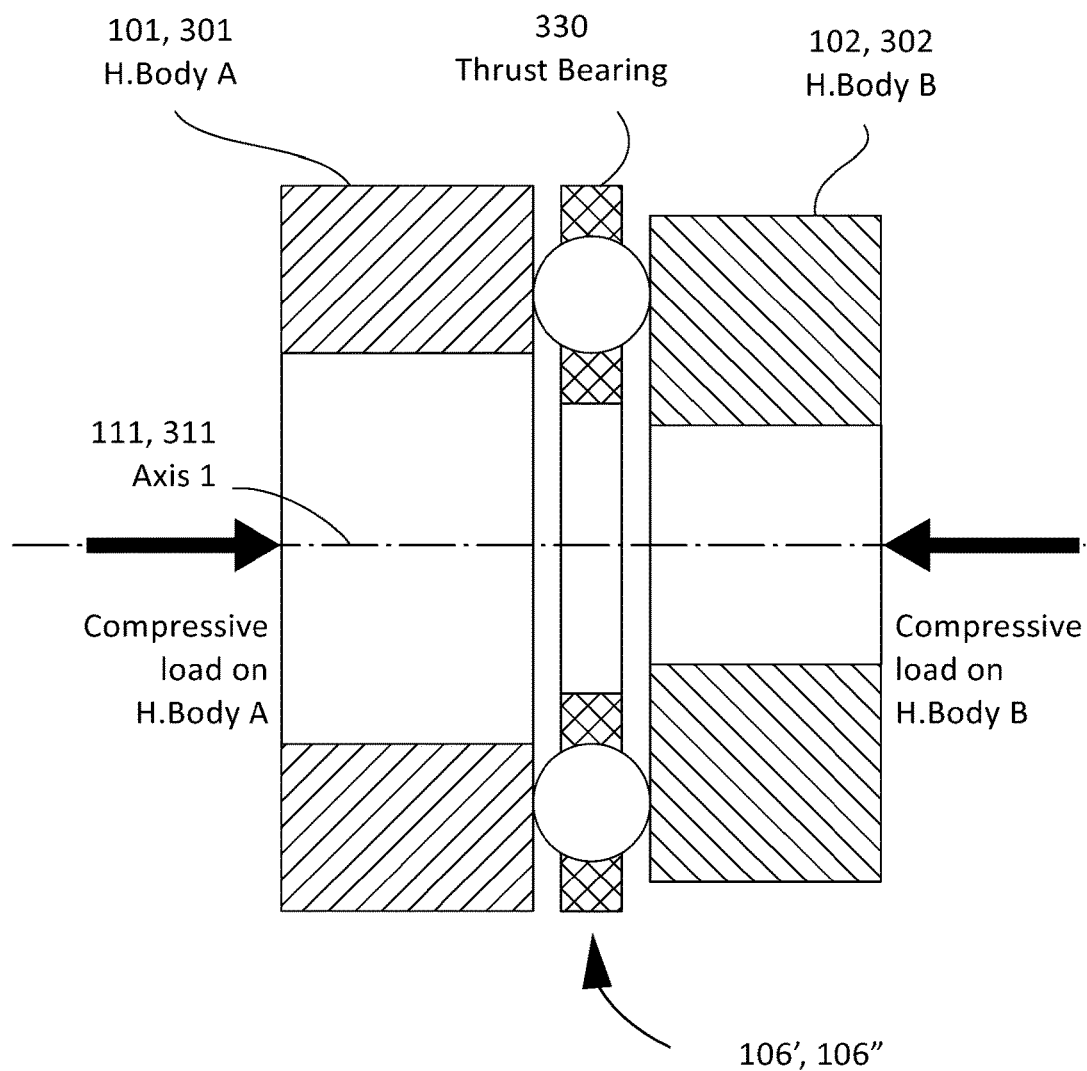
FIG. 3D is an example of a thrust bearing acting as interface between two bodies of an unlimited roll handle assembly (e.g., H.Body A and H.Body B).
Figure 3E:
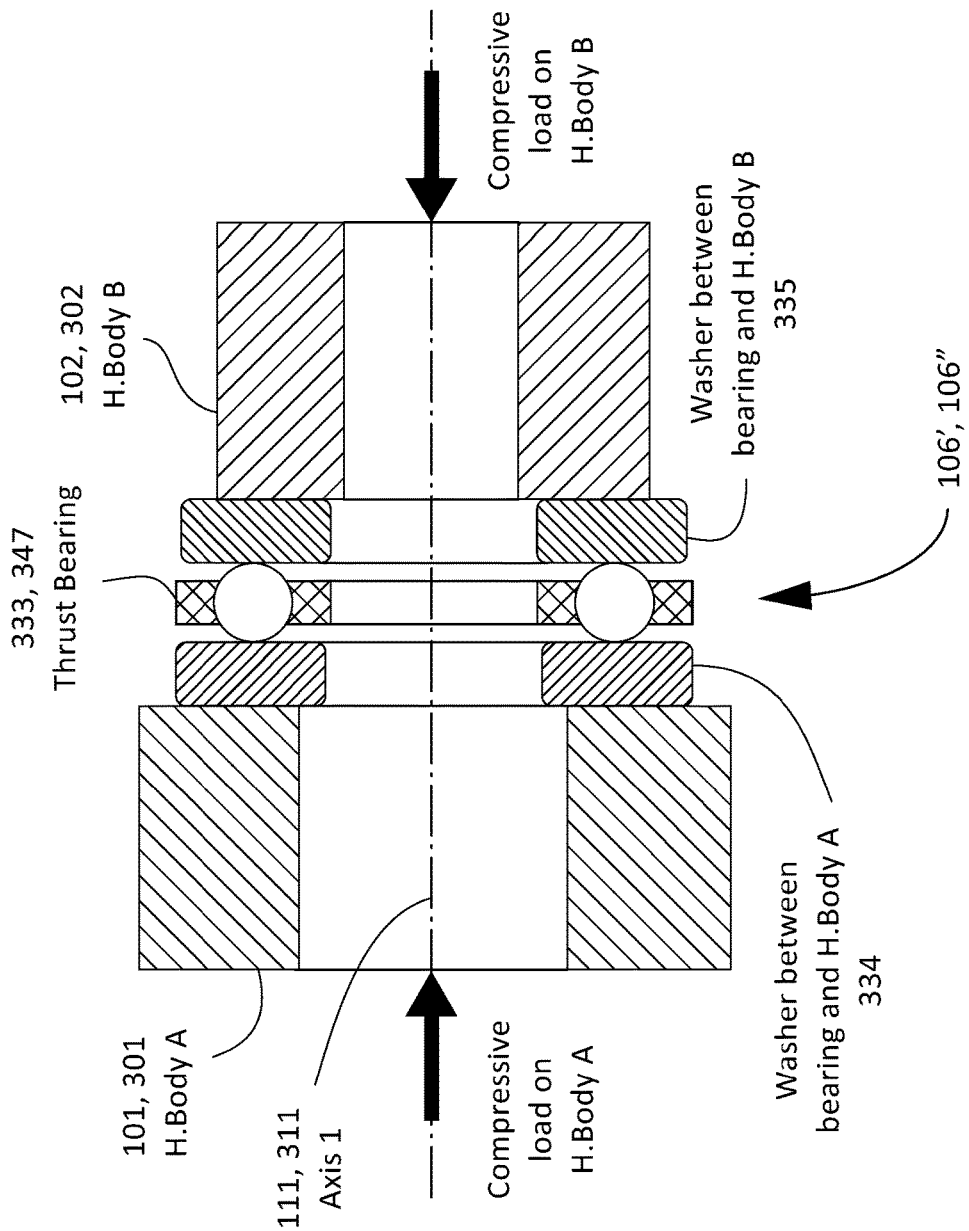
FIG. 3E shows an example of a portion of an unlimited roll handle assembly including a thrust bearing with side washers acting as interface between H.Body A and H.Body B.
Figure 3F:
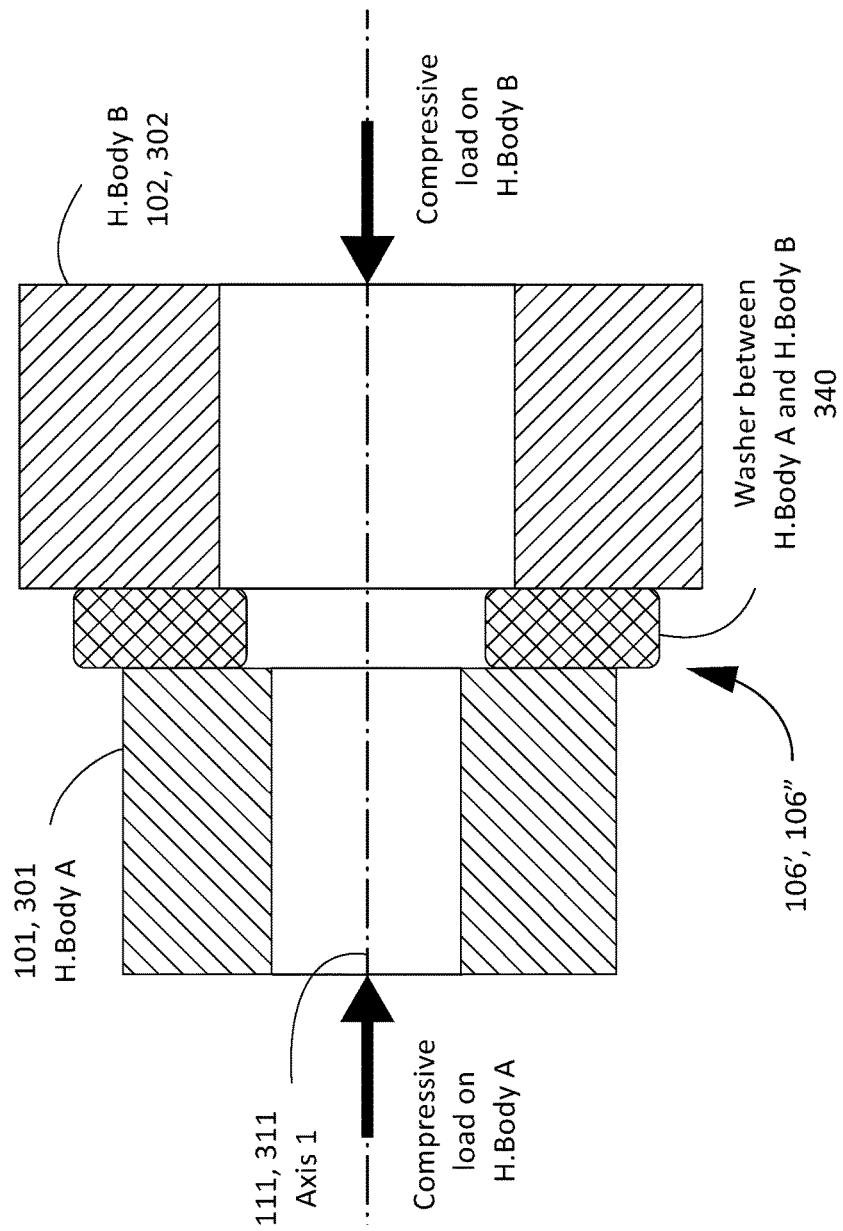
FIG. 3F shows an example of a washer acting as interface between H.Body A and H.Body B in one example of an unlimited roll handle assembly.
Figure 3G:
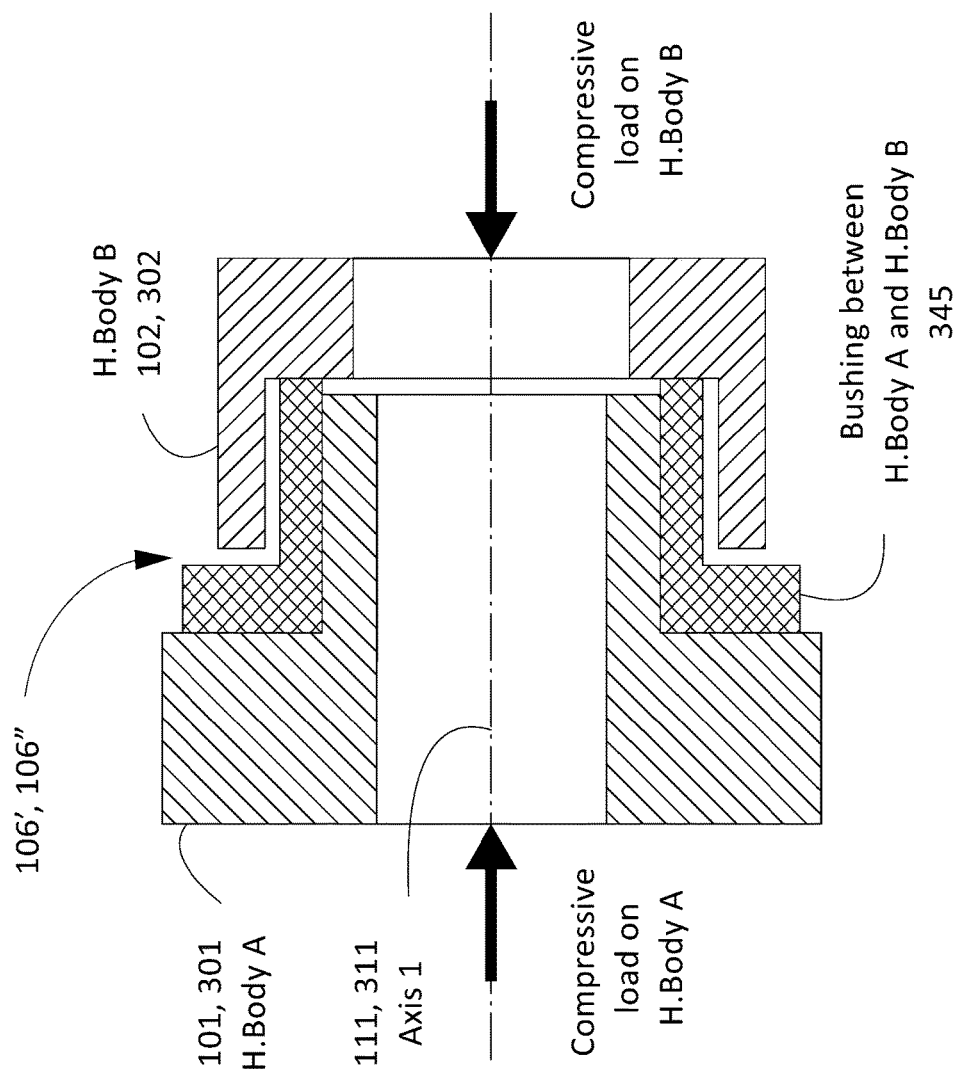
FIG. 3G shows a bushing acting as interface between an H.Body A and H.Body B of an unlimited roll handle assembly.

For example, if H.Body A and H.Body B are placed such that their surfaces normal to axis 1 are under compression, they need to overcome the normal forces acting on each bodies' surfaces so as to provide rotational DoF about axis 1. Therefore, to provide rotational DoF about axis 1 and translational constraint along axis 1, the surfaces of H.Body A and H.Body B may need to provide low friction contact such that the bodies can rotate relative to each other about axis 1. FIG. 3D shows one way of obtaining the desired DoF and constraint by providing low friction surface contact. In this example, a thrust bearing 330 is used to provide the rotational DoF along with maintaining low friction contact between surfaces of H.Body A 301 and H.Body B 302 by holding the thrust load between the two bodies. Similarly, in many ways, this functionality can be achieved by fulfilling the DoF and constraint requirement. For example, an angular contact ball bearing which can hold the thrust load or a roller ball bearing capable to hold the required thrust load can also be used between H.Body A and H.Body B or bushing between two bodies can be used to provide radial support as well as capacity to bear thrust load. Other ways in which the thrust load can be supported is by having a thrust bearing 333 between H.Body A and H.Body B along with washers 334, 335 on each side of the bearing 333. This is shown in FIG. 3E. A single washer 340 between H.Body A 301 and H.Body B 302 made of material with low friction coefficient like Teflon (PTFE), nylon, etc. can also serve the purpose for bearing the thrust load and providing the rotational DoF about axis 1 311. This is shown in FIG. 3F. Also, FIG. 3G shows a bushing 345 placed between the interfacing surfaces of H.Body A 301 and H.Body B 302 such that it is capable to holding thrust load and provide translational constraint along axis 1.

Figure 3H:
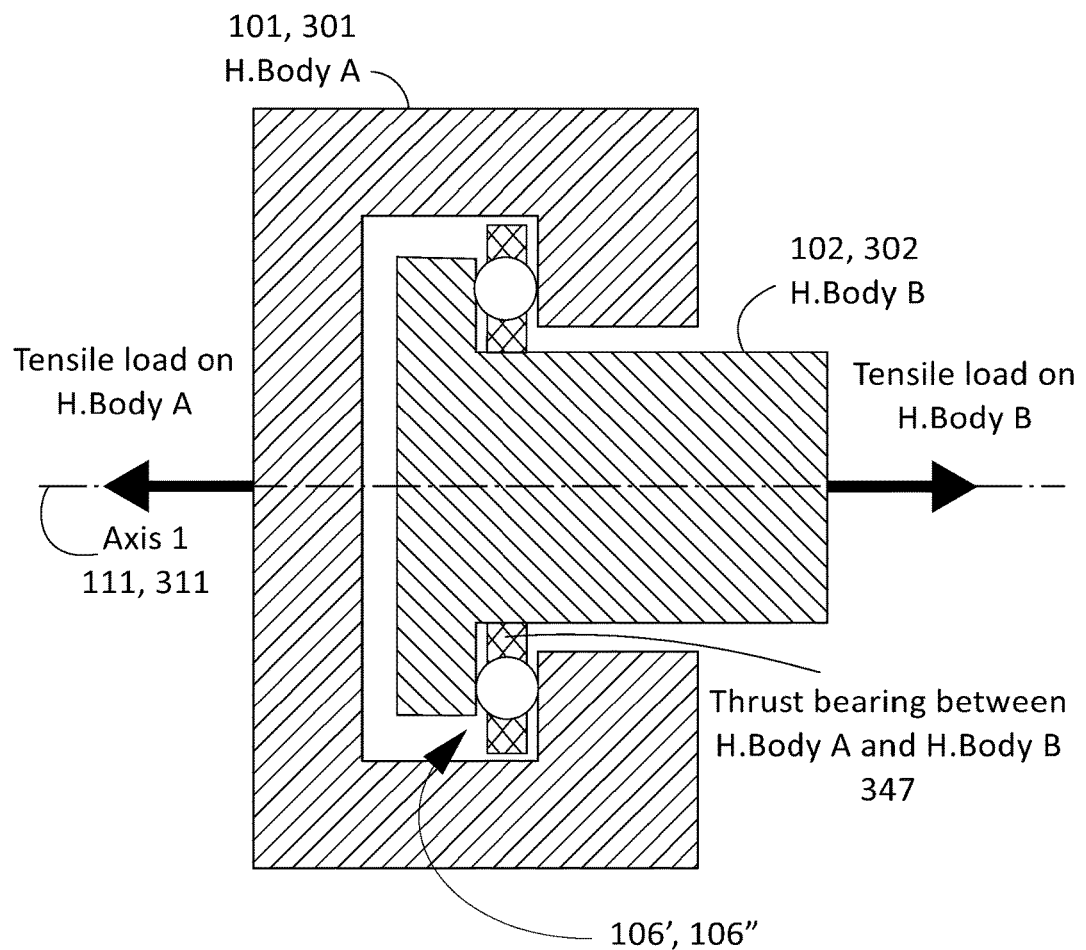
FIG. 3H illustrates an exemplary H.Body A and H.Body B under tensile load with thrust bearing acting as interface between them as part of an unlimited roll (e.g., roll) handle assembly.

The same system of two bodies with an intermediate member carrying thrust load and providing rotational DoF about axis 1 311 and translational constraint along axis 1 311, shown in FIGS. 3D, 3E, and 3F also works well when there is a tensile load as opposed to compressive load on H.Body A and H.Body B. This is depicted in FIG. 3H with a case similar to FIG. 3D where a thrust bearing 347 resides between H.Body A 301 and H.Body B 302, facing normal to axis 1 311. The bearing lying between H.Body A 301 and H.Body B 302 can be of different types, e.g., thrust needle bearing, thrust roller bearing, roller bearing, tapered roller bearing, angular contact bearing, etc. Some types are presented in FIG. 3I, for example, FIG. 3H shows a thrust roller bearing 347 acting as joint between H.Body A 301 and H.Body B 302. Also, H.Body A and H.Body B may have the same joint as H.Body C 303 and H.Body D 304 and comply with all the aforementioned joint types mentioned in this section.

Figure 3J:
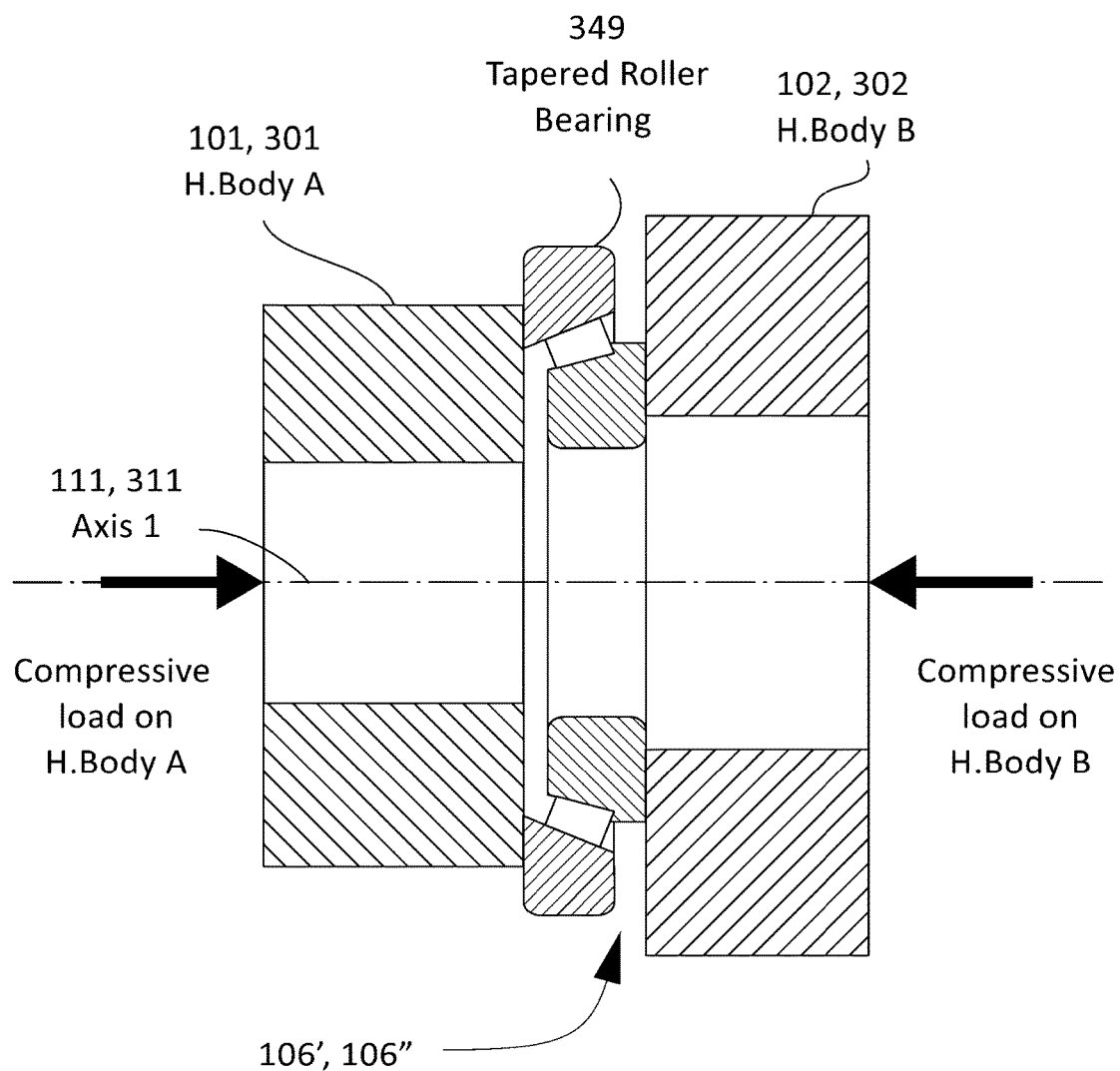
FIG. 3J illustrates an example of a tapered roller bearing that may be used as part of an unlimited roll handle assembly.
Figure 3K:
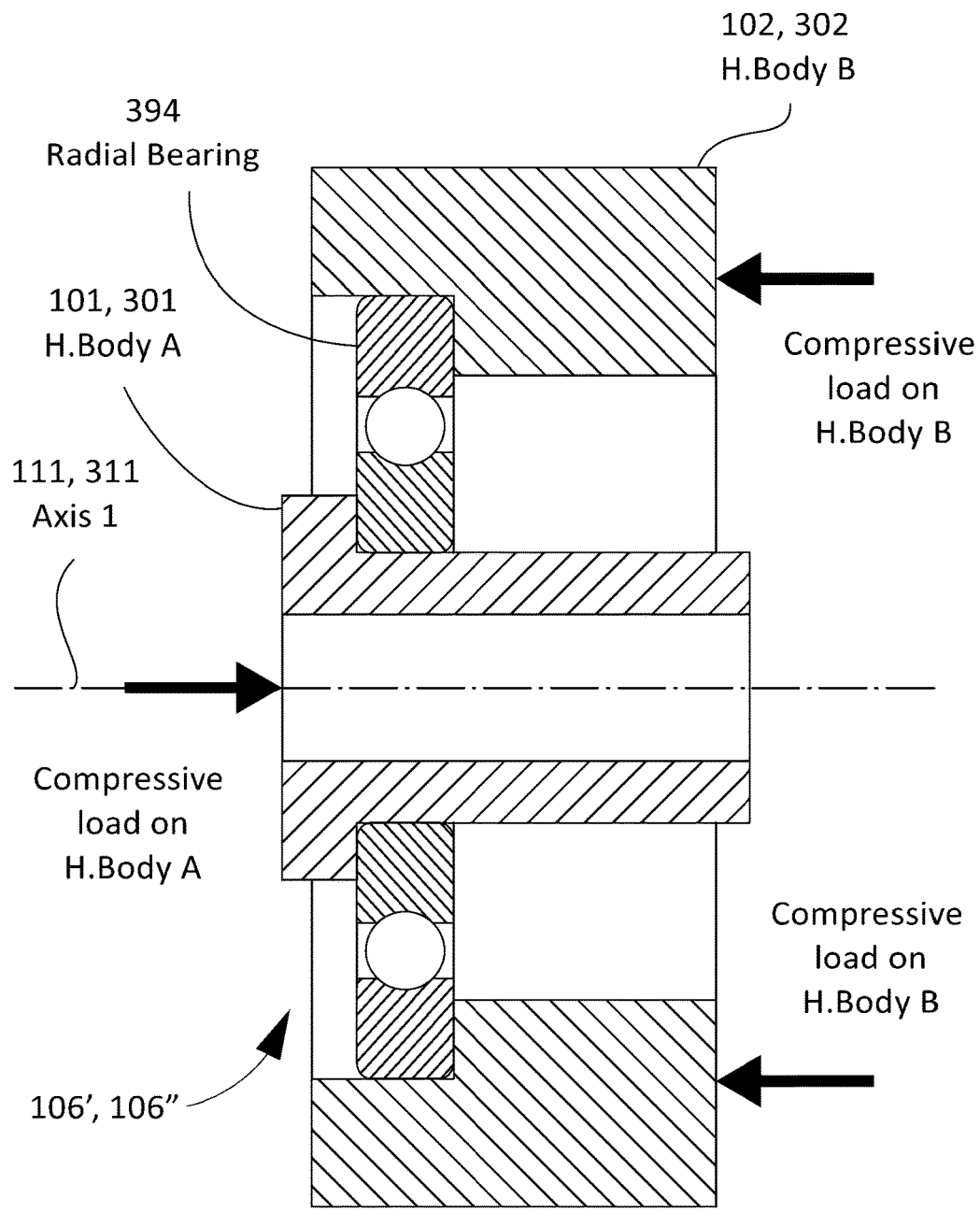
FIG. 3K shows a radial bearing that may be used as part of an unlimited roll handle assembly.

In addition to thrust bearings, one can also employ tapered roller bearings 349, radial ball bearings, etc. One may also employ a combination of these bearings. Some examples are shown in FIGS. 3J and 3K.

Therefore, H.Body A 301 and H.Body B 302 can be under compressive or tensile load along axis 1. Similarly, H.Body C 303 and H.Body D 304 can also be under compressive or tensile load along axis 1. This gives 2 combinations for the whole system presented with schematic diagram in FIG. 1 to be under tensile or compressive loads. Either of the system of two bodies, H.Body A 301 and H.Body B 302 or H.Body C 303 and H.Body D 304 can be under tensile or compressive load. As presented in FIG. 1, H.Body A may serve as the reference ground. Therefore, H.Body B can be under tension or under compression with respect to H.Body A. Whereas, H.Body C is free to move along axis 1 with respect to H.Body A and has rotational constraint about axis 1 with respect to H.Body A. H.Body C can be under compression or tension with respect to H.Body D. Where, H.Body D is free to translate along axis 1 with respect to H.Body B and has rotational constraint about axis 1 with respect to H.Body B. One such combination where H.Body B is under compressive load with respect to H.Body A and H.Body C is under tensile load with respect to H.Body D is show in FIG. 3L. In this example, an angular contact bearing 351 between H.Body A 301 and H.Body B 302 is used. This accounts as a joint between H.Body A 301 and H.Body B 302 which accomplishes the constraint and DoF requirement mentioned above along with the functional requirement of providing low friction surface contact. Similarly, a thrust bearing between H.Body C 303 and H.Body D 304 may be used. This accounts as a joint between H.Body C 303 and H.Body D 304 which accomplishes the constraint and DoF requirement mentioned above, along with the functional requirement of providing low friction surface contact.

In some of these examples, even though the bodies are depicted to be cylindrical in shape, the constraint map (FIG. 1) doesn't imply any restriction on geometric shapes of these bodies as far as the functionality, DoFs and constraints are met.

Figure 3L:
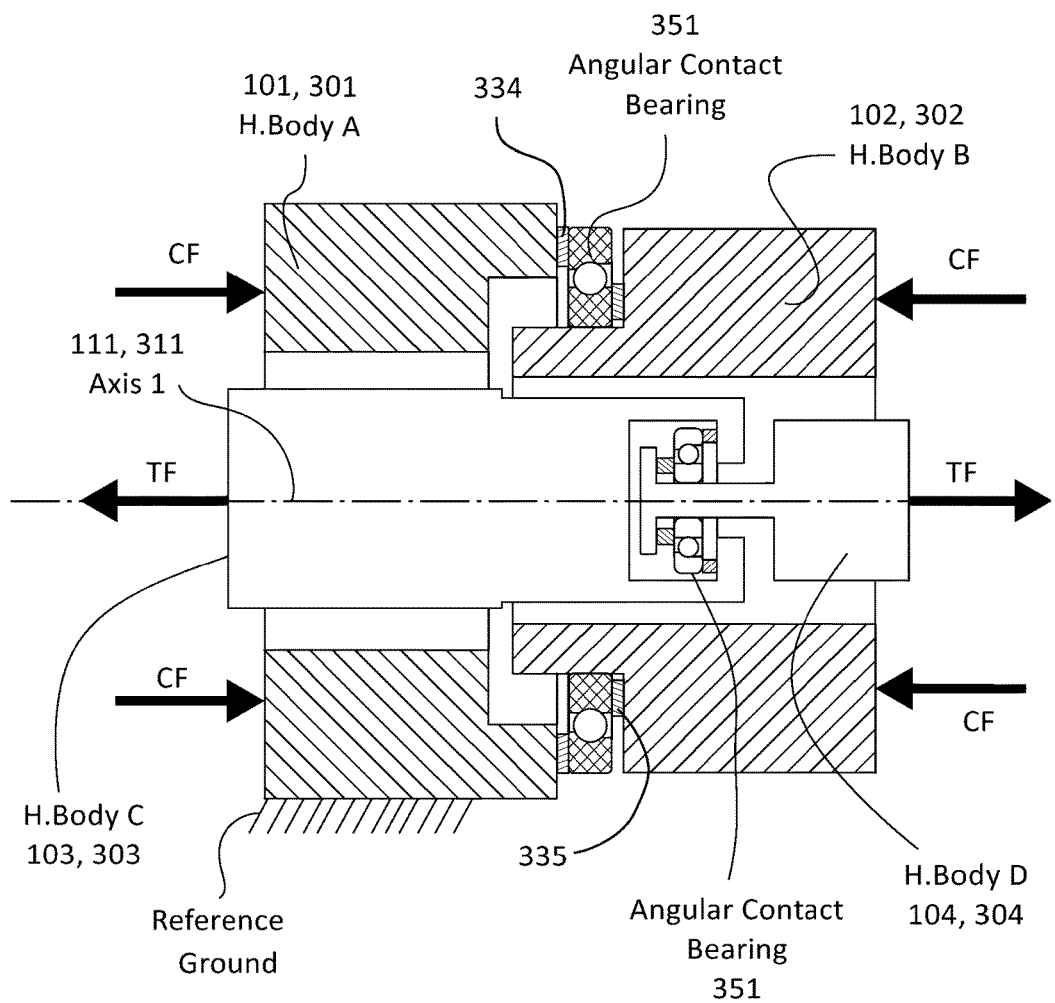
FIG. 3L illustrates exemplary loading conditions applied on different bodies of an unlimited roll handle assembly.
Figure 4A:
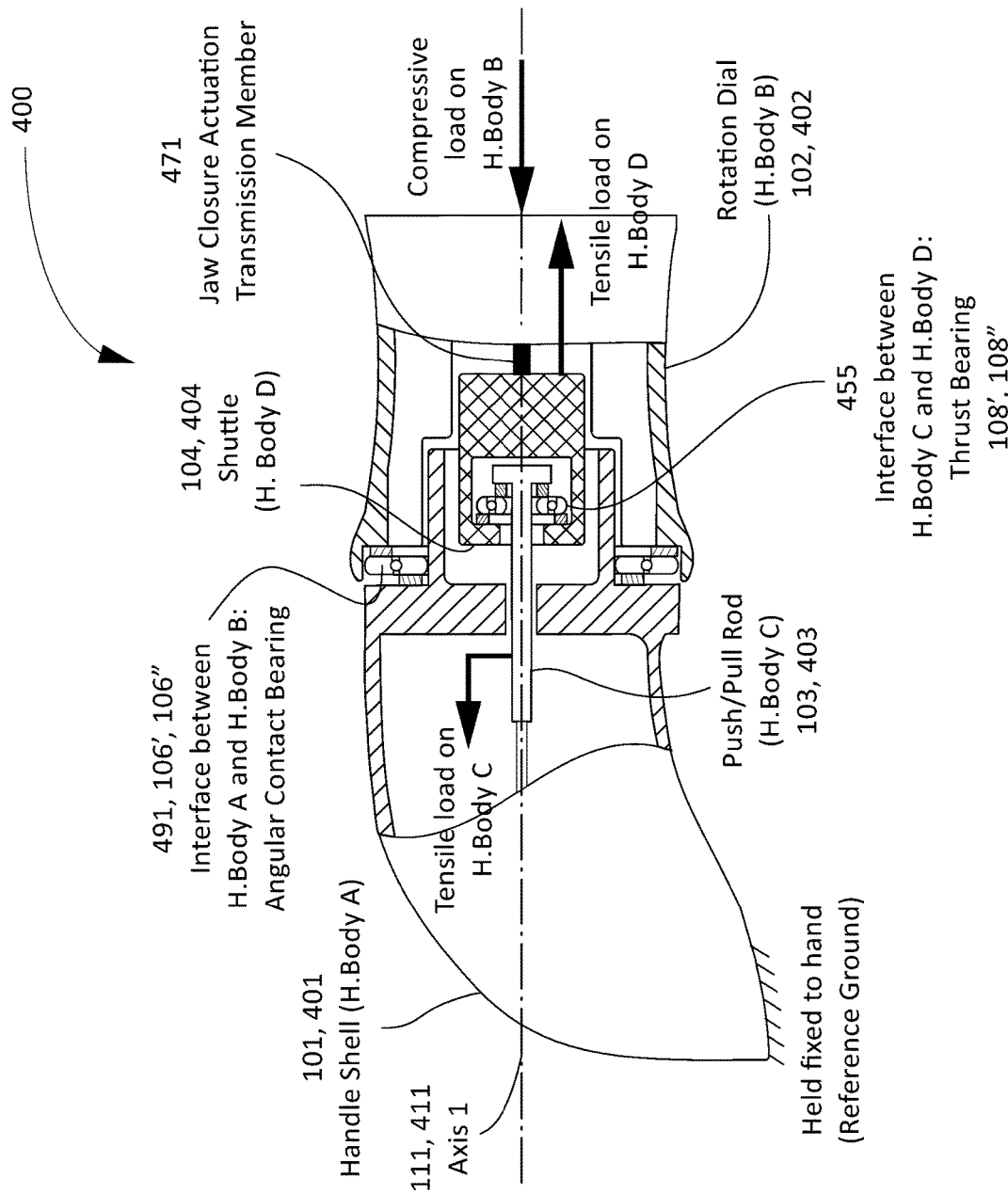
FIG. 4A shows an example of an unlimited ("infinity") handle as described herein, which is one realization of the constraint map shown in FIG. 1 as an ergonomic handle.
Figure 4B:
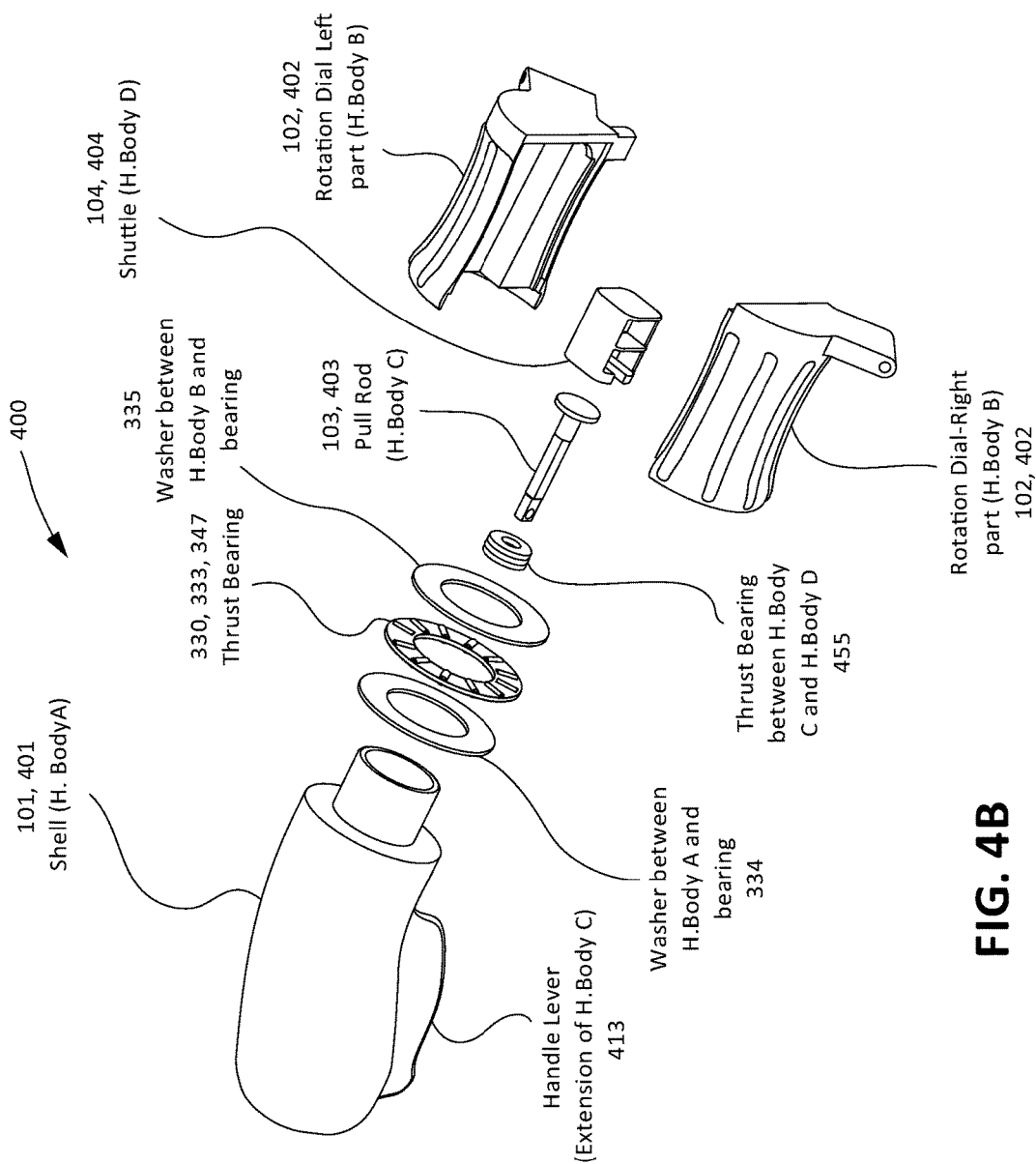
FIG. 4B is an exploded view of the unlimited roll handle assembly of FIG. 4A, in which the first handle portion is configured as a palm grip (H.Body A), the second handle portion is configured as a dial (H.Body B), the push rod (H.Body C) is within the palm grip, and a shuttle (H.Body D) is within the second handle portion. An end-effector control input (e.g., handle lever) may be attached to the palm grip to actuate the end-effector.

FIGS. 4A and 4B show an example of an ergonomic handle assembly (unlimited rotation handle assembly) that utilizes the mechanism described in FIG. 3L involving compressive and tensile loading conditions. This handle is an embodiment of the constraint map shown in FIG. 1. The rotation dial (H.Body B 402) is under translational constraint about axis 1 411 with respect to Handle Body Shell (H.Body A 401). The rotation dial transmits this rotation about axis 1 411 to H.Body D 404, which is referred as shuttle 404. This is possible because shuttle (H.Body D) is under rotational constraint about axis 1 411 with respect to rotation dial (H.Body B 402) and therefore, has no relative rotation about axis 1. The shuttle (H.Body D 404) is further interfaced with H.Body C 403 (referred as push rod or pull rod) via a joint which allows translational DoF along axis 1 and rotational constraint about axis 1. The translation of shuttle (H.Body D) along axis 1 is further transmitted to the moving jaw in the end-effector via the jaw closure transmission member. An end-effector transmission 455 may alternatively be referred to (e.g., when the end-effector is configured as a jaw) as a jaw closure transmission member 455 or jaw closure actuation transmission member to describe the same transmission member; in some variation it may simply be referred to as a transmission cable (when it is a compliant cable, for example). This jaw closure actuation transmission member 471 can be either rigid or non-rigid body or a combination of a rigid and non-rigid members. For example, the transmission member can be the shaft of an apparatus (e.g., of a laparoscopic instrument) or a rod passing internally through the shaft or can be a cable under tension that connects to the end-effector at the distal end of the laparoscopic instrument or it can be combination of a non-rigid and a rigid body (a rod along with a cable under tension). The push/pull rod (H.Body C 401) and shuttle (H.Body D 404) are under tensile load and the rotation dial (H.Body B) is under compressive load and does not translate along axis 1 411 with respect to handle shell (H.Body A) 401.

Another variation of an ergonomic handle assembly shown in FIGS. 4A and 4B can be constructed via a flexure-based design, also known as a compliant mechanism, that realizes the constraint map of FIG. 1 by employing compliant or flexure joints between the bodies H.Body A, H.Body B, H.Body C, and H.Body D to achieve the necessary constraints.

Figure 5:
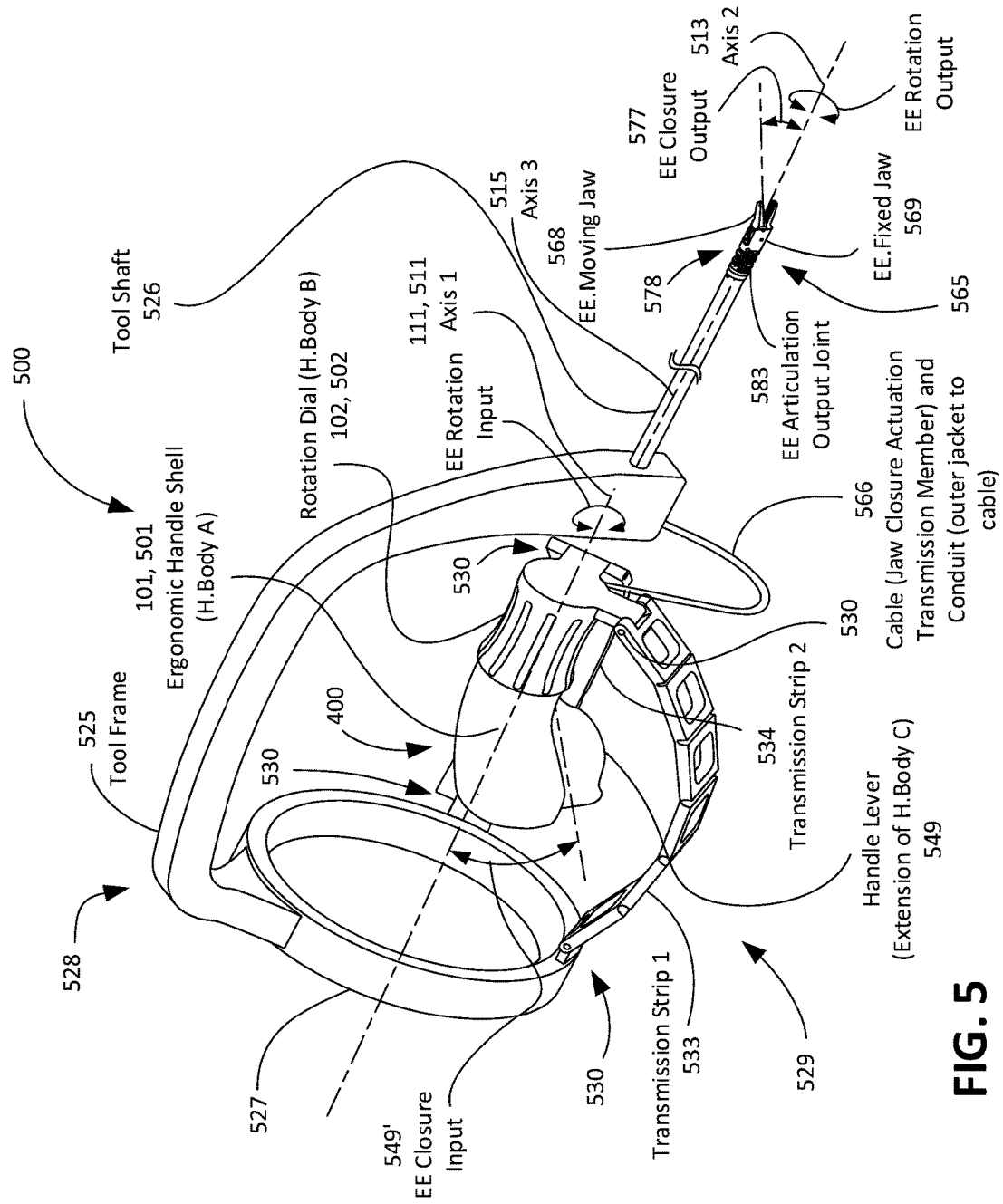
FIG. 5 illustrates one example of a medical device (e.g., a laparoscopic device) having the utility of an unlimited roll handle assembly such as the one shown in FIGS. 4A-4B and described herein.
Figure 7:
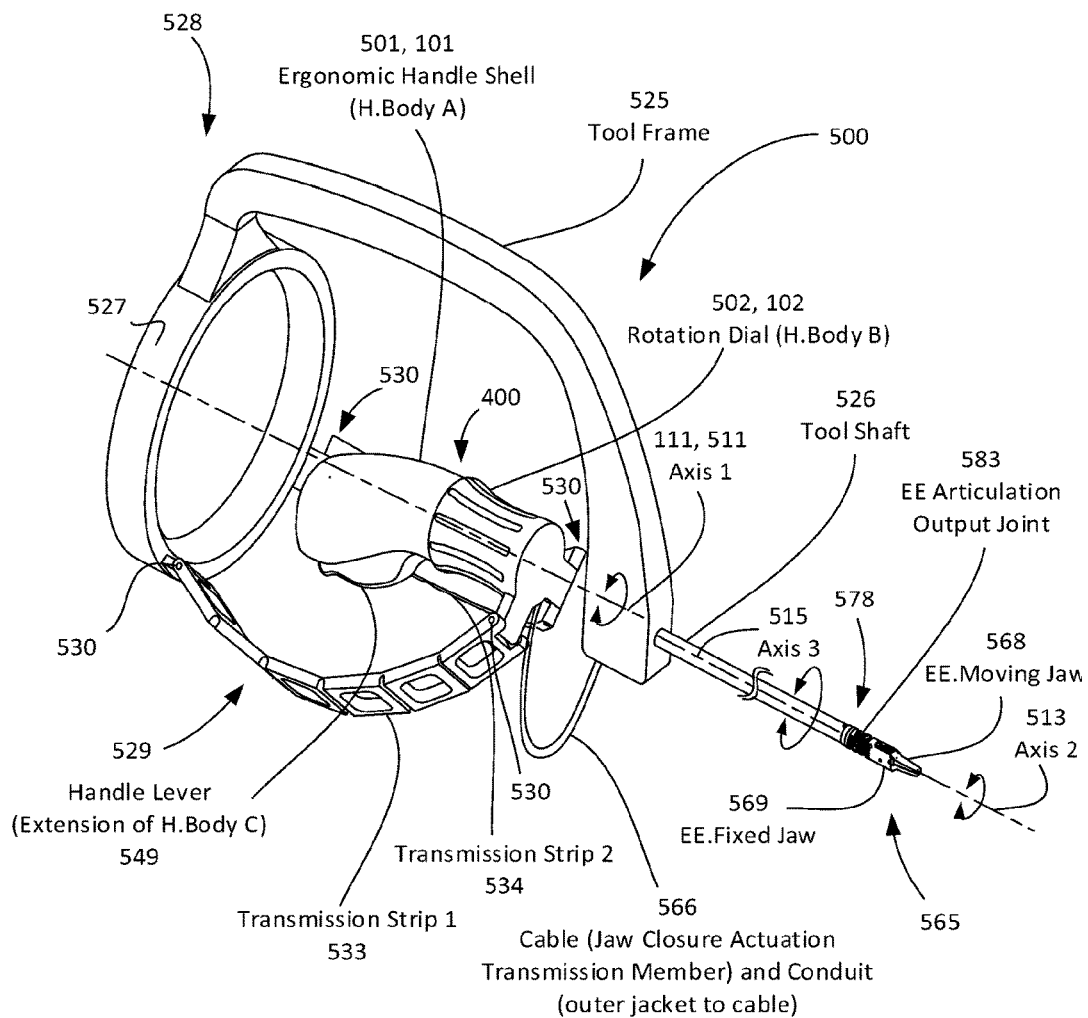
FIG. 7 shows another example of a medical device having an unlimited roll handle assembly and a jaw assembly end-effector such as the one shown in FIG. 5.

An apparatus including the unlimited roll handle assemblies shown in FIGS. 4A and 4B above is shown in FIGS. 5 and 7 as part of a medical device (specifically a laparoscopic device). FIGS. 5 and 7 shows a laparoscopic surgical instrument having an end-effector configured as a jaw assembly; in FIG. 5 the jaws are open and in FIG. 7 the jaws are shown closed.

In FIG. 5, the exemplary apparatus includes a tool frame 525, which includes a tool shaft 526 and a forearm attachment portion at the proximal end 527. A cuff (not shown) having a passage therethrough that is configured to hold a wrist or forearm of a user may be coupled to the forearm attachment portion; in some variations via a bearing between the forearm attachment portion of the frame and the cuff that is configured to slide or roll so that there is a roll rotational degree of freedom between the frame and the cuff about the tool axis. A proximal unlimited roll handle assembly such as the ones shown in FIGS. 4A and 4B may be connected to the tool frame by an input joint. The input joint may be configured to encode motion between the tool frame and the handle assembly, as shown in FIG. 5. In this example, the input joint includes a pair of transmission strips 533, 534 that connect to respective pivoting joints (not shown) in parallel to separately encode pitch and yaw rotations of the handle assembly. An output joint 583 (shown as an end-effector articulation joint) between the end-effector and the tool frame (e.g., tool shaft) receives transmission input (e.g., cables, not shown) from the output joint 533, 534 to articulate the end-effector.

In this example, the handle assembly includes an ergonomic palm grip portion 501 (handle shell) that connects to the rotation dial 502, which enclose an internal push rod and shuttle (not visible); these four elements are constrained per the constraint map shown in FIG. 1. The handle assembly also includes an end-effector control 549 input (in this example, defining the end-effector jaw closure input 549) that is configured as a handle lever and acts as a rigid extension of the internal push rod. In alternate configurations, the handle lever is coupled to the push rod via a transmission mechanism that may comprise a linkage, cams, springs, etc. A transmission cable 566 connects to the shuttle and acts as a jaw closure actuation transmission member extending from the shuttle and through the tool shaft to the end-effector. This transmission cable may be enclosed by a protective and/or supporting sheath or cover or conduit, for some or entire portion of its length. The end-effector itself is a jaw assembly including a first (ground) end-effector portion, in this example, including a fixed jaw 569 to which a pivoting second end-effector portion (moving jaw 568) is attached. The transmission cable 566 may couple to the moving jaw at the end-effector closure output 577.

In FIG. 5, rotation of the dial portion of the handle assembly when the user's forearm is mounted to the proximal end and the palm grip region is held in the user's hand so that the user can rotate the dial between the thumb and fingers, rotates the entire tool frame, and therefore the end-effector that is attached to the distal end of the tool frame via an end-effector output articulating joint. Thus, the handle may rotate about first axis 511 referred to as handle articulated roll axis (axis 1), to cause the tool shaft to rotate in a third axis 515 referred to as the tool shaft roll axis (axis 3), in turn causing the end-effector to roll about a second axis, referred to as an end-effector articulated roll axis (axis 2).

The rotation dial 502 (H.Body B) as shown in FIG. 5 is rotated about axis 1 511. The rotation of H.Body B leads to rotation of tool frame 525 via transmission strips 533, 534 (as they constrain rotation DoF), tool shaft 526 (about axis 3 515) and therefore, the end-effector (about axis 2 513). When handle is articulated using the input articulating joint, the end-effector articulates via output articulating joint. Now, the center axis (axis 2) for end-effector is different from the axis 3, the shaft axis.

Figure 6:
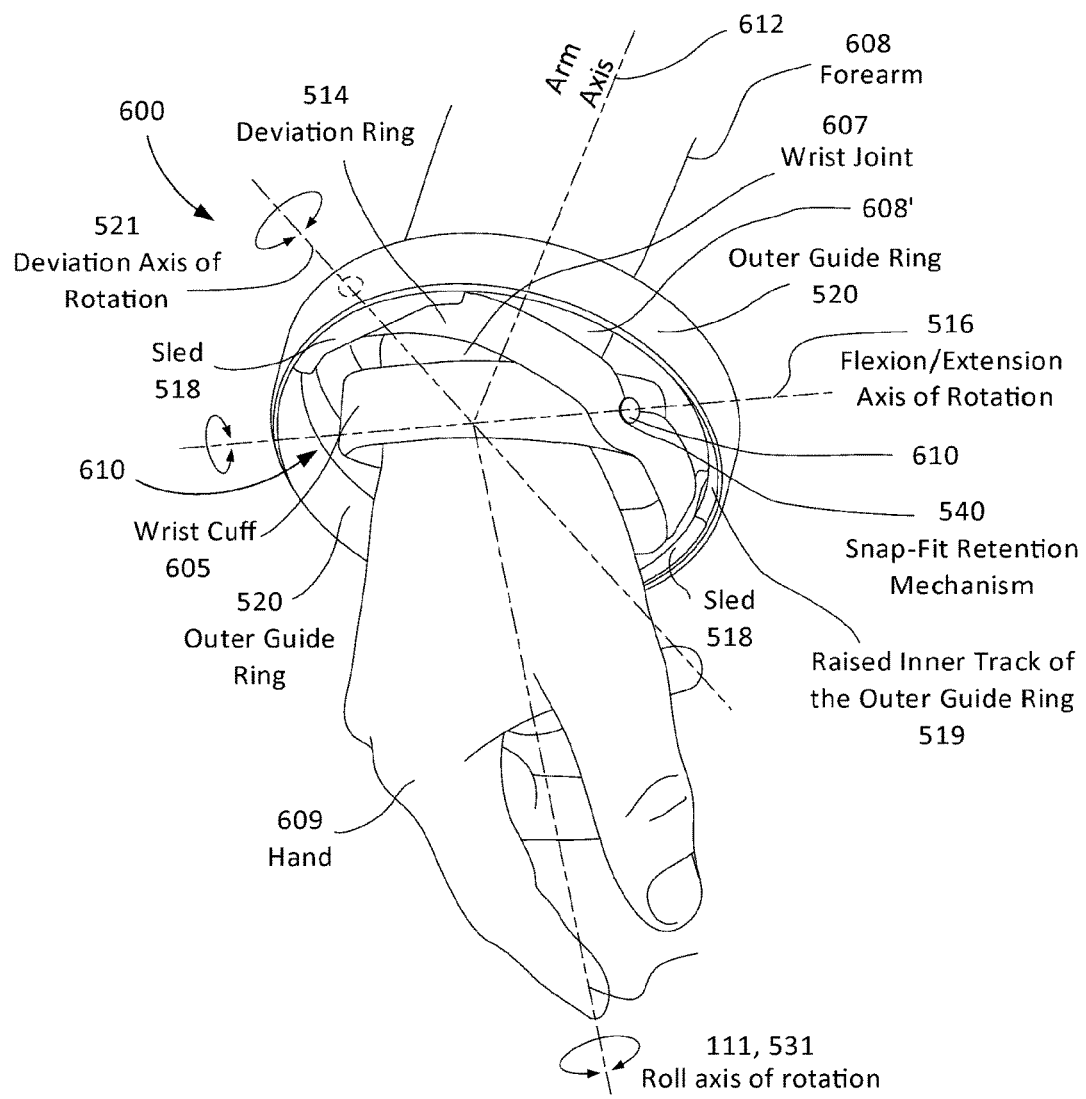
FIG. 6 shows on example of a cuff that can couple with a forearm attachment portion of a tool shaft of a medical device including an unlimited roll (roll) handle assembly. The cuff includes a passage therethrough that is configured to hold a wrist or forearm of a user, wherein the cuff is configured to couple to the forearm attachment portion of the tool frame.

The above description is particularly relevant when describing apparatuses that either do not attach to the forearm or attach via a roll joint, so that rotation of the handle dial portion leads to rotation of the forearm attach apparatus about the wrist via transmission strips (as they constrain rotation DoF), leading to rotation of tool frame, tool shaft and eventually, end-effector. FIG. 6 illustrates an example of a forearm attachment component that may be used. In FIG. 6, the forearm attachment comprises a 3-Axis gimbal assembly including a wrist cuff 605 that securely attaches to the user's wrist/forearm 607, 608, leaving their hand 609 free to move (e.g., to grasp the handle and manipulate the rotating dial and end-effector control input). In this example, the forearm attachment allows pitch, yaw and roll degrees of freedom; the cuff attaches to a deviation ring 514 that is pinned to rotation about flexion/extension axis of rotation 516. The deviation ring is itself coupled in a pivoting axis (deviation axis of rotation 521) to a sled 518 which rolls around a raised inner track 519 of an outer guide ring 520, rolling about a roll axis of rotation 531. This assembly provides pitch, yaw and roll degrees of freedom when coupled to the apparatus tool frame; for example, the outer guide ring maybe formed as part of the forearm attachment portion of the apparatus, or it may be attached thereto. The cuff may releasably couple into the rest of the forearm attachment apparatus via a snap-fit 540 or other coupling.

Figure 8:
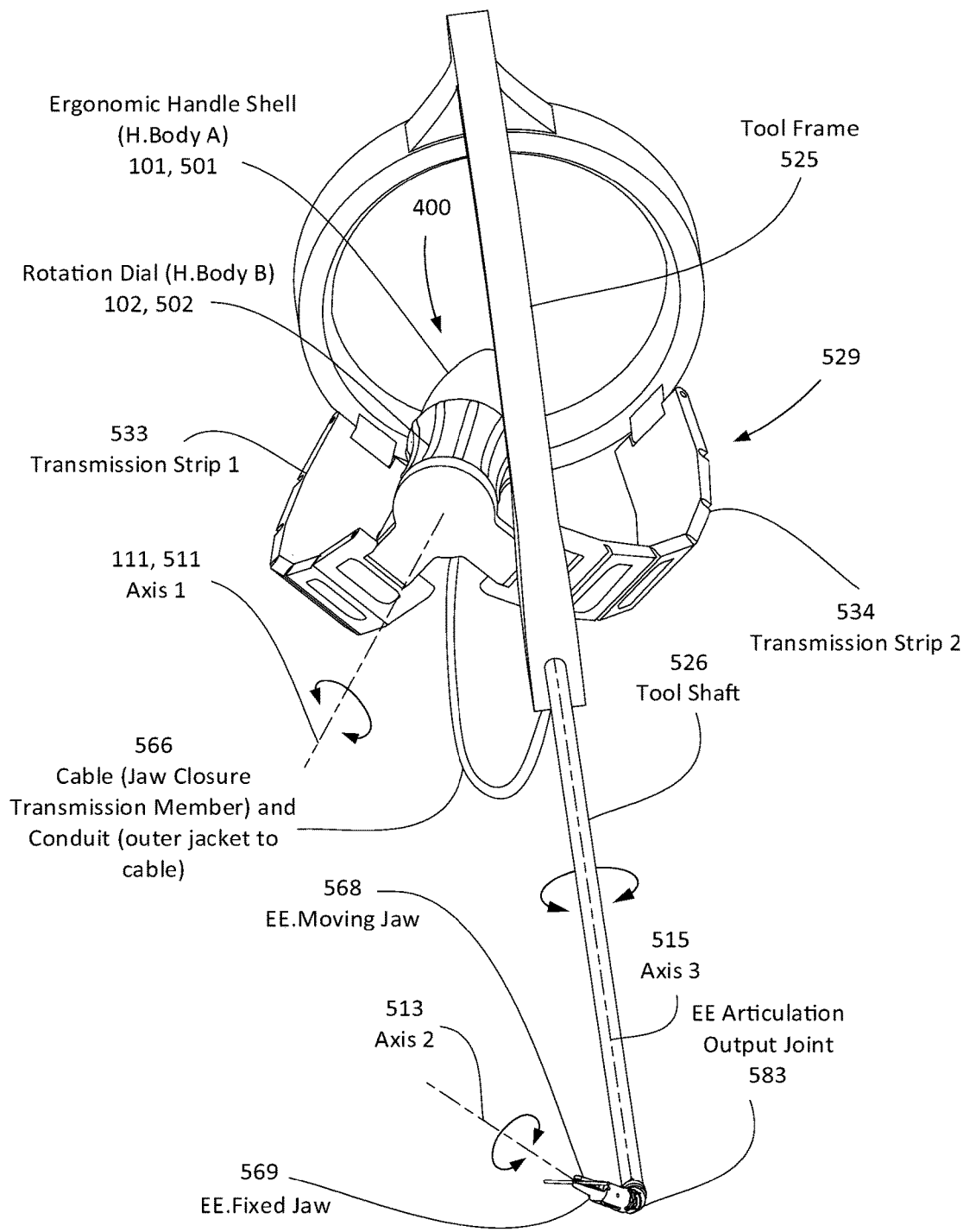
FIG. 8 is another view of a medical device having both an unlimited roll handle assembly and a distal end-effector configured as a jaw assembly that is shown in FIG. 8 as an articulated position with a closed end-effector; the unlimited roll handle assembly is similar to that shown in FIGS. 4A-4B.

FIG. 8 shows another view of the laparoscopic instrument of FIGS. 5-7 in an articulated position holding a needle that may be used to suture tissues. The end-effector fixed jaw (ground) and end-effector moving jaw can be rotated about axis 2 such that the tool shaft/tool frame rotates about axis 3 while the handle is rotated about axis 1; all while holding the needle securely by moving the end-effector moving jaw with respect to an end-effector fixed jaw via a jaw closure actuation transmission member connected to H.Body D at the proximal end of the device. The apparatus shown in FIGS. 5-8 may fit a constraint map such as the one shown in FIG. 20A.

Figure 9:
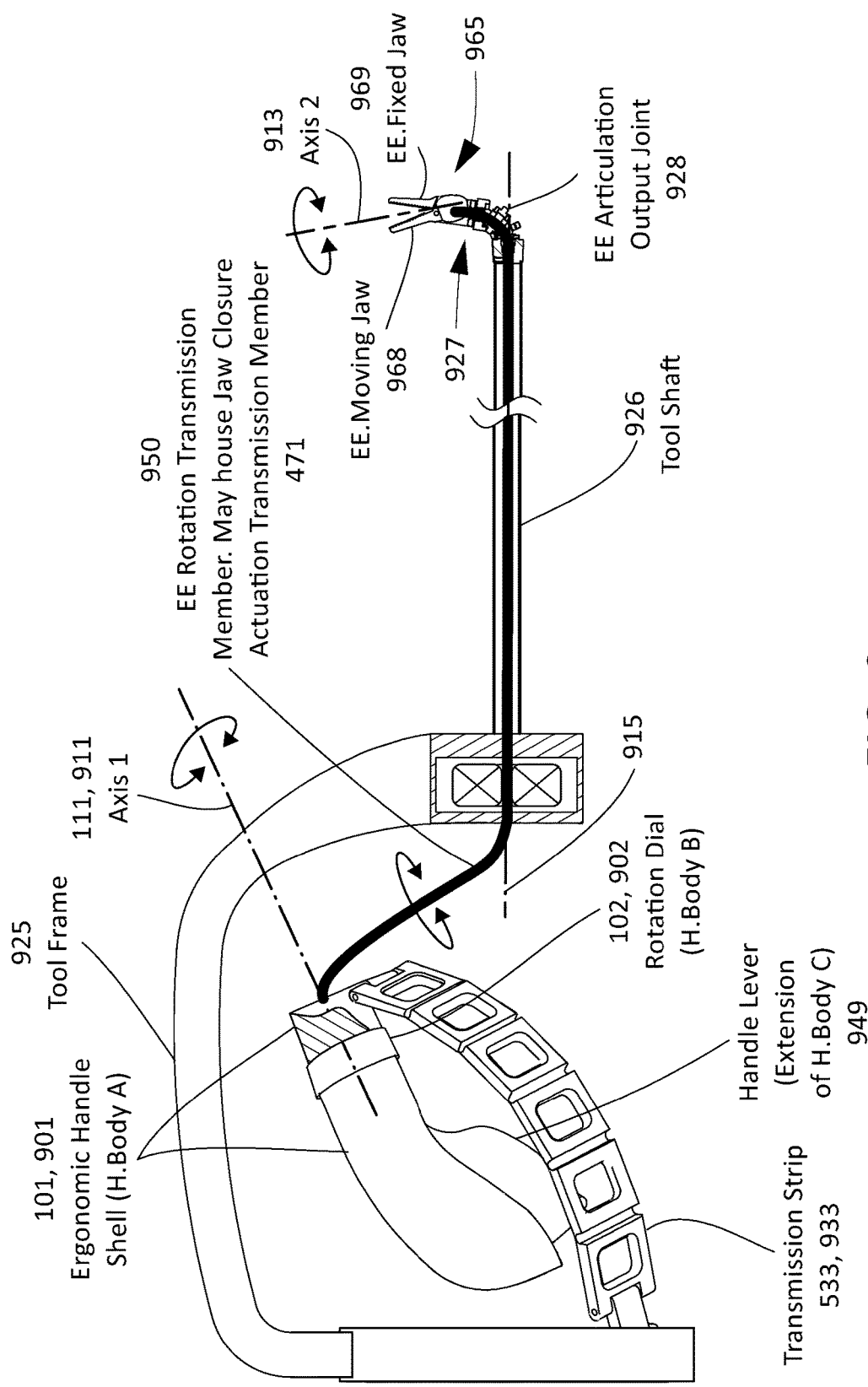
FIG. 9 shows another example of a medical device having both an unlimited roll handle assembly and a distal end-effector configured as a jaw assembly, illustrating an end-effector transmission connecting the rotation dial (H.Body B) to the end-effector.

Another variation of an apparatus that conforms to the constraint map described in FIG. 1 is shown in FIG. 9. In this example, the rotation of rotation dial 902 (H.Body B) about axis 1 911 leads to rotation of the end-effector assembly (shown here as a jaw assembly including a moving jaw 968 and a fixed jaw 969) about axis 2 915. Here, the tool frame 925 including the tool shaft 926 does not rotate about either their axis (axis 3 915). The tool frame may still be connected to a cuff mounted on a user's forearm via a forearm attachment joint that may provide a pitch and/or yaw rotational DoF. The end-effector assembly has a rotational DoF with respect to the distal end of the end-effector articulation output joint about axis 2 (similar to that between H.Body A 901 and H.Body B 902 about axis 1) and the end-effector rotation transmission member 950 connects H.Body B directly to the end-effector assembly via a torsionally stiff end-effector rotation transmission member 950. This may also be the jaw closure actuation transmission member or may house and therefore route, a flexible jaw closure actuation transmission member, for example, a flexible shaft (end-effector rotation transmission member) that is torsionally stiff to transmit rotation from one end to another housing a flexible cable (jaw closure actuation transmission member) inside it.

Figure 10:
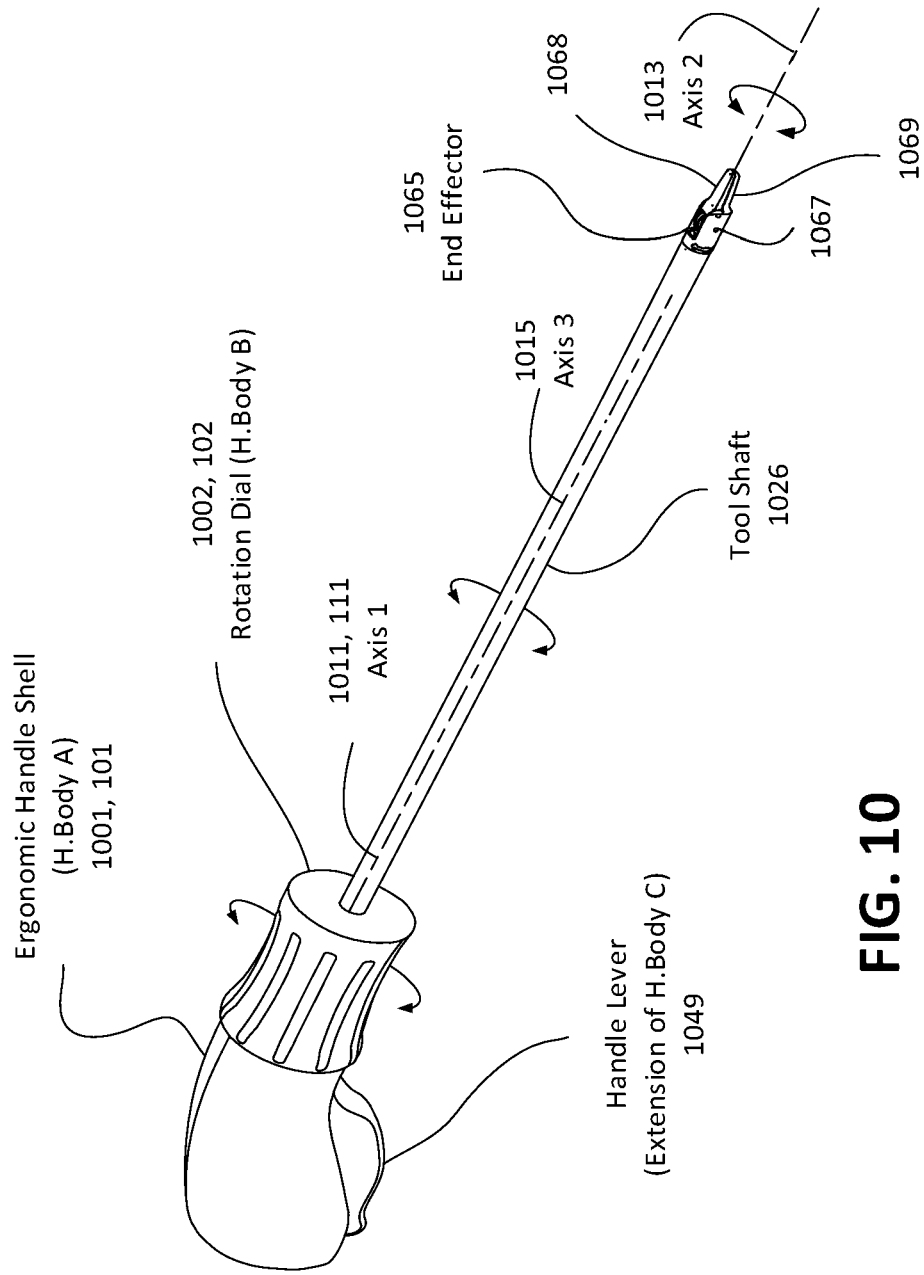
FIG. 10 shows an example of another apparatus including an unlimited roll handle assembly and a distal end-effector configured as a jaw assembly in which the apparatus is a non-articulating "straight stick" laparoscopic device.

Another example of an apparatus using the unlimited roll handle apparatuses described herein is shown in FIG. 10. This apparatus is configured as a straight stick device with a non-articulating end-effector; other straight stick apparatuses are described in U.S. Pat. No. 4,712,545, U.S. Pat. No. 5,626,608, and U.S. Pat. No. 5,735,874; such apparatuses may benefit from any of the unlimited roll handle apparatuses such as those shown in FIGS. 4A and 4B. FIG. 10 shows an example of a surgical instrument consisting a handle assembly (including palm grip portion 1001 and a dial portion 1002), tool shaft 1026 and an end-effector 1068. There is a rotation joint between the moving jaw and fixed jaw of the end-effector in this example, where the end-effector is configured as a jaw assembly. The end-effector connects to the rotation dial 1002 (H.Body D) via a jaw closure actuation transmission member (not visible in FIG. 10). This instrument provides the functionality of closing and opening the end-effector by moving the moving jaw relative to the fixed jaw. It may also provide the rotation of the end-effector about the handle axis (axis 1 1011); the shaft axis 1015 (axis 3) is parallel to the handle axis 1 1011 via rotation of H.Body B 1002, tool shaft 1026 and therefore, the end-effector 1068.

Figure 11:
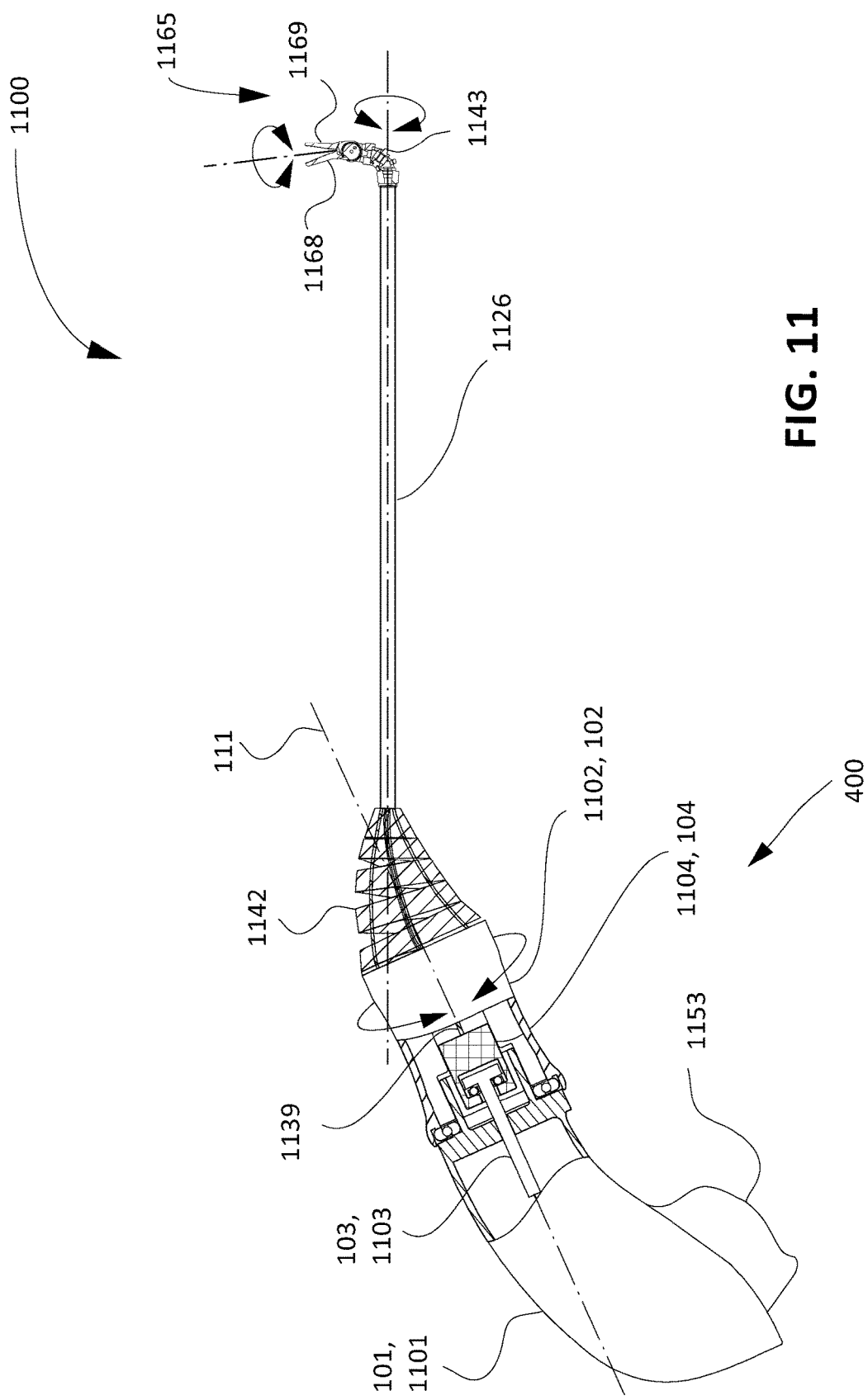
FIG. 11 shows an example of another articulating medical device using an unlimited roll handle assembly such as the one shown in FIGS. 4A-4B.

Also described herein are articulating apparatuses in which the articulation at the input joint is encoded via a serial kinematic or parallel kinematic input articulation joint. For example, FIG. 11 shows an articulating laparoscopic device. Such devices include a handle, tool shaft 1126 and an articulating end-effector 1168, 1169. Similar to non-articulating laparoscopic instrument, these also contain an end-effector rotation joint (open/close functionality) between moving jaw 1168 and a fixed jaw 1169. But, in addition to this open/close joint, these also contain an output articulation joint 1143 for end-effector articulation and an input articulation joint 1142. This input articulation joint maybe a serial kinematic (S-K) or parallel kinematic (P-K). Some articulating instruments that consist of S-K input joint (such as the one shown in FIG. 11) can be found, for example, in U.S. Pat. No. 8,465,475; U.S. Pat. No. 5,713,505, U.S. Pat. No. 5,908,436, U.S. application Ser. No. 11/787,607 and U.S. Pat. No. 8,029,531. Examples of parallel kinematic input joint based articulating instruments may be found, for example, in U.S. 2013/0012958. In such devices, the end-effector may be a jaw assembly and may be shown to be open jaw condition but it can perform rotation using end-effector rotation joint even in closed jaw condition as well as in articulated condition.

Figure 12:
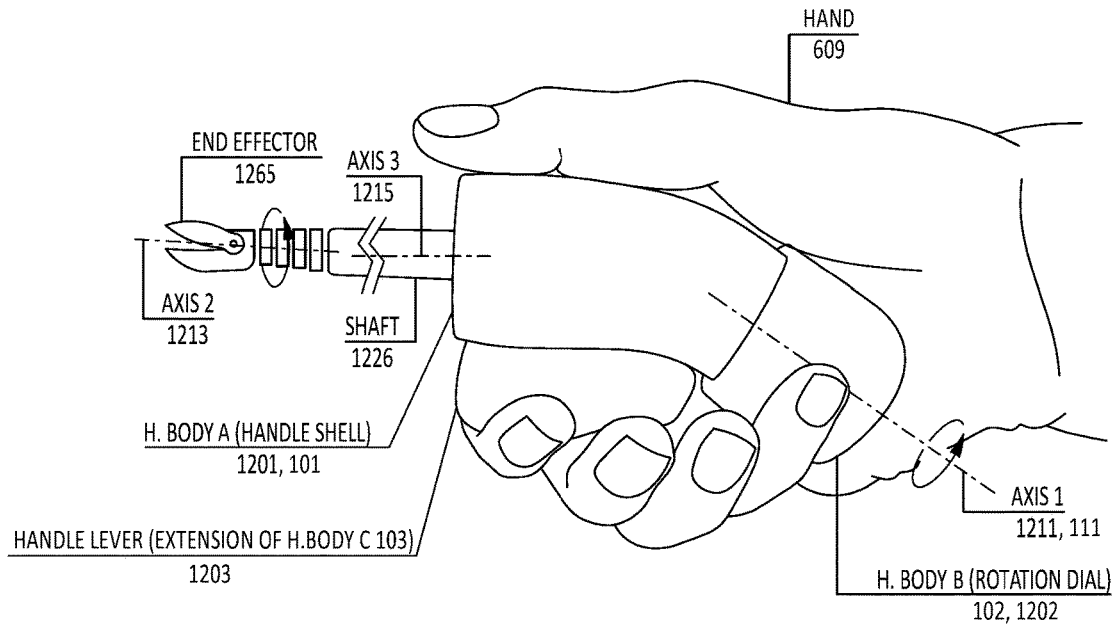
FIG. 12 is an alternative example of an unlimited roll handle assembly in which the palm grip (H.Body A) is distal to the rotation dial (H.Body B), which is instead located proximally of the palm grip.
Figure 13:
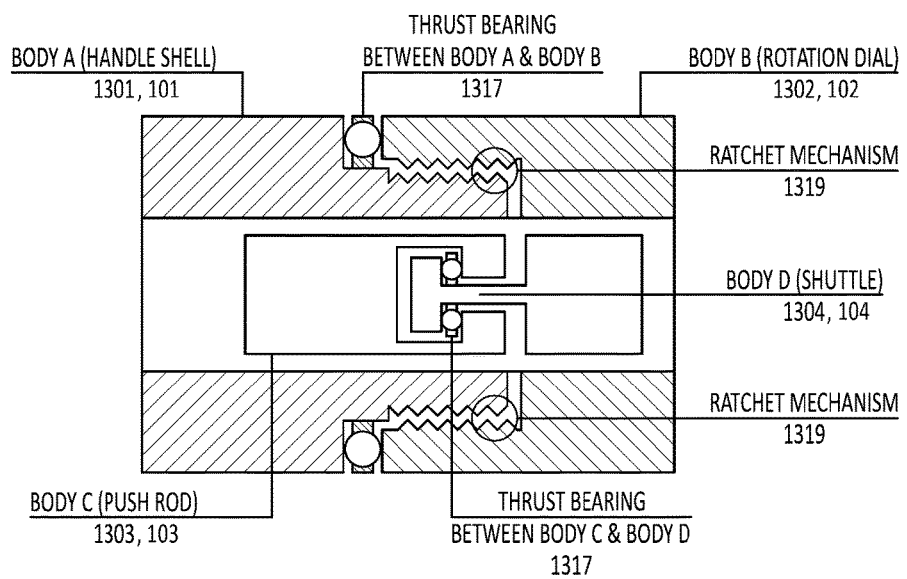
FIG. 13 illustrates the use of ratchets providing discrete rotation units with the rotation dial in an apparatus as described herein.

FIGS. 12 and 13 illustrate other unlimited roll handle assembly variations that follow the constrained map illustrated in FIG. 1. These handle variations may be used with any of the other apparatus components described herein (including with other device architectures and/or constraint maps). For example, in FIG. 12, the rotation dial 1202 is proximal to the palm grip portion 1201. The apparatus may include a shaft 1226 and end-effector 1265, and may include the same axes as described above (first axis 1211, second axis 1213 and third axis 1215). In the constraint map of FIG. 1, joint characteristics (DoFs and DoCs) between H.Body A and H.Body C are the same as the ones between H.Body B and H.Body D. Also, joint characteristics (DoFs and DoCs) between H.Body A and H.Body B are the same as the ones between H.Body C and H.Body D. Therefore, either of the 4 bodies can be referred as ground reference. In FIG. 13 shows a different location where the reference ground is located in the handle assembly. In FIG. 13, when mapped to constraint map from FIG. 1, H.Body B is chosen as reference ground and interfaces firmly with user's hand, whereas, H.Body A is rotated with respect to H.Body B. Here, H.Body C rotates with respect to H.Body D and H.Body C. Another way of explaining this embodiment (shown in FIG. 13) is that the handle's rear end is now placed at the proximal end and vice versa.

Any of the apparatuses described herein may include a rotation lock/ratcheting mechanism, as illustrated in FIG. 13. The handle assembly shown by the constraint map of FIG. 1 consists of a joint between H.Body A and B which provides rotational DoF about axis 1. This rotation can be made more tactile by application of ratcheting feature between H.Body A and H.Body B, as shown in FIG. 3B. Ratcheting between H.Body A and H.Body B can provide a sense of discrete rotation degrees while rotating about axis 1. FIG. 13 illustrates a similar variation. In this example, a thrust bearing 1317 is located between the palm grip 1301 and the rotation dial 1302, as is a ratchet mechanism 1319. The shuttle 1304 and push rod 1303 otherwise operate per the constrained diagram of FIG. 1.

Figure 14:
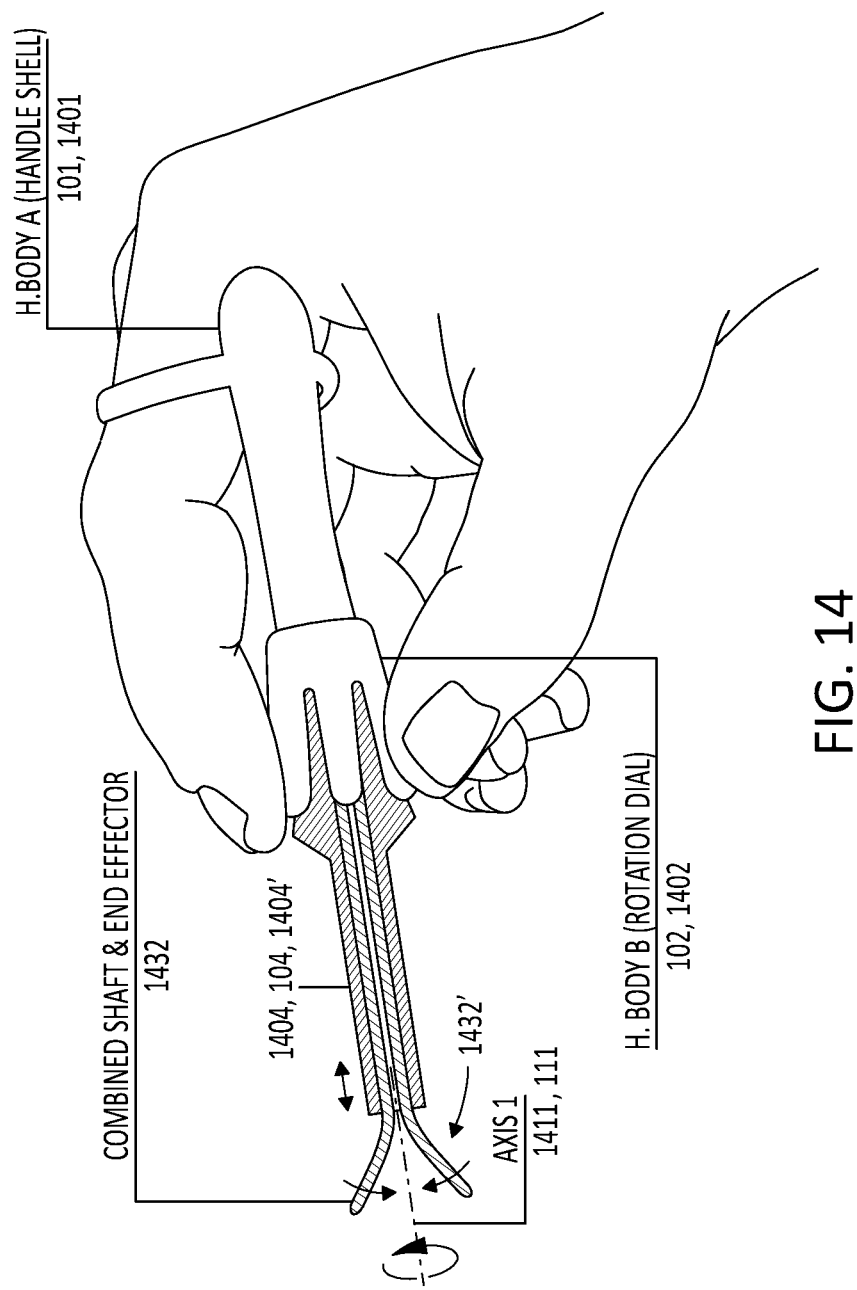
FIG. 14 illustrates another embodiment of an apparatus using an unlimited roll handle assembly as described herein.
Figure 15:
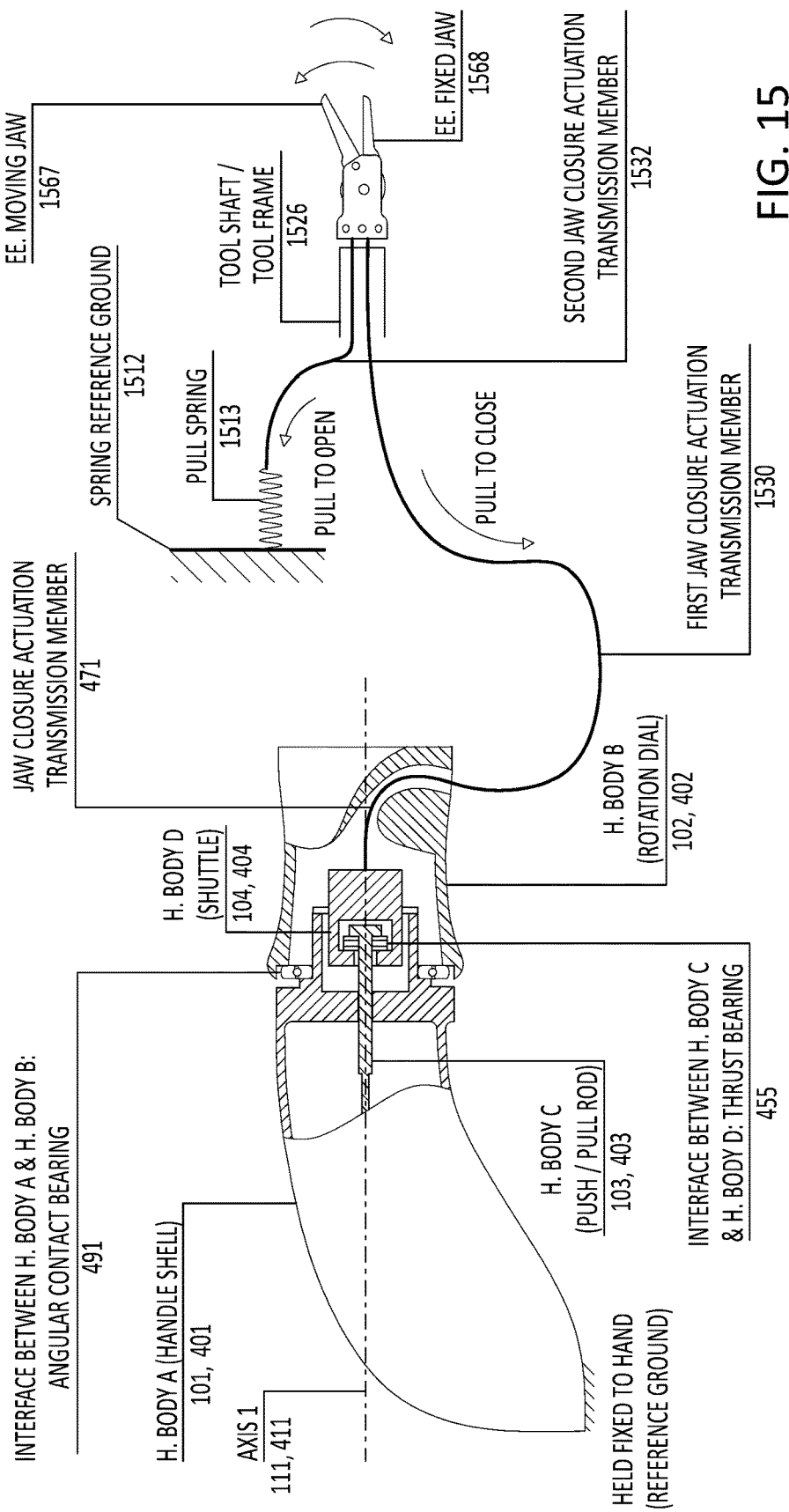
FIG. 15 is another example of an unlimited roll handle assembly coupled to an end-effector configured as a jaw assembly.

The handles described herein may also be used with an apparatus configured to provide a pecking motion at an end-effector using these handle mechanisms. For example, other embodiments of the handle mechanism (fitting the constrained map of FIG. 1) may show the opening and closing of an end-effector jaw triggered directly by radial pressing of the rotation dial (H.Body B) 1402. The device described in FIG. 15 consists of a handle shell (H.Body A) 1401, rigidly attached to the hands of the user. Further, it may include a rotation dial 1402 (H.Body B) which can rotate relative to handle shell (H.Body A) about axis 1 1411. When rotation dial (H.Body B) is pressed, it pushes the shuttle (H.Body D) 1404 along the axis 1 1411, by making use of the translational DoF of shuttle (H.Body D) with respect to rotation dial (H.Body B) along axis 1. With the stroke of shuttle (H.Body D) along axis 1, the combined shaft and end-effector, which is rigidly connected to the rotation dial, closes itself as shown in FIG. 14. The flexible nature of the body representing combined shaft and end-effector leads the movement of shuttle over the combined shaft and end-effector as a sleeve. This sleeve, which is the shuttle, leads to the opening and closing of the end-effector, making it act as a double action jaw which can have different applications in open surgery like eye surgery and minimal invasive surgery. Here, push/pull rod (H.Body C, which can't be seen in FIG. 14) may be keyed to the interior of the handle shell and attached via a spring such that when the push/pull rod moved relative to handle shell, it retracts back to its original position with the help of the spring. This will allow the motion of push/pull rod (H.Body C) and shuttle (H.Body D) along axis 1 when the shuttle is pushed along axis 1 by radial pressing of rotation dial (H.Body B) and will assist in retracting the shuttle (H.Body D) along with the push/pull rod (H.Body C) to their original position. Therefore, this embodiment represents a device which can rotate the end-effector about its normal axis (axis 1) and help in securement of respective external bodies in the end-effector by pecking the shuttle to cause opening/closing of the end-effector FIG. 15 is another example of an apparatus as described herein, configured as a Pull-Pull configuration for jaw closure transmission. This example includes an unlimited roll handle assembly such as was shown in FIG. 4A, including a shuttle 404 H.Body D keyed to H.Body B 402. Here, the jaw closure transmission member 1530 is pulled to close the end-effector moving Jaw 1567 with respect to end-effector fixed jaw 1568 and is pulled to open the moving Jaw with respect to fixed jaw. The jaw closure (open/close) actuation transmission member 1530 is attached to H.Body D 404, where H.Body D can translate with respect to H.Body B 402 due to DoC in translation along axis 1 411 with respect to H.Body C 403. Once H.Body D moves along axis 1 to pull the jaw closure actuation transmission member to close the jaws (i.e. bringing the moving jaw and fixed jaw together), a second jaw closure (open/close) actuation transmission member 1532 is pulled to open the end-effector moving jaw. To open the jaws the second jaw closure actuation transmission member 1532 may be pulled. In one embodiment, this transmission member can be pulled using a pull spring 1513, grounded at a reference frame called "Spring Reference Ground". Depending on how the roll transmission member is routed throughout the whole assembly, "Spring Reference Ground" can occur at different locations in the assembly, as described below: (1) by means of input art joint, tool frame/shaft, output articulating joint (the "spring reference ground" can occur at H.Body B or tool frame/tool shaft or fixed jaw); (2) by means of an independent roll transmission member routed across the input art joint, through tool frame/shaft, and output articulating joint. Extra roll DoF between output joint distal end and end-effector base (the "spring reference ground" can occur at H.Body B or at the end-effector fixed jaw).

Figure 16:
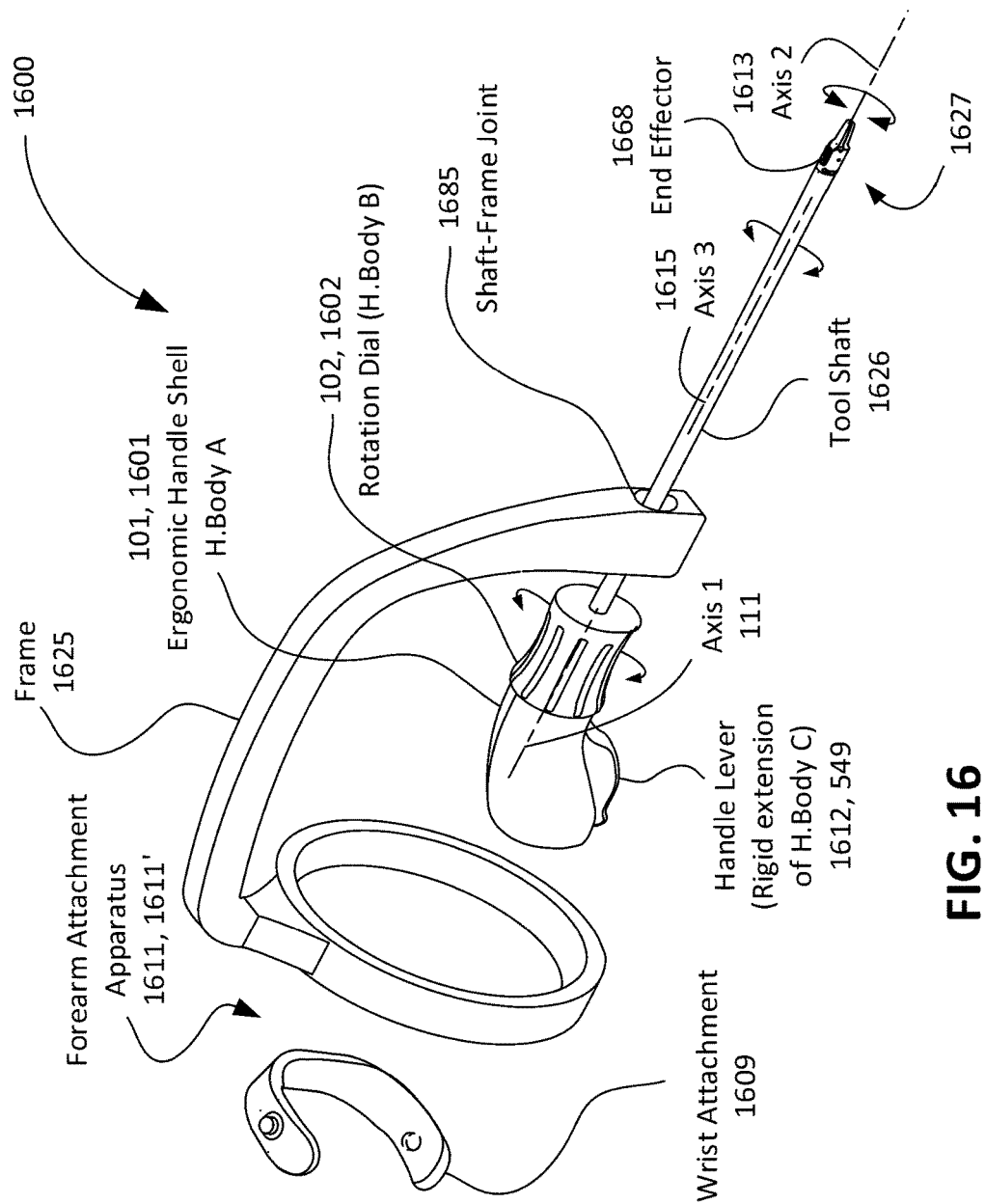
FIG. 16 is a front perspective view of an exemplary surgical device incorporating an unlimited roll handle assembly as described herein and an arm (forearm) attachment.

In some variations, the unlimited roll handle assembly is generally configured to include a forearm attachment apparatus. The unlimited roll handle apparatus may provide the ability for the apparatus to simultaneously transmit roll and closure action to Body D with respect to Body A. Such a variation including a forearm attach member with DoF was described above in FIGS. 5-8, and another example is shown in FIG. 16. In this example, a (one) joint exists between the wrist attachment/wrist cuff 1609 and the tool frame 1625, referred to as a forearm attach joint. A forearm attach joint may be used to couple the wrist attachment/wrist cuff and tool frame, allowing zero or one or more DoF between the arm and the apparatus. Some variations may be articulating or non-articulating devices that are forearm mounted. For example, one embodiment can include a roll DoF by providing a rotation joint between the wrist attachment and tool frame. This joint may use a "sled" (see FIG. 6) which can allow rotational DoF about the arm axis. Another embodiment can involve a pitch DoF by providing a rotation joint allow rotation about flexion/extension axis of rotation. Another embodiment can involve a yaw DoF by providing a rotation joint allow rotation about deviation axis of rotation. Another embodiment can involve both pitch and yaw DoF by providing a rotation joint allow rotation about flexion/extension axis of rotation and deviation axis of rotation respectively. This may use another body called deviation ring (see FIG. 6). Another embodiment can involve roll (about arm axis), pitch (about flexion/extension axis of rotation) and yaw (about deviation axis of rotation) DoF. Also as shown in FIG. 6, a joint may exist between tool frame and tool shaft, called a shaft-frame joint. This shaft-frame joint may have zero DoF (rigid connection between shaft and frame), which is the default configuration considered in this discussion. The device in FIG. 16 includes a handle palm grip 1601 (H.Body A), a rotation dial 1602 (H.Body B) and an end-effector input 1612, a shaft-frame joint 1615, an end-effector 1668 at a distal end of the tool shaft 1626. The apparatus also includes a handle axis, axis 1 1611, tool shaft axis, axis 3 1615 and an end-effector axis, axis 2 1613.

Some variations of a non-articulating instrument that is forearm mounted and that has an unlimited roll handle assembly may include a separate tool frame and tool shaft. In one such configuration, the tool frame and wrist cuff may be rigidly attached (0 DoF). In this case, if the tool shaft is rigidly connected to the handle dial, then the apparatus may be configured so that there is at least one roll rotation DoF between the tool shaft and tool frame. Furthermore, a shaft-frame joint can have roll DoF, Pitch DoF, Pitch and/or Yaw DoF.

Figure 17:
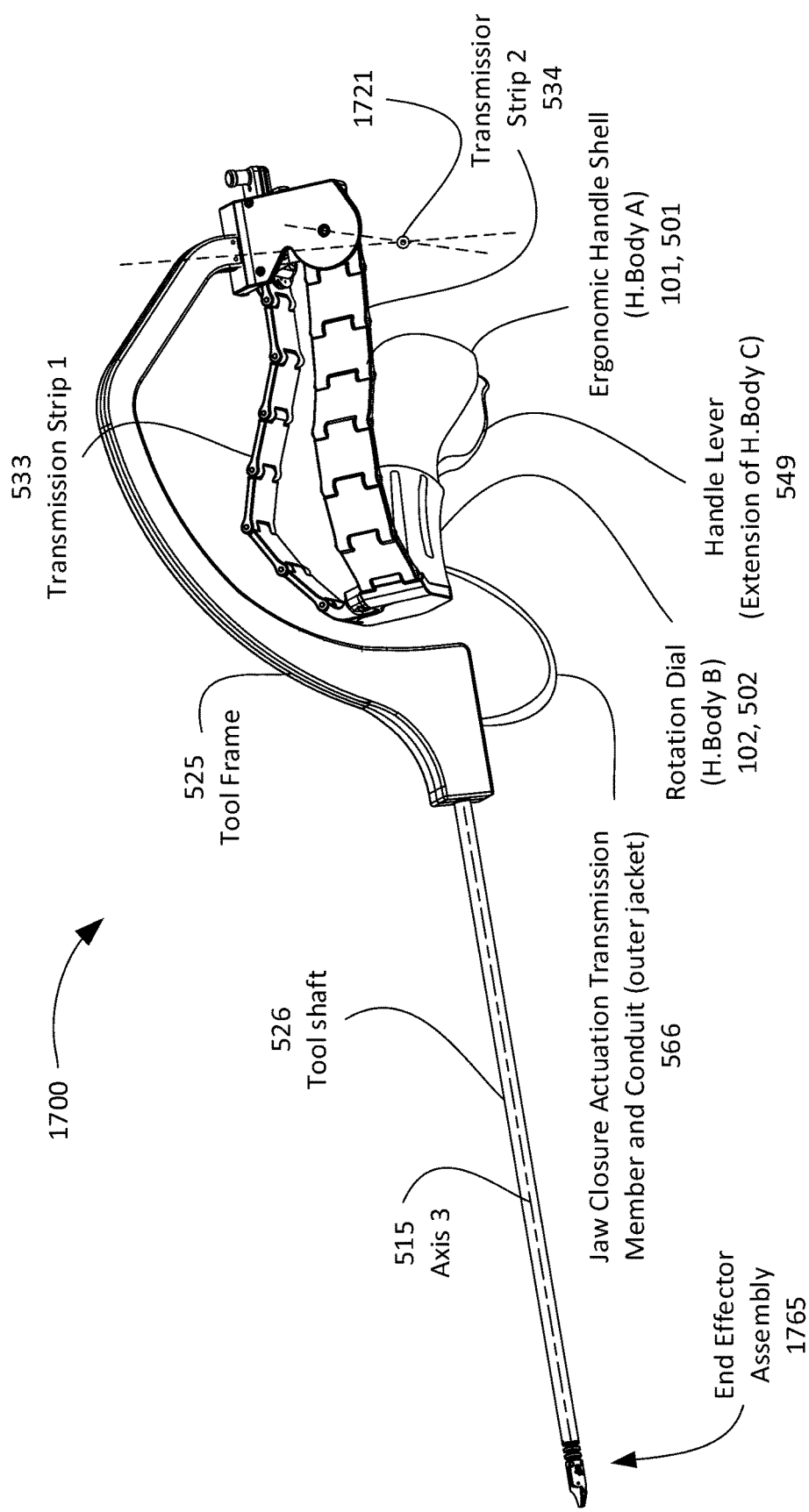
FIG. 17 is a side perspective view of an exemplary surgical device incorporating an unlimited roll handle assembly and an input joint encoding pitch and yaw articulation by a parallel kinematic mechanism and transmitting pitch and yaw motions to an output joint between the tool frame and the end-effector (shown configured as a jaw assembly).
Figure 18A:
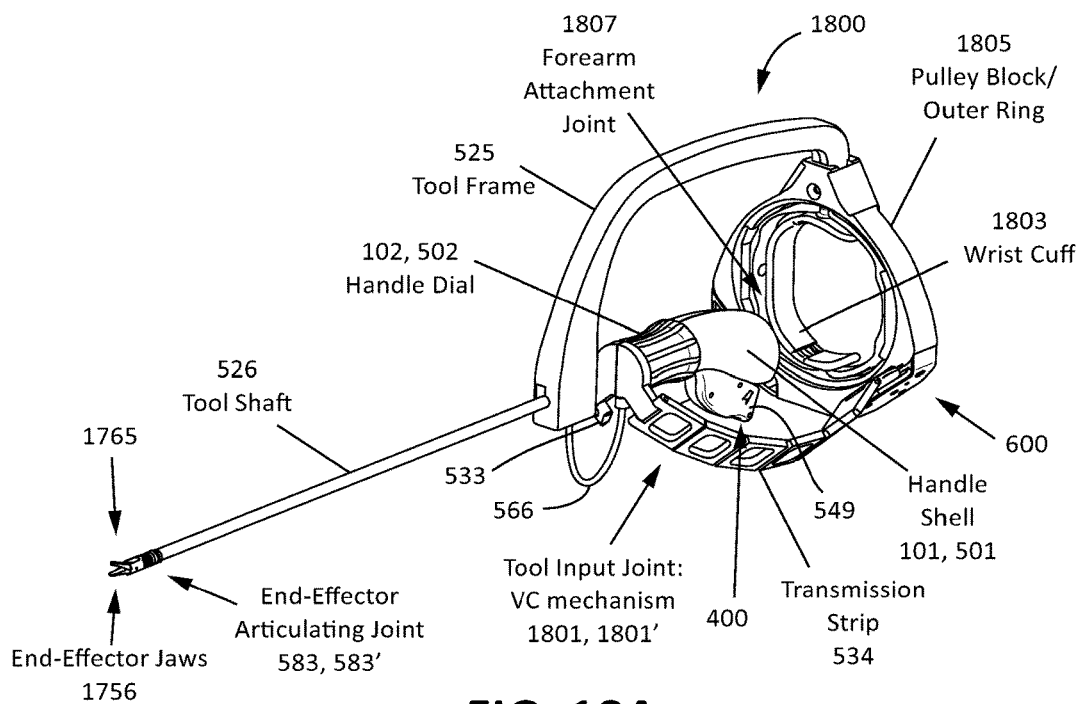
FIGS. 18A-18D show front perspective, left side, back perspective and right side perspective views, respectively, of a medical device including an unlimited roll handle assembly, an end-effector configured as a jaw assembly, a proximal forearm attachment and an input joint encoding pitch and yaw articulation that is transmitted to a output joint articulating the end-effector. The pitch and yaw input joint has a center of rotation where the pitch and yaw axes intersect at a virtual center of rotation approximately within a user's wrist when the user is holding the apparatus.
Figure 18B:
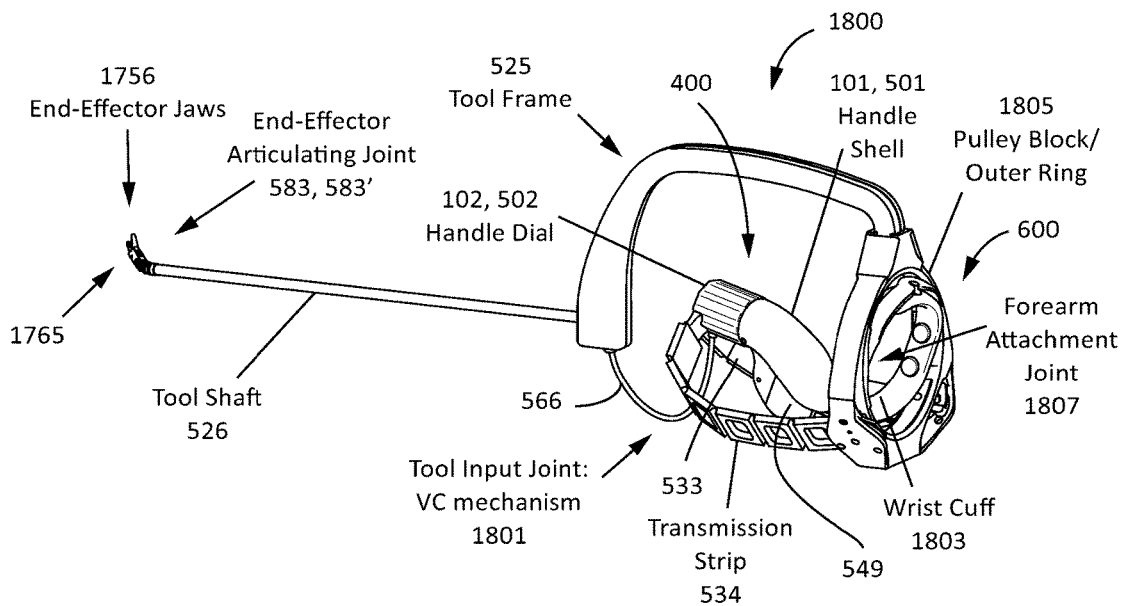
Figure 18C:
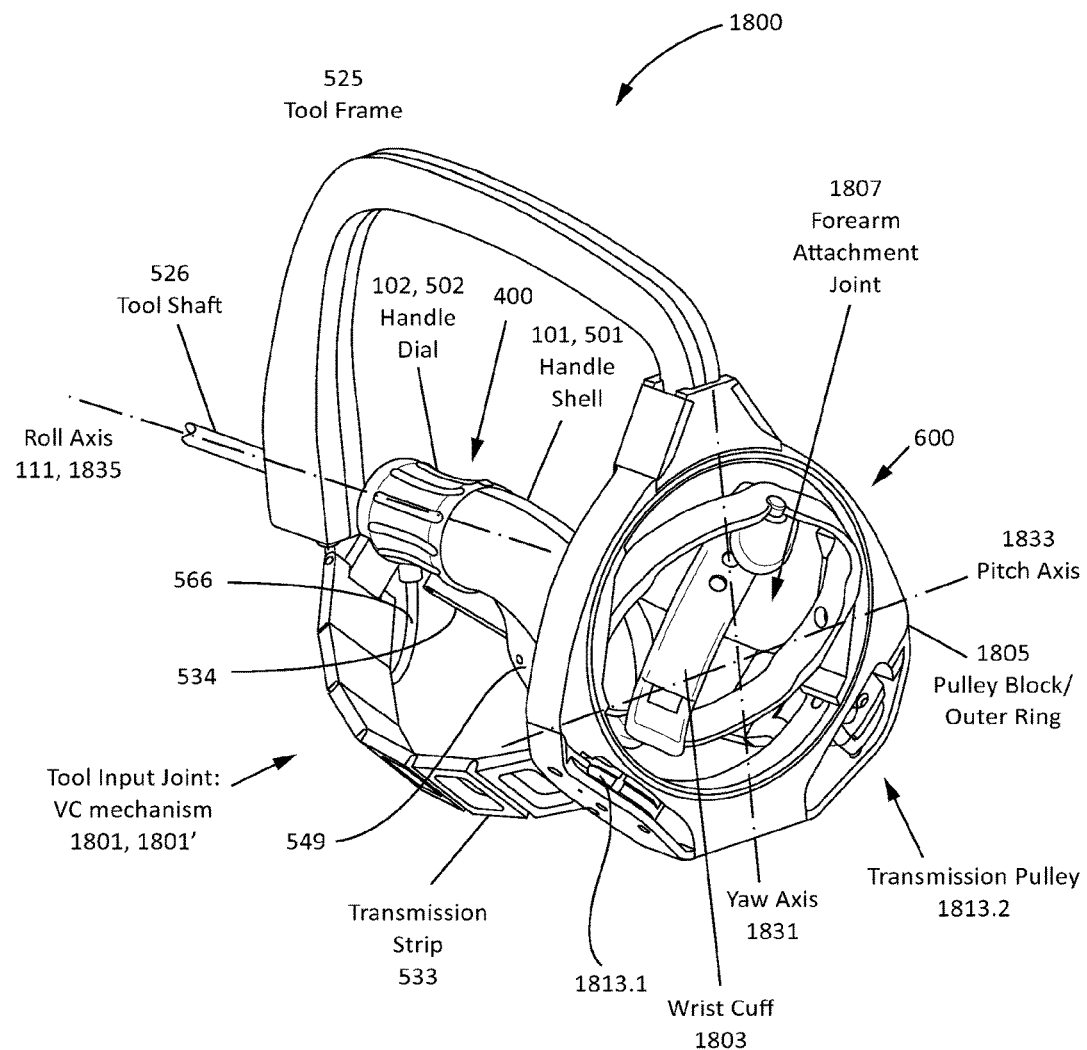
Figure 18D:
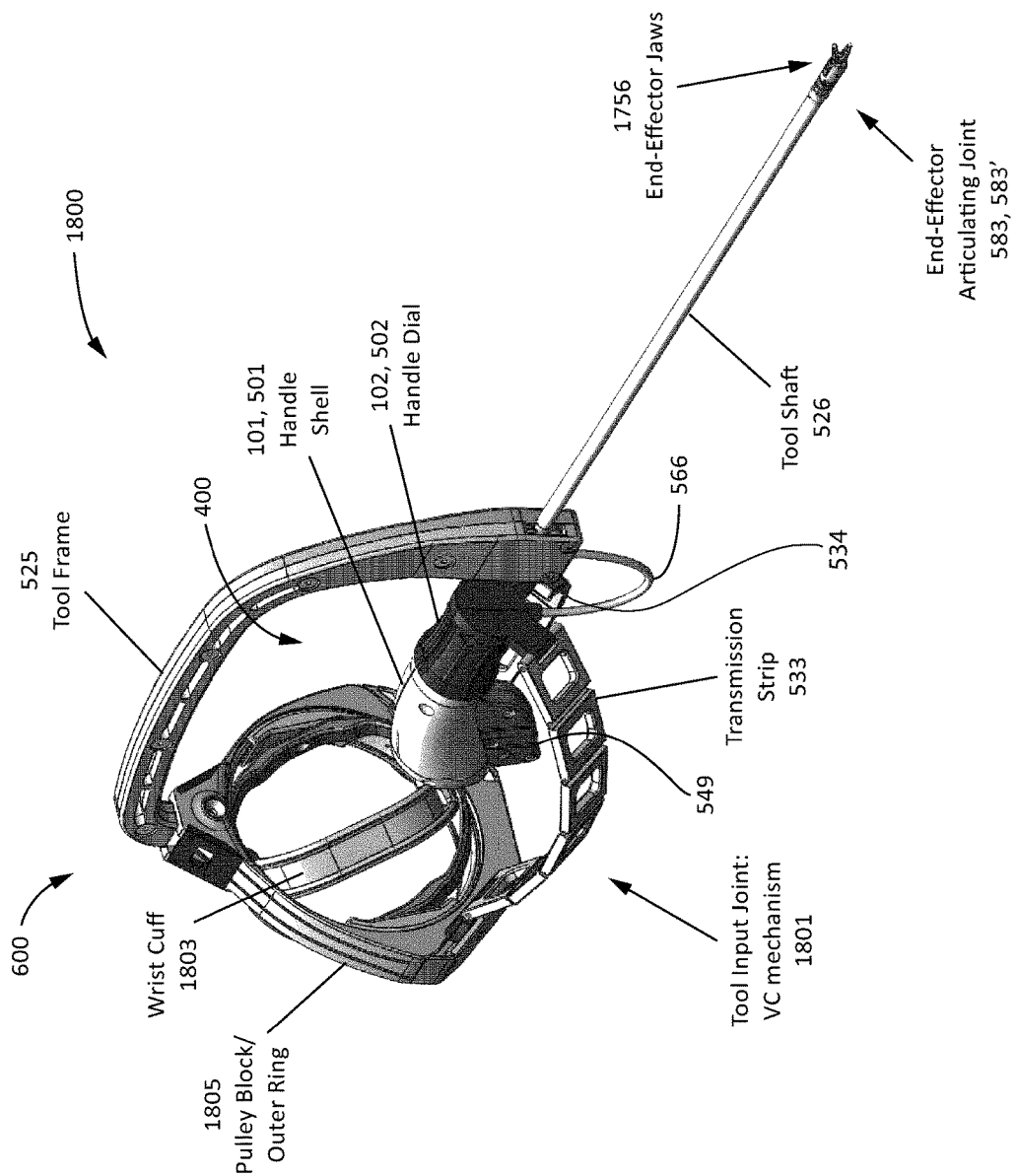

Any of the apparatuses including an unlimited roll handle described herein may also include a virtual center (VC) at the input articulation joint as shown in FIG. 17. This device can have serial or parallel kinematic input joint with joint axis intersecting at a virtual center. This device is similar to that shown in FIG. 5, but shows the virtual center 1721. The device includes an end-effector assembly 1768 that is also configured as a jaw assembly.

Example: Medical Device

Figure 19A:
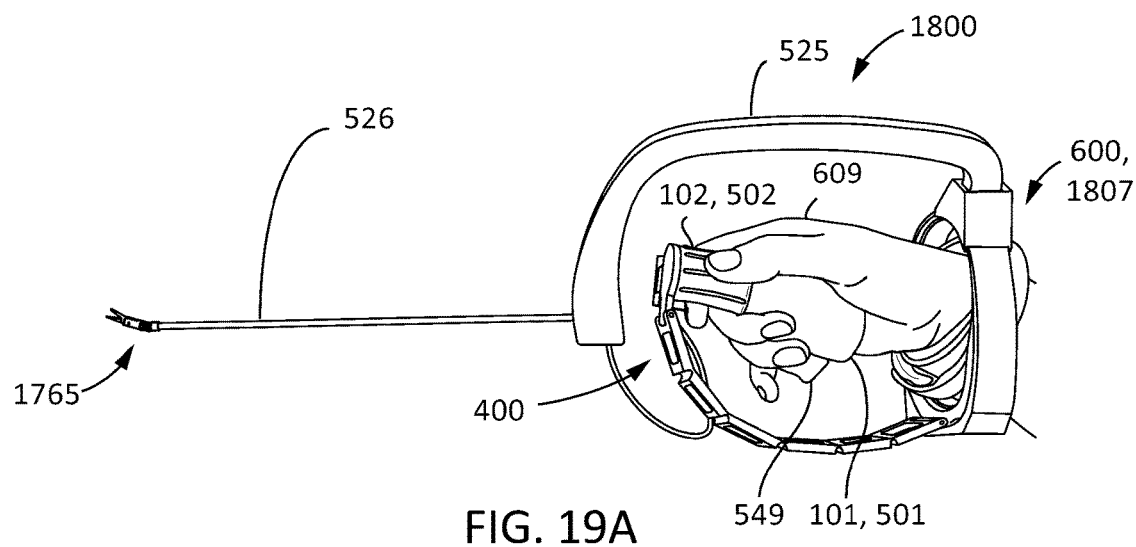
FIG. 19A shows a side view of a portion of a medical device such as the one shown in FIGS. 18A-18D, coupled to a user's forearm with the unlimited roll handle assembly held in the user's hand.
Figure 19B:
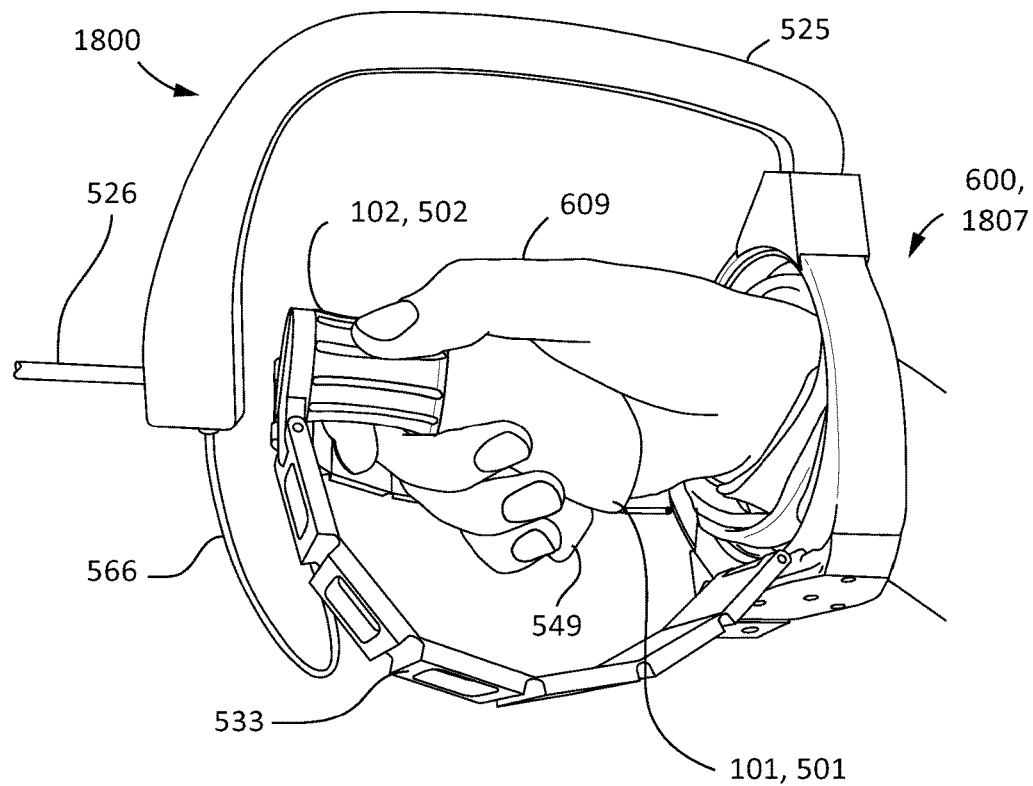
FIG. 19B shows a slightly enlarged view of the device of FIG. 19A.
Figure 19C:
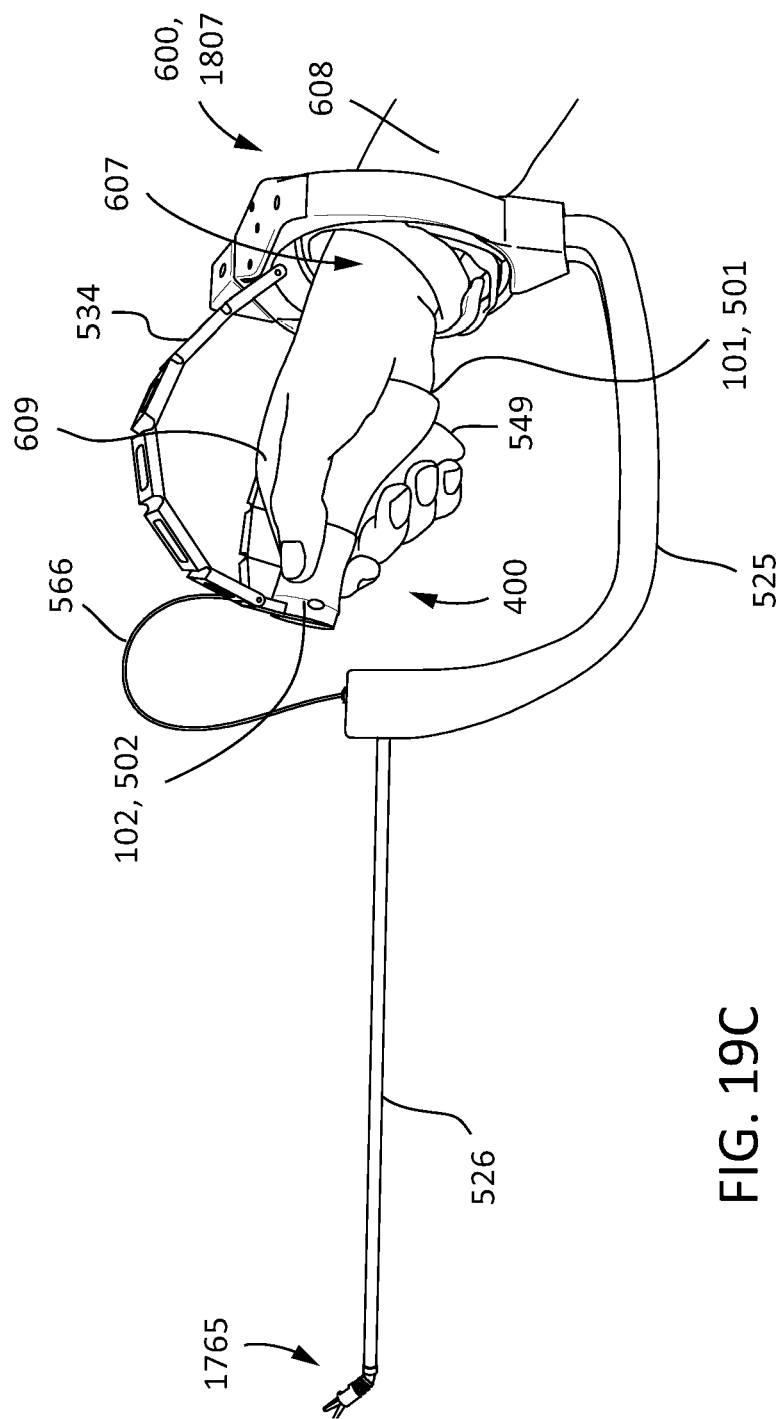
FIG. 19C shows the device of FIG. 19A, in which the user is articulating the handle in pitch and yaw relative to the tool frame; the end-effector jaws track the handle motions.
Figure 20A:
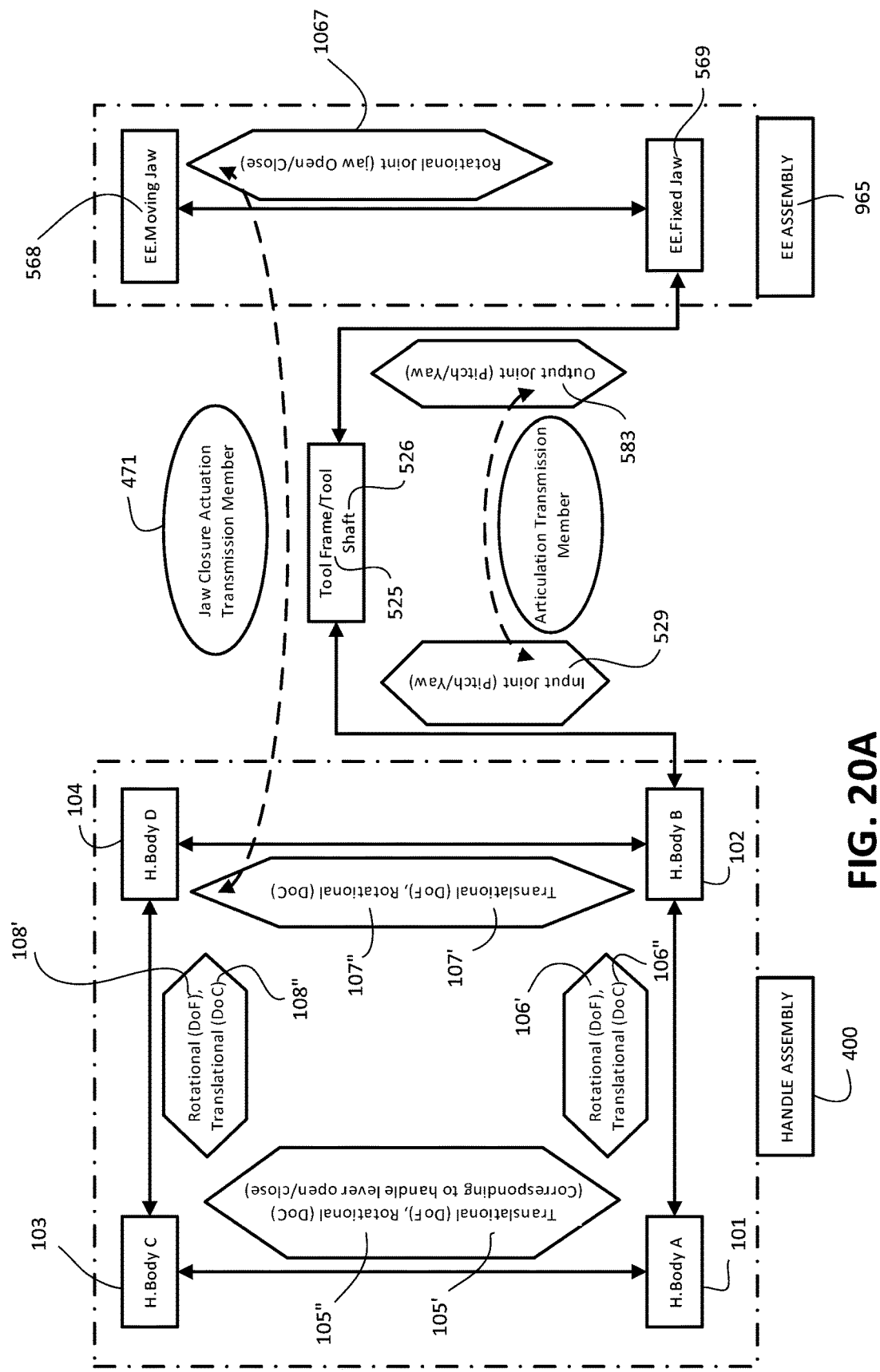
FIG. 20A is a constraint map for the apparatus shown in FIGS. 18A-18D including an unlimited roll handle, input joint, output joint and end-effector configured as a jaw assembly.
Figure 20B:
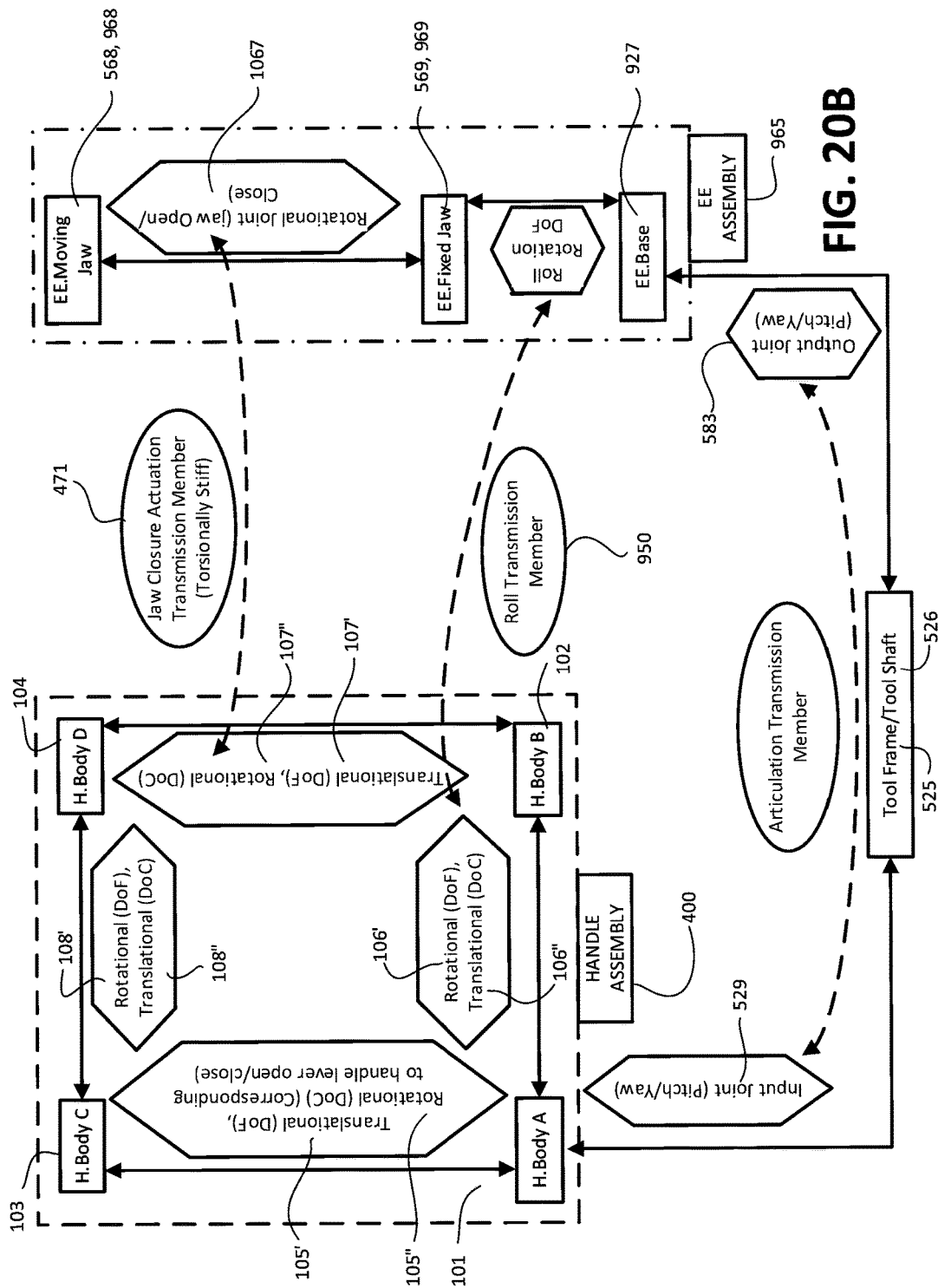
FIG. 20B shows an alternative constraint map for another apparatus as described herein.

FIGS. 18A-18D illustrate one example of a medical device configured as a laparoscopic apparatus including an unlimited roll (unlimited roll) handle, an elongate tool frame, a forearm attachment having multiple degrees of freedom between the user's arm and the tool frame, an end-assembly configured as a jaw assembly and an input joint that encodes pitch and yaw rotation of the handle for transmission to an output joint so that the end-effector may articulate as the handle does. This is illustrated in FIGS. 19A-19C. A schematic constraint diagram for the apparatus show in FIGS. 18A-18D is shown in FIG. 20A. An alternative constraint diagram for an apparatus as described herein is shown in FIG. 20B.

Referring to FIGS. 18A-18D, the overall device comprises a pulley block 1805, a tool frame 525 including a tool shaft 526 (the tool shaft may be considered a portion of the tool frame), all rigidly inter-connected. The pulley block serves as the outer ring 1805 of a forearm attachment apparatus/joint that interfaces with the distal forearm of a user via a wrist cuff 1803, as described above.

In this example, the wrist cuff 1803 and outer ring are all part of the forearm attachment apparatus/joint. The forearm attachment joint comprises an outer ring, a roll ring, a deviation ring, and the wrist cuff (all connected in series), as described in FIG. 6, and provide three rotational degrees of freedom (DoF) between the wrist cuff and the outer ring. These three rotations may be defined as roll, pitch, and yaw. Roll is the rotation direction about the axis of the outer ring, which is the same as the axis of the tool shaft. Pitch and yaw are orthogonal rotations with respect to the roll rotation, as shown in some of the figures. When the device is mounted on the forearm (i.e., the wrist cuff is attached to the forearm/wrist of a user), the forearm attachment joint provides the above three rotational DoF between the tool frame and user/surgeon forearm.

The tool frame extends from the outer ring/pulley block, and is shaped around the handle assembly to accommodate a user's hand (over its entire range of articulation) while holding the handle assembly. The tool frame rigidly connects to a tool shaft, which further extends towards the distal direction (i.e., away from the forearm attachment joint and the user). At the end of the tool-shaft (also referred to as the output of the device) is a two-DoF articulating joint (also referred to as the output joint/end-effector articulating joint). These two degrees of freedom are pitch and yaw rotations, which are controlled/actuated by articulating a device input joint (discussed below) between handle assembly and the pulley block. Additionally, the end-effector is equipped with a pair of jaws that can be opened and closed in response to a handle lever that is part of the handle assembly at the device input (discussed below).

At the proximal end of the device is an input joint between the handle assembly and the pulley block; this joint offers two rotational DoF (pitch and yaw rotations) between the handle assembly and the pulley block. The input joint of the device is a parallel kinematic mechanism comprising two flexure transmission strips and two transmission pulleys (pitch pulley and yaw pulley). The axes of the pulleys 1813, when extrapolated, intersect at a virtual center (VC) in space 1801. For this reason, the parallel kinematic input joint of the device is also referred to as the Virtual Center mechanism or Virtual Center input joint. When the device is mounted on a user forearm via the forearm attachment apparatus and the user's hand holds the handle, the overall device geometry is such that the Virtual Center produced by the parallel kinematic input joint coincides with the center of rotation the user's wrist joint. This ensures a natural, comfortable, unrestricted articulation of the surgeon's wrist while using the device.

Given the above configuration of the device, the yaw and pitch rotations of the user's wrist with respect to his forearm are translated to the corresponding rotations of the handle assembly with respect to the tool pulley block/tool frame. The parallel kinematic design of the virtual center/input mechanism is such that the two rotations (pitch and yaw) of the handle with respect to the pulley block are mechanically separated/filtered into a pitch only rotation seen at the pitch pulley and yaw only rotation seen at the yaw pulley. The pitch pulley and yaw pulley 1813 are pivoted (and mounted) with respect to the pulley block about the pitch rotation and yaw rotation axes, respectively. The pitch and yaw rotations of the handle (and therefore the surgeon's wrist) thus captured at the pitch and yaw transmission pulleys are transmitted to corresponding rotations of the end-effector articulating joint via cables that originate at the transmission pulleys and run through the pulley block, tool frame, and tool shaft all the way to the end-effector.

In addition to the yaw and pitch rotational DoF provided by the input joint, it also provides/allows axial translational DoF along the roll axis. This allows a range of user hand sizes to be accommodated in the device and ensures free and unrestricted hand/wrist articulation.

Furthermore, the transmission strips are stiff in twisting about the roll axis. This ensures that the input mechanism constrains (and therefore transmits) roll rotation from the distal end of the handle assembly (i.e., the dial) via the transmission strips to the pulley block. Note that pulley block serves as the outer ring of the forearm attachment apparatus which provides a well-defined low-resistance rotation about roll axis 1835 with respect to the wrist cuff. This implies that when the user holds the handle in his palm, he can articulate the handle in any desired yaw and pitch directions, resulting in corresponding articulation of the end-effector. Then he can twirl the dial of the handle assembly with his thumb and fingers (typically index finger) while keep the handle articulation fixed. The twirling of the dial (i.e., roll rotation) is transmitted to the pulley block/outer ring via the parallel kinematic input joint (i.e. flexure transmission strip based virtual center mechanism). The pulley block then rotates about the roll axis with respect to the wrist cuff, which is attached to the forearm of the user. As a result the entire tool frame rotates about the roll axis with respect to the forearm of the user. Since the shaft is rigidly connected to the tool frame, the shaft also rotates about the roll axis 1835. The roll rotation of the tool shaft is transmitted to the end-effector as well via the output joint (i.e. end-effector articulating joint). However recall that the articulation of the end-effector (at the output joint) is controlled by the articulation of the handle (at the input joint). Thus, if the latter is held fixed, the former is also held fixed, while roll rotation is transmitted all the way from the twirling motion of the surgeon's fingers to the end-effector. This particular mode of operating the device is called articulated roll.

In addition to producing end-effector roll via twirling of the surgeon's thumb and fingers (resulting in rotating the dial with respect to the handle), another way to produce this roll is when the surgeon rotates (about the roll axis) the entire handle assembly by pronating and supinating his hand and forearm. This roll motion is also transmitted to the tool frame via the transmissions strips of the virtual center mechanism and the pulley block, and subsequently transmitted to the end-effector via the tool shaft. However, the amount of roll motion achieved in this manner is limited by the range of pronation/supination allowed by the user's (i.e. surgeon's) hand/forearm.

On the other hand, by having two discrete components in the handle assembly: the handle and the dial, this limitation is overcome. The handle that remains fixed in the user's hand is indeed limited in its roll angle by the pronation/supination limit of the user's hand/forearm. However, via his fingers the user can roll rotate the dial with respect to the handle endlessly or infinitely. This infinite roll rotation is then transmitted to the end-effector, as described above. This infinite roll ability provides significant and unique functionality to the surgeon in complex surgical procedure such as sewing, knot-tying, etc.

As noted already, the handle assembly comprises a dial and a handle, which are connected by a handle rotation joint which has a single rotational DoF about the roll axis. Additionally, the handle also houses a handle mechanism with a handle lever; as the handle lever is depressed (by the user's fingers, typically middle, ring, and pinky fingers) with respect to the handle, the handle mechanism translates this action into a pulling action of a cable. This pulling action is transmitted via the rotating interface/joint between the handle and the dial. This pulling action exerted on a jaw closure cable is then transmitted to the end-effector via flexible conduit between the dial and tool frame, and then via the tool shaft, via the end-effector articulating joint, all the way to the end-effector jaws. A jaw closure mechanism in the end-effector converts the pulling action of the cable into jaw closure action, as would be needed in shears, graspers, needle-holder, etc.

The virtual center provided by the device input joint coincides with the center of rotation of the wrist joint of the user operating the device. Further, the three rotational axes of the three DoF (yaw 1831, pitch 1833, and roll 1835 rotations) provided by the forearm attachment joint may all intersect at one point, referred to as the center of rotation of the forearm attachment joint. This center of rotation of the forearm attachment joint may coincide with the center of rotation of the device input joint (i.e. the virtual center of rotation of the handle with respect to the pulley block).

The above two imply that the center of rotation of the forearm attachment joint may also coincide with the center of rotation of the user's wrist joint when the device is mounted on a user forearm.

In particular, when the user's wrist in not articulated (i.e., is nominal) the forearm axis should coincide with the axis of the outer ring, which should coincide with the axis of the tool shaft, which should coincide with the axis of the end-effector. This is when the handle is not articulated with respect to the pulley block (i.e. is nominal) and therefore the end-effector is not articulated with respect to the tool shaft.

To enable ease of infinity roll, the overall weight of the device may be distributed such that its center of gravity lies close to the roll axis of the device. This ensures that as the user rolls the device (as described above) he is not working with or against gravity. With the weight of the device supported at the user's forearm and a trocar on the patient's body, locating the center of gravity of the device on the roll axis makes driving the roll rotation relatively effortless because gravity no longer plays a role during the roll rotation.

In addition to all the functionality mentioned above, the overall device design and construction also helps filter out hand tremors and prevent them from reaching the end-effector. In the device, the handle and therefore surgeon's hand are isolated from the pulley block/tool frame/tool shaft by means of the transmissions strips. These flexure transmission strips, because of their material and/or construction, prevent any hand tremors from reaching the tool shaft and end-effector. The tool frame is mounted on the forearm via the forearm attachment joint. Therefore the tool shaft, which is connected to the frame, is controlled by the forearm of the surgeon. Not only does this help drive power motions (translating the tip of the shaft in three directions), but the forearm has much less tremors compared to the hand and therefore the shaft sees less tremors as well.

Thus the transmission strips may help separate out and transmit the yaw and pitch rotations of the handle with respect to the pulley block (equivalently, the yaw and pitch rotations of the hand with respect to the forearm) to pitch and yaw transmission pulleys, which are mounted on the pulley block. They also help transmit the roll rotation from the handle assembly to the pulley block, tool frame, tool shaft, all the way to the end-effector. They also help filter out or block hand tremors from reaching the pulley block, and therefore the tool frame, and therefore the tool shaft, and therefore the end-effector.

The use of a rotating handle mechanism enables surgeons to have better control with the surgical instrument during surgery. Better control is a result of being able to transfer natural, ergonomic, and intuitive motion from the surgeon's hand/wrist/forearm to the end-effector. The virtual center mechanism allows a mapping of pitch and yaw rotations of the surgeon's wrist to be transferred intuitively and fluidly to corresponding rotations of the end-effector articulating joint. Without the rotating handle mechanism to perform a roll of the end-effector the surgeon is limited to pronation and supination of his forearm which has a limit to the amount of roll that can be biomechanically achieved. To perform an articulated roll in which the axis of the roll maintains offset from the axis of the forearm, pronation and supination are combined with flexion and extension of the wrist. Due to the limitations in the human body this rotation in limited in both total roll angle as well as the offset angle from surgeon's wrist axis. Pronation, supination, flexion, and extension of the wrist all have various maximum articulation angles therefore to perform an articulated roll where the axis of the roll remains constant the angle of the roll will be limited to the by the maximum angle the hand can make with wrist in the worst possible orientation.

With the addition of the unlimited roll handle assembly, the surgical instruments described herein are able to intuitively, fluidly, and ergonomically have the end-effector directly inherit or achieve yaw, pitch, and roll that is observed at the input of the device. In addition to pronation and supination of the surgeon's wrist, roll is also transferred to the end-effector with the rolling of the handle dial. When the handle is in an articulated position where the axis of the end-effector is no longer concentric with the axis of the forearm, the surgeon is able to ergonomically perform an articulated roll by keeping the wrist fixed and rolling the handle dial with their thumb/fingers. This enables an articulated roll in every orientation of the wrist with the roll angle being only limited to that specific orientation of the wrist. The roll of the end-effector is no longer limited in rotation by the surgeon's limitation in pronation, supination, flexion, and extension. By controlling the roll of the instrument through the handle dial by their thumb/fingers, the surgeon is able to perform an INFINITE amount of roll while still being able to use the handle actuation input (i.e. lever) to control the open/close actuation of the end-effector in any articulation or roll orientation.

In addition, the unlimited roll handle assemblies described herein enable simultaneous and predictable control of all the minimal access tool's advanced features with an ergonomic interface. This handle features power motions, finesse motions and intuitive control of articulation. These three actions are individually aligned to optimal regions of the user's hand. Power motions such as gripping the handle and lever to close the jaw are confined to the palm and rear fingers. Finesse motions such as rotating the dial are aligned to the thumb and first fingers (e.g., index finger). The separation of power and finesse actions to these regions of the hand minimizes user fatigue. This also reduces the cognitive load for the user, reducing their mental fatigue. Similar to using a computer joystick, articulation is controlled by gently directing the handle to the desired angle.

The unlimited roll handle apparatuses described herein enable the simultaneous actions of open/close, roll rotation and articulation (or any combination). Like our own hand, motions are fluid and natural. Performing a "running stitch" by rotating the dial in continuous direction without unwinding, unlocking or other intermediate step is a novelty compared with other suturing instruments. This is made possible by balancing the instrument and simplifying the mechanics of instrument rotation. When the dial on the handle is rotated, the entire instrument rotates or orbits in the same direction around the user's wrist. During this process, the virtual center also rotates but remains focused at the center of the user's wrist. Consequently, performance is consistent and predictable, even during complex moves like an articulated axial rotation.

As perceived by the user, the handles described herein enable a finesse roll of the handle while engaging the closure mechanism. Initially, the rotation mechanism within the handle as previously described comprises optimized bearings between the various bodies within the mechanism. It is by way of the bearings between various bodies of the rotation mechanism that the surgeon does not notice any difference in the resistance to rotate when the jaw closure lever is engaged or disengaged. Infinite rotation of the handle is enabled by a swivel joint and several keying features within the rotation mechanism which prevent the jaw closure cable from twisting upon itself during rotation.

During use, these handles may allow the surgeon to perform an articulation of the end-effector of the overall surgical device by articulating their own wrist while comfortably holding the base of the handle and closure lever. Articulation of the unlimited roll handle apparatus leverages the distal end of the rotation knob to drive the transmission strips about their articulation pulleys centered over the surgeon's wrist, also known as the virtual center mechanism. Actuation of these two pulleys drives articulation cables through the frame to control the corresponding articulation of the end-effector. Once an articulated position is established, the surgeon may choose to close the jaw by activating the closure lever on the handle. The process of driving a needle requires that the surgeon roll rotate the end-effector about its articulated axis therefore driving the needle about its curvature axis through various tissue planes. These handles may (in conjunction with the other features described herein) provide the surgeon with easy access to the rotation knob where rotation of this mechanism will drive rotation of the transmission strips and the articulation pulleys about the surgeon's wrist as enabled by the three-axis wrist gimbal (i.e. the forearm attachment joint). The wrist gimbal constrains and centers the device about the surgeon's wrist so that rotation of the rotation knob (i.e. dial) and VC mechanism drives a predictable concentric rotation of the pulley block, frame, tool shaft and end-effector about the surgeon's wrist.

These devices enable finesse rotation control and minimize resistances to rotation located in the handle rotation mechanism (addressed via bearings) and at the wrist gimbal (addressed via minimized contact surfaces and low friction plastic materials), overall balance of the device (addressed by establishing a center of gravity on the axis of rotation and redistribution of weight throughout the device), and the use of transmission strips which offer little compliance in torsion/twisting about roll axis.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A medical device, the device comprising:
   an elongate tool frame having a forearm attachment portion at a proximal end, the elongate frame having a tool axis;
   an end-effector at a distal end of the elongate tool frame;
   a handle that provides unlimited roll to the end-effector, wherein the handle includes:
   a first handle portion,
   a second handle portion coupled to the first handle portion so that the second handle portion has one rotational degree of freedom in a first axis relative to the first handle portion but is translationally constrained relative to the first handle portion along the first axis,
   a push rod within the first handle portion and coupled to the first handle portion so that it has one translational degree of freedom along the first axis relative to the first handle portion but is rotationally constrained about the first axis relative to the first handle portion,
   a shuttle body within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion, and
   an end-effector control input on the first handle portion coupled to the push rod and configured to translate the push rod along the first axis,
   wherein rotation of the second handle portion is transmitted to the end-effector so that the end-effector rotates with the second handle portion; and
   a cuff having a passage therethrough that is configured to hold a wrist or forearm of a user, wherein the cuff is configured to couple to the forearm attachment portion of the tool frame.

2. The device of claim 1, further comprising a joint between the forearm attachment portion of the tool frame and the cuff, wherein the joint is configured to provide one or more rotational degrees of freedom between the cuff and the forearm attachment portion of the tool frame.

3. The device of claim 1, further comprising one or more joints between the forearm attachment portion of the tool frame and the cuff, wherein the one or more joints are configured to provide one or more of a roll degree of freedom with respect to the tool axis, a pitch degree of freedom and a yaw degree of freedom between the cuff and the forearm attachment portion of the tool frame.

4. The device of claim 1, wherein the rotation of the second handle portion is transmitted to the end-effector because the elongate tool frame is coupled to the second handle portion so that the elongate tool frame is rotationally constrained relative to the second handle portion and the end-effector is coupled to the elongate tool frame so that the end-effector is rotationally constrained relative to the elongate tool frame.

5. The device of claim 1, wherein the rotation of the second handle portion is transmitted to the end-effector through a rotation transmission extending between the second handle portion and the end-effector.

6. The device of claim 1, further comprising an input joint between the handle and the tool frame, wherein the input joint provides a pitch degree of freedom between the handle and the tool about a pitch axis of rotation and a yaw degree of freedom between the handle and the tool about a yaw axis of rotation.

7. The device of claim 1, further comprising an input joint between the handle and the tool frame and an output joint between the tool frame and the end-effector, wherein the input joint comprises a pitch motion path and a yaw motion path, further wherein the pitch motion path and the yaw motion path are independent and coupled in parallel between the handle and the tool frame, wherein the pitch motion path encodes pitch motion of the handle relative to the tool frame for transmission to the output joint but does not encode yaw motion of the handle relative to the tool frame for transmission to the output joint, and wherein the yaw motion path encodes yaw motion of the handle relative to the tool frame for transmission to the output joint but does not encode pitch motion of the handle relative to the tool frame for transmission to the output joint.

8. The device of claim 7, wherein the pitch axis of rotation and the yaw axis of rotation intersect in a center of rotation that is proximal to the handle.

9. The device of claim 7, further comprising a pitch transmission member and a yaw transmission member extending from the input joint to the output joint, wherein the pitch transmission member transmits pitch rotations and the yaw transmission member transmits yaw rotations of the input joint to corresponding rotations of the output joint.

10. The device of claim 1, wherein the end-effector is configured as a jaw assembly configured so that the actuation of the end-effector control input opens or closes the jaw assembly.

11. The device of claim 1, wherein the end-effector includes a second end-effector portion that is movably coupled to a first end-effector portion; and further comprising a transmission cable connecting the shuttle body to the second end-effector portion so that actuation of the end-effector control input on the handle moves the second end-effector portion relative to the first end-effector portion when the second handle portion is in any rotational position about the first axis relative to the first handle portion.

12. The device of claim 11, wherein the transmission cable comprises a rope or braided material that is compliant in compression, torsion and bending.

13. The device of claim 1, wherein the first handle portion comprises a palm grip configured to be held in a user's palm.

14. The device of claim 1, wherein the end-effector control input comprises a trigger, lever or button on the first handle portion configured for actuation by one or more of a user's fingers and thumb.

15. The device of claim 1, wherein the second handle portion comprises a knob or dial having a grip configured to be rotated by one or more of a user's fingers and thumb.

16. A medical device, the device comprising:
an elongate tool frame having a forearm attachment portion at a proximal end, the elongate frame having a tool axis;
an end-effector at a distal end of the elongate tool frame;
a handle that provides unlimited roll to the end-effector, wherein the handle includes:
a first handle portion,
a second handle portion coupled to the first handle portion so that the second handle portion has one rotational degree of freedom in a first axis relative to the first handle portion but is translationally constrained relative to the first handle portion along the first axis,
a push rod within the first handle portion and coupled to the first handle portion so that it has one translational degree of freedom along the first axis relative to the first handle portion but is rotationally constrained about the first axis relative to the first handle portion,
a shuttle body within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion, and
an end-effector control input on the first handle portion coupled to the push rod and configured to translate the push rod along the first axis,
wherein rotation of the second handle portion is transmitted to the end-effector so that the end-effector rotates with the second handle portion; and
a cuff having a passage therethrough that is configured to hold a wrist or forearm of a user; and
a joint between the forearm attachment portion of the tool frame and the cuff, wherein the joint provides one or more of a roll degree of freedom, a pitch degree of freedom and a yaw degree of freedom between the cuff and the forearm attachment portion of the tool frame, and wherein actuation of the end-effector control input on the handle actuates the end-effector when the second handle portion is in any rotational position about the first axis relative to the first handle portion.

17. A medical device, the device comprising:
an end-effector at a distal end of an elongate tool frame;
a handle that provides unlimited roll to an end-effector, wherein the handle includes:
a first handle portion,
a second handle portion coupled to the first handle portion so that the second handle body has one rotational degree of freedom in a first axis relative to the first handle portion but is translationally constrained relative to the first handle portion along the first axis,
a push rod within the first handle portion and coupled to the first handle portion so that it has one translational degree of freedom along the first axis relative to the first handle portion but is rotationally constrained about the first axis relative to the first handle portion,
a shuttle body within the second handle portion, wherein the shuttle body is coupled to the push rod so that it has one rotational degree of freedom about the first axis relative to the push rod but is translationally constrained along the first axis relative to the push rod, further wherein the shuttle body is coupled to the second handle portion so that it has one translational degree of freedom along the first axis relative to the second handle portion but is rotationally constrained about the first axis relative to the second handle portion, and
an end-effector control input on the first handle portion coupled to the push rod and configured to translate the push rod along the first axis,
wherein rotation of the second handle portion is transmitted to the end-effector so that the end-effector rotates with the second handle portion;
an input joint between the handle and the tool frame configured to encode motion of the handle about a pitch axis of rotation relative to the tool frame for transmission to an output joint, and further configured to encode motion of the handle about a yaw axis of rotation relative to the tool frame for transmission to an output joint, wherein the pitch axis of rotation and the yaw axis of rotation intersect in a center of rotation, wherein the end-effector is coupled to the tool frame by the output joint;
a cuff having a passage therethrough that is configured to hold a wrist or forearm of a user; and
a joint between the forearm attachment portion of the tool frame and the cuff, wherein the joint provides one or more of a roll degree of freedom, a pitch degree of freedom and a yaw degree of freedom between the cuff and the forearm attachment portion of the tool frame,
and wherein actuation of the end-effector control input on the handle actuates the end-effector when the second handle portion is in any rotational position about the first axis relative to the first handle portion.

\* \* \* \* \*